(12) United States Patent
Schmeck et al.

(10) Patent No.: US 8,227,511 B2
(45) Date of Patent: Jul. 24, 2012

(54) SUBSTITUTED CHROMANOL DERIVATIVES AND THEIR USE

(75) Inventors: Carsten Schmeck, Mülheim (DE); Hilmar Bischoff, Wuppertal (DE); Volkhart Li, Velbert (DE); Klemens Lustig, Wuppertal (DE); Michael Thutewohl, Erstfeld (CH); Alexandros Vakalopoulos, Hilden (DE); Olaf Weber, Wülfrath (DE)

(73) Assignee: Bayer Intellectual Property GmbH, Monheim (DE)

( * ) Notice: Subject to any disclaimer, the term of this patent is extended or adjusted under 35 U.S.C. 154(b) by 623 days.

(21) Appl. No.: 12/225,211

(22) PCT Filed: Mar. 7, 2007

(86) PCT No.: PCT/EP2007/001930
§ 371 (c)(1),
(2), (4) Date: Jul. 6, 2009

(87) PCT Pub. No.: WO2007/107243
PCT Pub. Date: Sep. 27, 2007

(65) Prior Publication Data
US 2009/0306197 A1    Dec. 10, 2009

(30) Foreign Application Priority Data
Mar. 18, 2006   (DE) .................. 10 2006 012 548

(51) Int. Cl.
*A61K 31/352* (2006.01)
*C07D 311/04* (2006.01)
*C07D 311/96* (2006.01)
(52) U.S. Cl. ......... 514/456; 514/455; 549/332; 549/401
(58) Field of Classification Search .................. 514/455, 514/456; 549/332, 401
See application file for complete search history.

(56) References Cited

U.S. PATENT DOCUMENTS

| 5,925,645 | A | 7/1999 | Schmidt et al. |
| 5,932,587 | A | 8/1999 | Schmeck et al. |
| 6,063,788 | A | 5/2000 | Brandes et al. |
| 6,069,148 | A | 5/2000 | Schmidt et al. |
| 6,121,330 | A | 9/2000 | Muller-Gliemann et al. |
| 6,127,383 | A | 10/2000 | Schmidt et al. |
| 6,207,671 | B1 | 3/2001 | Schmidt et al. |
| 6,291,477 | B1 | 9/2001 | Schmidt et al. |
| 6,387,929 | B1 | 5/2002 | Stoltefuss et al. |
| 6,562,976 | B2 | 5/2003 | Schmidt et al. |
| 6,586,613 | B1 | 7/2003 | Brandes et al. |
| 6,897,317 | B2 | 5/2005 | Schmidt et al. |
| 6,958,346 | B2 | 10/2005 | Stoltefuss et al. |
| 7,192,971 | B2 | 3/2007 | Stoltefuss et al. |
| 2002/0042515 | A1 | 4/2002 | Schmidt et al. |
| 2005/0043341 | A1 | 2/2005 | Gielen et al. |
| 2006/0247303 | A1 | 11/2006 | Bischoff et al. |
| 2008/0194609 | A1 | 8/2008 | Bischoff et al. |
| 2008/0255068 | A1 | 10/2008 | Bischoff et al. |

FOREIGN PATENT DOCUMENTS

| EP | 0818197 A1 | 1/1998 |
| EP | 818448 A1 | 1/1998 |
| WO | WO-98/04528 A2 | 2/1998 |
| WO | 9839299 A1 | 9/1998 |
| WO | WO 99/14174 | 3/1999 |
| WO | WO-99/14215 A1 | 3/1999 |
| WO | WO-99/15504 A1 | 4/1999 |
| WO | 0109144 A1 | 2/2001 |
| WO | WO-03/028727 A1 | 4/2003 |

OTHER PUBLICATIONS

P. A. McCarthy: "New Approaches to Atherosclerosis: An Overview," Medicinal Research Reviews, vol. 13, No. 2, 1993, pp. 139-159.
P. J. Barter et al.: "High Density Lipoproteins and Coronary Heart Disease," Atherosclerosis, vol. 121, 1996, pp. 1-12.
A. R. Tall: "Plasma Cholesteryl Ester Transfer Protein," Journal of Lipid Research, vol. 34, 1993, pp. 1255-1274.
T. L. Swenson et al.: "Mechanism of Cholesteryl Ester Transfer Protein Inhibition by a Neutralizing Monoclonal Antibody and Mapping of the Monoclonal Antibody Epitope," Teh Journal of Biological Chemistry, vol. 264, No. 24, Aug. 25, 1989, pp. 14318-14326.
Third Report of the National Cholesterol Education Program (NCEP) Expert Panel on Detection, Evaluation, and Treatment of High Blood Cholesterol in Adults (Adult Treatment Panel III) Final Report, Circulation 2002, 106; 3143.
C. R. Sirtori: "New Targets for Lipid Lowering and Atherosclerosis Prevention," Pharmac. Ther. vol. 67, No. 3, 1995, pp. 433-447.
C. L. Bisgaier et al.: "Use of Fluorescent Cholestertyl Ester Microemulsions in Cholesteryl Ester Transfer Portein Assays," Journal of Lipid Research, vol. 34, 1993, pp. 1625-1634.
A. Gotti et al.: "Rearrangement of Isoxazoline-5-Spiro Derivatives. Part 7. Thermal Rearrangement of 4,5-Dihydro and Tetrahydroisoxazole-5-Spirocyclobutanes to Azepin-4-one Derivatives," Tetrahedron, vol. 48, No. 25, 1992, pp. 5283-5300.
F. Seye-Mandavi et al.: "Reactivity Enhancement through Strain and Electronic Effects: ∝-Heterocyclopropylidenacetates as Powerful Michael Receptors," Tetradedron Letters, vol. 27, No. 41, 1986, pp. 6185-6188.
A. Weichert et al.: "Palladium(0) Catalyzed Cross Coupling Reactions of Hindered, Double Activated Aryl Halides with Organozinc Reagents—The Effect of Copper(I) Cocatalysis," Syunlett, May 1996, pp. 473-474.
M. Ueda et al.: "A Large Accelerating Effect of Tri(*tert*-butyl)phosphine in teh Rhodium-Catalyzed Addition of Arylboronic Acids to Aldehydes," J. org. Chem., vol. 65, 2000, pp. 4450-4452.

(Continued)

*Primary Examiner* — Sreeni Padmanabhan
*Assistant Examiner* — Sahar Javanmard
(74) *Attorney, Agent, or Firm* — Karen B. King

(57) ABSTRACT

The present invention relates to substituted chromanol derivatives, to processes for their preparation, to their use on their own or in combination for the treatment and/or prevention of diseases and to their use for preparing medicaments for the treatment and/or prevention of diseases, in particular for the treatment and/or prevention of cardiovascular disorders.

7 Claims, No Drawings

OTHER PUBLICATIONS

J. Hassan et al.: "Aryl-Aryl Bond Formation One Century after the Discovery of the Ullmann Reaction," Chem. Rev., vol. 102, 2002, pp. 1359-1469.

L. Xie et al.—Anti-AIDS Agents. 42. Syntesis and Anti-HIV Activity of Disubstituted (3'R,4'R)-3',4'-Di-O-(S)-camphanoyl-(+)-cis-khellactone Analogues, J. Med Chem, vol. 44, 2001, pp. 664-671.

J. Dinchuk et al.: "Remodelling of Lipoproteins in Transgenic Mice Expressing Human Cholesteryl Ester Transfer Protein," Biochimica et Biophysica Acta, vol. 1255, 1995, pp. 301-310.

Paulsen, et al., Fluorine-Substitution in Cholesteryl Ester Transfer Protein Inhibitors (CETP-Inhibitors)—Biology, chemistry, SAR and Properties, CHIMIA, 2004, 58:3, pp. 123-127.

U.S. Appl. No. 11/793,482, filed Jan. 16, 2008.

U.S. Appl. No. 11/793,483, filed Apr. 18, 2008.

SUBSTITUTED CHROMANOL DERIVATIVES AND THEIR USE

RELATED APPLICATIONS/PATENTS AND INCORPORATION BY REFERENCE

This application is a National Stage Application filed under 35 U.S.C. §371 based on International Application No. PCT/EP2007/001930, filed Mar. 7, 2007, which claims priority to German Patent Application Number 10 2006 012 548.7, filed Mar. 18, 2006, the entire contents each of which are incorporated herein by reference.

The foregoing applications, and all documents cited therein and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

The present invention relates to substituted chromanol derivatives, to processes for their preparation, to their use on their own or in combination for the treatment and/or prevention of diseases and to their use for preparing medicaments for the treatment and/or prevention of diseases, in particular for the treatment and/or prevention of cardiovascular disorders.

Coronary heart disease caused by arteriosclerosis is one of the main causes of death in modern society. In a large number of studies, it was shown that low plasma concentrations of HDL cholesterol are an important risk factor for the development of arteriosclerosis [Barter and Rye, *Atherosclerosis* 121, 1-12 (1996)]. HDL (high density lipoprotein), in addition to LDL (low density lipoprotein) and VLDL (very low density lipoprotein), is a class of lipoproteins whose most important function is the transport of lipids, such as, for example, cholesterol, cholesterol esters, triglycerides, fatty acids or phospholipids, in the blood. High LDL cholesterol concentrations (>160 mg/dl) and low HDL cholesterol concentrations (<40 mg/dl) contribute substantially to the development of arteriosclerosis [ATP III Guidelines, Report of the NCEP Expert Panel]. In addition to coronary heart disease, unfavorable HDL/LDL ratios also promote the development of peripheral vascular disorders and stroke. Accordingly, novel methods for elevating HDL cholesterol in the plasma are a therapeutically useful advance in the prevention and treatment of arteriosclerosis and the disorders associated therewith.

Cholesterol ester transfer protein (CETP) mediates the exchange of cholesterol esters and triglycerides between the different lipoproteins in the blood [Tall, *J. Lipid Res.* 34, 1255-74 (1993)]. Of particular importance here is the transfer of cholesterol esters from HDL to LDL, which results in a reduction of the plasma HDL cholesterol concentration. Accordingly, inhibition of CETP should result in elevated plasma HDL cholesterol concentrations and a reduction of the plasma LDL cholesterol concentrations and thus in a therapeutically useful effect on the lipid profile in the plasma [McCarthy, *Medicinal Res. Rev.* 13, 139-59 (1993); Sitori, *Pharmac. Ther.* 67, 443-47 (1995); Swenson, *J. Biol. Chem.* 264, 14318 (1989)].

Substituted tetrahydronaphthalenes and tetrahydroquinolines having CETP-inhibitory action are known from EP 0 818 448-A1, WO 99/14174, WO 99/14215, WO 99/15504 and WO 03/028727. Heterocyclic fused pyridines as CETP inhibitors are disclosed in EP 0 818 197-A1. WO 98/04528 describes substituted pyridine and phenyl derivatives as glucagon antagonists for the treatment of diabetes.

It was an object of the present invention to provide novel substances for controlling disorders, in particular cardiovascular disorders, which substances have an improved therapeutic profile.

The present invention provides compounds of the general formula (I)

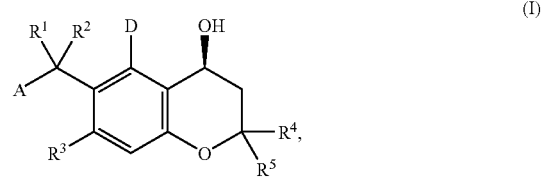

in which
A represents a group of the formula

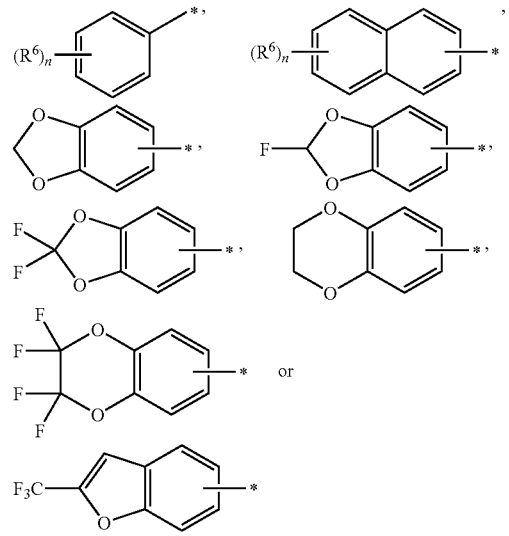

in which
* represents the point of attachment to the $CR^1R^2$ grouping,
$R^6$ represents a substituent selected from the group consisting of halogen, cyano, $(C_1-C_6)$-alkyl and $(C_1-C_6)$-alkoxy, where alkyl and alkoxy for their part may be substituted up to five times by fluorine,
and
n represents the number 0, 1, 2 or 3,
where, if the substituent $R^6$ is present more than once, its meanings may be identical or different,
D represents $(C_3-C_8)$-alkyl, $(C_4-C_8)$-cycloalkyl, $(C_4-C_8)$-cycloalkenyl, $(C_6-C_{10})$-aryl, 5- or 6-membered heteroaryl, tetrahydrofuranyl or tetrahydropyranyl, where
aryl and heteroaryl for their part may be substituted by halogen, cyano, $(C_1-C_6)$-alkyl, $(C_1-C_6)$-alkoxy, trifluoromethyl or trifluoromethoxy
and
cycloalkyl and cycloalkenyl for their part may be substituted by fluorine or $(C_1-C_6)$-alkyl,
$R^1$ represents hydrogen, fluorine, hydroxyl, methoxy, mercapto or methyl,
$R^2$ represents hydrogen
or
$R^1$ and $R^2$ together with the carbon atom to which they are attached form a carbonyl group,
$R^3$ represents $(C_1-C_6)$-alkyl or $(C_3-C_7)$-cycloalkyl
and
$R^4$ and $R^5$ independently of one another represent hydrogen or $(C_1-C_4)$-alkyl or together with the carbon atom to which they are attached form a spiro-linked 3- to 5-membered cycloalkyl ring,
and their salts, solvates and solvates of the salts.

Compounds according to the invention are the compounds of the formula (I) and their salts, solvates and solvates of the salts, the compounds of the formulae shown below, which are included in formula (I), and their salts, solvates and solvates of the salts, and the compounds mentioned below as working examples, which are included in formula (I), and their salts, solvates and solvates of the salts, if the compounds mentioned below included in formula (I) are not already salts, solvates and solvates of the salts.

Depending on their structure, the compounds according to the invention can exist in stereoisomeric forms (enantiomers, diastereomers). Accordingly, the present invention includes the enantiomers or diastereomers and their respective mixtures. The stereoisomerically uniform components can be isolated from such mixtures of enantiomers and/or diastereomers in a known manner.

If the compounds according to the invention can be present in tautomeric forms, the present invention includes all tautomeric forms.

In the context of the present invention, preferred salts are physiologically acceptable salts of the compounds according to the invention. However, salts which for their part are unsuitable for pharmaceutical applications but which can be used, for example, for isolating or purifying the compounds according to the invention are also included.

Physiologically acceptable salts of the compounds according to the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of customary bases, such as, by way of example and by way of preference, alkali metal salts (for example sodium salts and potassium salts), alkaline earth metal salts (for example calcium salts and magnesium salts) and ammonium salts, derived from ammonia or organic amines having 1 to 16 carbon atoms, such as, by way of example and by way of preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention, solvates refer to those forms of the compounds according to the invention which, in solid or liquid state, form a complex by coordination with solvent molecules. Hydrates are a special form of solvates where the coordination is with water. In the context of the present invention, preferred solvates are hydrates.

Moreover, the present invention also includes prodrugs of the compounds according to the invention. The term "prodrugs" includes compounds which for their part may be biologically active or inactive but are converted (for example metabolically or hydrolytically) into the compounds according to the invention during their residence time in the body.

In the context of the present invention, the substituents are, unless specified otherwise, as defined below:

In the context of the invention, $(C_1-C_6)$-alkyl, $(C_3-C_8)$-alkyl, $(C_3-C_6)$-alkyl and $(C_1-C_4)$-alkyl represent a straight-chain or branched alkyl radical having 1 to 6, 3 to 8, 3 to 6 and 1 to 4 carbon atoms, respectively. In the case of the groups D and $R^3$, an alkyl radical which is branched in the 1-position and has 3 to 6 carbon atoms is preferred. In the other cases, a straight-chain or branched alkyl radical having 1 to 4 carbon atoms is preferred. The following radicals may be mentioned by way of example and by way of preference: methyl, ethyl, n-propyl, isopropyl, n-butyl, isobutyl, sec-butyl, tert-butyl, n-pentyl, 1-methylbutyl, 1-ethylpropyl, 2,2-dimethylpropyl, n-hexyl, 1-methylpentyl, 1-ethylbutyl, n-heptyl, 1-ethylpentyl, 1-propylbutyl and n-octyl.

In the context of the invention, $(C_1-C_6)$-alkoxy and $(C_1-C_4)$-alkoxy represent a straight-chain or branched alkoxy radical having 1 to 6 and 1 to 4 carbon atoms, respectively. Preference is given to a straight-chain or branched alkoxy radical having 1 to 4 carbon atoms. The following radicals may be mentioned by way of example and by way of preference: methoxy, ethoxy, n-propoxy, isopropoxy, n-butoxy, tert-butoxy, n-pentoxy and n-hexoxy.

In the context of the invention, $(C_4-C_8)$-cycloalkyl, $(C_3-C_7)$-cycloalkyl and $(C_3-C_6)$-cycloalkyl represent a monocyclic saturated cycloalkyl group having 4 to 8, 3 to 7 and 3 to 6 carbon atoms, respectively. In the case of group D, a cycloalkyl radical having 5 or 6 carbon atoms is preferred and in the case of group $R^3$, a cycloalkyl radical having 4 to 6 carbon atoms is preferred. The following radicals may be mentioned by way of example and by way of preference: cyclopropyl, cyclobutyl, cyclopentyl, cyclohexyl, cycloheptyl and cyclooctyl.

In the context of the invention, $(C_4-C_8)$-cycloalkenyl represents a monocyclic cycloalkyl group having 4 to 8 carbon atoms and one double bond. Preference is given to a cycloalkenyl radical having 5 or 6 carbon atoms. The following radicals may be mentioned by way of example and by way of preference: cyclobutenyl, cyclopentenyl, cyclohexenyl, cycloheptenyl and cyclooctenyl.

In the context of the invention, $(C_6-C_{10})$-aryl represents an aromatic carbocycle having 6 or 10 ring carbon atoms. Preferred aryl radicals are phenyl and naphthyl.

In the context of the invention, 5- or 6-membered heteroaryl represents an aromatic heterocycle (heteroaromatic) having a total of 5 or 6 ring atoms which contains one or two ring heteroatoms from the group consisting of N, O and/or S and which is attached via a ring carbon atom or, if appropriate, a ring nitrogen atom. The following radicals may be mentioned by way of example: furyl, pyrrolyl, thienyl, pyrazolyl, imidazolyl, thiazolyl, oxazolyl, isoxazolyl, isothiazolyl, pyridyl, pyrimidinyl, pyridazinyl and pyrazinyl. Preference is given to 5-membered heteroaryl radicals, such as, in particular, furyl, thienyl, thiazolyl, oxazolyl, isoxazolyl and isothiazolyl.

In the context of the invention, halogen includes fluorine, chlorine, bromine and iodine. Preference is given to chlorine and fluorine.

If radicals in the compounds according to the invention are substituted, the radicals may, unless specified otherwise, be mono- or polysubstituted. In the context of the present invention the meanings of all radicals which are present more than once are independent of one another. A substitution with one, two or three identical or different substituents is preferred. Very particular preference is given to the substitution with one substituent.

In the context of the present invention, preference is given to compounds of the formula (I) in which A represents a group of the formula

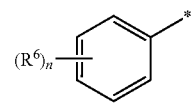

in which

* represents the point of attachment to the $CR^1R^2$ grouping, $R^6$ represents a substituent selected from the group consisting of fluorine, chlorine, cyano, $(C_1-C_4)$-alkyl and $(C_1-C_4)$-alkoxy, where alkyl and alkoxy for their part may be substituted up to five times by fluorine, and n represents the number 0, 1, 2 or 3, where, if the substituent $R^6$ is present more than once, its meanings may be identical or different, D represents phenyl, thienyl, furyl, cyclopentyl, cyclohexyl, cyclopentenyl or cyclohexenyl, where phenyl, thienyl and furyl for their part may be substituted by fluorine, chlorine, cyano, $(C_1-C_4)$-alkyl, $(C_1-C_4)$-alkoxy, trifluoromethyl or trifluoromethoxy and cyclopentyl, cyclohexyl, cyclopentenyl and cyclohexenyl for their part may be substituted by fluorine or $(C_1-C_4)$-alkyl, $R^1$ represents hydrogen, fluorine, hydroxyl or methyl, $R^2$ represents hydrogen or $R^1$ and $R^2$ together with the carbon atom to which they are attached form a carbonyl group, $R^3$ represents $(C_3-C_6)$-alkyl or $(C_3-C_6)$-cycloalkyl and $R^4$ and $R^5$ independently of one another represent hydrogen or methyl or together with the carbon atom to which they are attached form a spiro-linked 3- to 5-membered cycloalkyl ring, and their salts, solvates and solvates of the salts.

In the context of the present invention, particular preference is given to compounds of the formula (I) in which
A represents a group of the formula

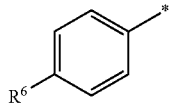

in which

* represents the point of attachment to the $CR^1R^2$ grouping
and $R^6$ represents trifluoromethyl, trifluoromethoxy or tert-butyl, D represents phenyl, 4-fluorophenyl, cyclopentyl, cyclohexyl, cyclopent-1-en-1-yl or cyclohex-1-en-1-yl, $R^1$ represents hydrogen, fluorine or hydroxyl, $R^2$ represents hydrogen or $R^1$ and $R^2$ together with the carbon atom to which they are attached form a carbonyl group, $R^3$ represents isopropyl or cyclopentyl and $R^4$ and $R^5$ represent methyl or together with the carbon atom to which they are attached form a spiro-linked cyclopropyl or cyclobutyl ring, and their salts, solvates and solvates of the salts.

The individual radical definitions given in the respective combinations or preferred combinations of radicals may, independently of the respective given combinations of radicals, also be replaced by any radical definitions of other combinations.

Particular preference is given to combinations of two or more of the preferred ranges mentioned above.

The invention furthermore provides a process for preparing compounds of the formula (I) according to the invention, characterized in that either

[A] a compound of the formula (II)

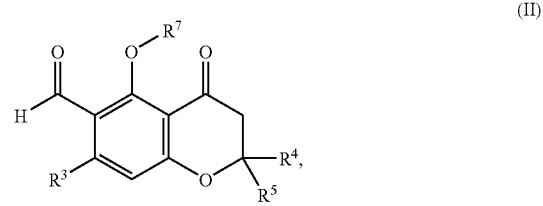

(II)

in which $R^3$, $R^4$ and $R^5$ are each as defined above and $R^7$ represents hydrogen, methyl or a customary hydroxyl protective group, such as, for example, allyl, benzyl, tetrahydropyranyl or trialkylsilyl, is initially, in an inert solvent, if appropriate in the presence of a catalyst, coupled with an organometallic compound of the formula (III)

A-Q    (III), in which A is as defined above and

Q represents Li, —MgBr, —ZnBr or —B(OH)$_2$, to give a compound of the formula (IV)

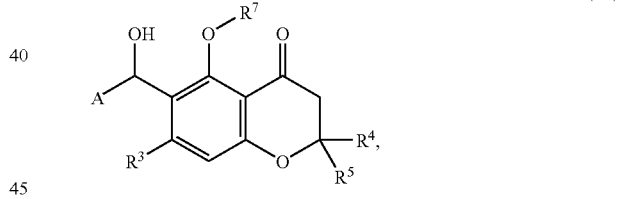

(IV)

in which A, $R^3$, $R^4$, $R^5$ and $R^7$ are each as defined above, this compound is then oxidized to a compound of the formula (V)

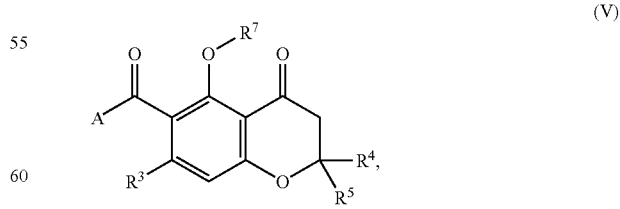

(V)

in which A, $R^3$, $R^4$, $R^5$ and $R^7$ are each as defined above, then if $R^7$ represents methyl or a hydroxyl protective group, this radical is removed using customary methods, the resulting compound of the formula (Va)

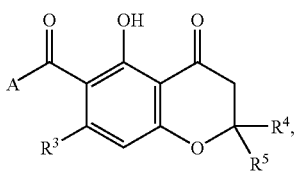

(Va)

in which A, R³, R⁴ and R⁵ are each as defined above
is converted by standard methods into a compound of the formula (VI)

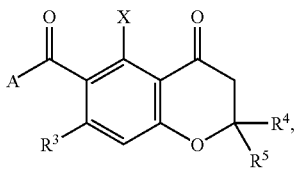

(VI)

in which A, R³, R⁴ and R⁵ are each as defined above
and
X represents a leaving group, such as, for example, chlorine, bromine, iodine, tosylate, mesylate or triflate,
then, in an inert solvent in the presence of a base and a suitable palladium catalyst, coupled with a boronic acid derivative of the formula (VII)

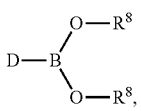

(VII)

in which D is as defined above
and
$R^8$ represents hydrogen or $(C_1-C_4)$-alkyl or both radicals together form a —$C(CH_3)_2$—$C(CH_3)_2$— bridge
to give a compound of the formula (VIII)

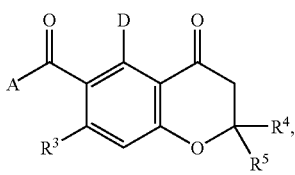

(VIII)

in which A, D, R³, R⁴ and R⁵ are each as defined above,
and this compound is then converted by asymmetric reduction into a compound of the formula (I-A)

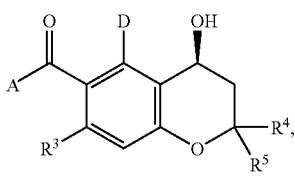

(I-A)

in which A, D, R³, R⁴ and R⁵ are each as defined above
or in a modified order of the reaction steps
[B] a compound of the formula (IIa)

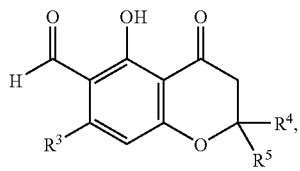

(IIa)

in which R³, R⁴ and R⁵ are each as defined above
is initially converted by standard methods into a compound of the formula (IX)

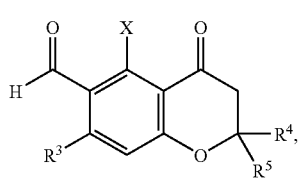

(IX)

in which X, R³, R⁴ and R⁵ are each as defined above,
then, in an inert solvent in the presence of a base and a suitable palladium catalyst, coupled with a boronic acid derivative of the formula (VII) to give a compound of the formula (X)

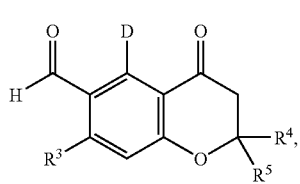

(X)

in which D, R³, R⁴ and R⁵ are each as defined above,
then, in an inert solvent, if appropriate in the presence of a catalyst, reacted with an organometallic compound of the formula (III) to give a compound of the formula (XI)

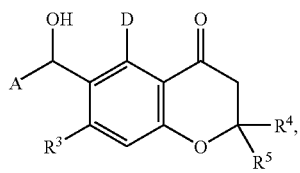

(XI)

in which A, D, R³, R⁴ and R⁵ are each as defined above,
and this compound is then converted by asymmetric reduction into a compound of the formula (I-B)

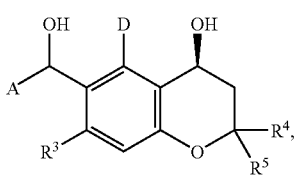

(I-B)

in which A, D, $R^3$, $R^4$ and $R^5$ are each as defined above, or the compound of the formula (XI) is initially converted with the aid of a fluorinating agent into a compound of the formula (XII)

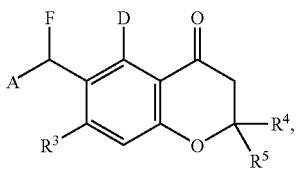

(XII)

in which A, D, $R^3$, $R^4$ and $R^5$ are each as defined above and then, by asymmetric reduction, into a compound of the formula (I-C)

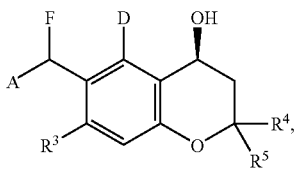

(I-C)

in which A, D, $R^3$, $R^4$ and $R^5$ are each as defined above, and the compounds according to the invention obtained in this manner are, if appropriate, converted with the appropriate (i) solvents and/or (ii) bases or acids into their solvates, salts and/or solvates of the salts.

The compounds of the formulae (I-A), (I-B), (XI) and (XII) obtained in the processes described above can, if appropriate, be modified in the meanings of $R^1$ and $R^2$ using customary reduction, oxidation, fluorination and/or methylation methods, thus providing access to further compounds of the formula (I) according to the invention (see also reaction schemes 1-8 below).

In these transformations if required or expedient, the chromanol hydroxyl group may be protected temporarily by a customary hydroxyl protective group. For this purpose, preference is given to using a trialkylsilyl group; particular preference is given to tert-butyldimethylsilyl. Such protective groups are introduced and removed by known methods [see, for example, T. W. Greene and P. G. M. Wuts, *Protective Groups in Organic Synthesis*, Wiley, New York, 1999].

To introduce the tert-butyldimethylsilyl group, preference is given to using tert-butyldimethylsilyl chloride or tert-butyldimethylsilyl trifluoromethanesulfonate in combination with triethylamine, N,N-diisopropylethylamine, pyridine, 2,6-lutidine or 4-N,N-dimethylaminopyridine as base. The tert-butyldimethylsilyl group is preferably removed with the aid of tetra-n-butylammonium fluoride (TBAF).

Suitable reducing agents for reducing ketones to secondary alcohols are, for example, complex aluminum hydrides or borohydrides, such as lithium hydride, sodium hydride, potassium hydride, zinc borohydride, lithium aluminum hydride, diisobutylaluminum hydride (DIBAL-H), sodium bis(2-methoxyethoxy)aluminum dihydride, lithium trialkylborohydrides or lithium trialkoxyaluminum hydrides, or borane complexes, such as borane/tetrahydrofuran, borane/dimethyl sulfide or borane/N,N-diethylaniline complex.

Suitable inert solvents for process steps (II)+(III)→(IV) and (X)+(III)→(XI) are, for example, ethers, such as diethyl ether, diisopropyl ether, dioxane, tetrahydrofuran, glycol dimethyl ether or diethylene glycol dimethyl ether, or hydrocarbons, such as benzene, xylene, toluene, pentane, hexane, cyclohexane or mineral oil fractions. It is also possible to use mixtures of the solvents mentioned. Preference is given to tetrahydrofuran.

The reactions (II)+(III)→(IV) and (X)+(III)→(XI) can, if appropriate, be carried out in an advantageous manner by adding dialkylzinc compounds or palladium phosphine or rhodium phosphine complexes as catalysts [cf., for example, M. Ueda and N. Miyaura, *J. Org. Chem.* 65, 4450-4452 (2000) and the literature cited therein].

The reactions are generally carried out in a temperature range of from −80° C. to +50° C., preferably at from −80° C. to 0° C.

Suitable oxidizing agents for process step (IV)→(V) are, for example, manganese(IV) oxide, pyridinium chlorochromate (PCC), N-methylmorpholine N-oxide, the 2,2,6,6-tetramethylpiperidin-1-yloxy radical (TEMPO) or Dess-Martin periodinane (1,1-dihydroxy-1,1,1-triacetoxy-1,2-benziodoxol-3(1H)-one). Preference is given to using manganese (IV) oxide or Dess-Martin periodinane.

The leaving group X is preferably a triflate group (trifluoromethylsulfonate). To introduce this group in the process steps (Va)→(VI) and (IIa)→(IX), the phenol derivative (Va) or (IIa) is reacted in an inert solvent, such as dichloromethane or dimethylformamide, with trifluoromethanesulfonic anhydride or, preferably, with N,N-bis(trifluoromethanesulfonyl) aniline in the presence of a base such as potassium carbonate, pyridine, 2,6-lutidine, 4-N,N-dimethyl-aminopyridine (DMAP), triethylamine or N,N-diisopropylethylamine.

Inert solvents for the process steps (VI)+(VII)→(VIII) and (IX)+(VII)→(X) are, for example, alcohols, such as methanol, ethanol, n-propanol, isopropanol, n-butanol or tert-butanol, ethers, such as diethyl ether, dioxane, tetrahydrofuran, glycol dimethyl ether or diethylene glycol dimethyl ether, hydrocarbons, such as benzene, xylene, toluene, hexane, cyclohexane or mineral oil fractions, or other solvents, such as dimethylformamide, dimethylsulfoxide, N,N'-dimethylpropylene urea (DMPU), N-methylpyrrolidone (NMP), pyridine, acetonitrile or else water. It is also possible to use mixtures of the solvents mentioned. Preference is given to dioxane.

Suitable bases for the process steps (VI)+(VII)→(VIII) and (IX)+(VII)→(X) are customary inorganic bases. These include in particular alkali metal hydroxides, such as, for example, lithium hydroxide, sodium hydroxide or potassium hydroxide, alkali metal bicarbonates, such as sodium bicarbonate or potassium bicarbonate, alkali metal or alkaline earth metal carbonates, such as lithium carbonate, sodium carbonate, potassium carbonate, calcium carbonate or cesium carbonate, alkali metal hydrogen phosphates, such as disodium hydrogen phosphate or dipotassium hydrogen phosphate, or alkali metal phosphates, such as trisodium phosphate or tripotassium phosphate. Preference is given to using tripotassium phosphate.

Suitable palladium catalysts for process steps (VI)+(VII)→(VIE) and (IX)+(VII)→(X) ["Suzuki coupling"] are, for example, palladium(II) acetate, tetrakis(triphenylphosphine)-palladium(0), bis(triphenylphosphine)palladium(II) chloride, bis(acetonitrile)palladium(II) chloride or [1,1'-bis (diphenylphosphino)ferrocene]dichloropalladium(II)/ dichloromethane complex [cf., for example, J. Hassan et al., *Chem. Rev.* 102, 1359-1469 (2002)].

The reactions (VI)+(VII)→(VIII) and (IX)+(VII)→(X) are generally carried out in a temperature range of from +20° C. to +150° C., preferably at from +60° C. to +120° C.

The asymmetric reduction to the (S)-chromanol in process steps (VIII)→(I-A), (XI)→(I-B) and (XII)→(I-C) and an analogous reaction is carried out in the presence of catalytic amounts (0.01 to 0.3 mol equivalents) of enantiomerically pure (1R,2S)-1-aminoindan-2-ol as chiral inductor. The reducing agent used here is preferably borane/N,N-diethylaniline complex. The reaction is generally carried out in toluene or in an ether, such as diethyl ether, diisopropyl ether, dioxane, tetrahydrofuran, glycol dimethyl ether or diethylene glycol dimethyl ether, preferably in tetrahydrofuran, in a temperature range of from −80° C. to +50° C., preferably from 0° C. to +30° C.

The fluorination in process step (XI)→(XII) and analogous reactions is generally carried out in a hydrocarbon, such as benzene, toluene, xylene, pentane, hexane or cyclohexane, or in a halogenated hydrocarbon, such as dichloromethane, trichloromethane, carbon tetrachloride, 1,2-dichloroethane, trichloroethylene or chlorobenzene as solvent. Preference is given to toluene or dichloromethane. The fluorinating agent used is preferably diethylaminosulfur trifluoride (DAST) or morpholinosulfur trifluoride. The reaction is generally carried out in a temperature range of from −80° C. to +40° C., preferably at from −60° C. to +20° C.

The compounds of the formula (IIa) can be prepared by converting a compound of the formula (XIII)

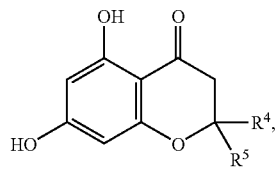

(XIII)

in which $R^4$ and $R^5$ are as defined above
initially by standard methods into a compound of the formula (XIV)

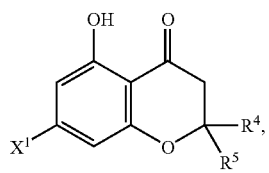

(XIV)

in which $R^4$ and $R^5$ are as defined above
and
$X^1$ represents a leaving group, such as mesylate, tosylate or, in particular, triflate, followed by reaction in an inert solvent in the presence of a suitable catalyst with an organozinc compound of the formula (XVa) or (XVb)

 (XVa)

 (XVb), in which $R^3$ is as defined above,
to give a compound of the formula (XVI)

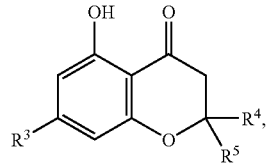

(XVI)

in which $R^3$, $R^4$ and $R^5$ are each as defined above,
which is then formylated with dichloromethyl methyl ether in the presence of a Lewis acid to give the compound of the formula (IIa) (cf. reaction scheme 4).

Compounds of the formula (XIII) can be obtained by Lewis acid-catalyzed reaction of phloroglucinol (XVII) with an acrylic acid derivative of the formula (XVIII)

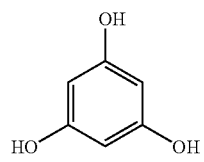

(XVII)

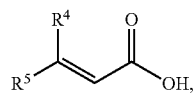

(XVIII)

in which $R^4$ and $R^5$ are as defined above
(cf. reaction schemes 2 and 4).

Compounds of the formula (II) in which $R^7$ represents methyl or a hydroxyl protective group can be obtained by customary processes from compounds of the formula (IIa).

The leaving group $X^1$ used is preferably a triflate group (trifluoromethylsulfonate). To introduce this group in process step (XIII)→(XIV), the phenol derivative (XIII) is reacted in an inert solvent, such as dichloromethane or dimethylformamide, with trifluoromethanesulfonic anhydride or, preferably, with N,N-bis(trifluoromethanesulfonyl)aniline in the presence of a base, such as potassium carbonate, pyridine, 2,6-lutidine, 4-N,N-dimethylaminopyridine (DMAP), triethylamine or N,N-diisopropylethylamine.

Inert solvents for the process step (XIV)+(XVa) or (XVb)→(XVI) are, for example, ethers, such as diethyl ether, diisopropyl ether, methyl tert-butyl ether, dioxane, tetrahydrofuran, glycol dimethyl ether or diethylene glycol dimethyl ether, hydrocarbons, such as benzene, toluene, xylene, hexane, cyclohexane or mineral oil fractions, or other solvents, such as dimethyl-formamide, dimethyl sulfoxide, N,N'-dimethylpropylene urea (DMPU) or N-methylpyrrolidone (NMP). It is also possible to use mixtures of the solvents mentioned. Preference is given to using dimethylformamide.

Suitable catalysts for the process step (XIV)+(XVa) or (XVb)→(XVI) ["Negishi-Kumada coupling"] are, for example, bis(diphenylphosphino)ferrocenepalladium(II) chloride or palladium(II) acetate in combination with triphenylphosphine, with addition of cocatalysts such as copper(I) iodide or lithium chloride [cf., for example, A. Weichert et al., *Synlett*, 473 (1996) and the literature cited therein].

The reaction is generally carried out in a temperature range of from −20° C. to +120° C., preferably at from 0° C. to +60° C.

A suitable Lewis acid for the formylation with dichloromethyl methyl ether in process step (XVI)→(IIa) is, for example, titanium(IV) chloride, titanium(IV) isopropoxide, zinc(II) chloride or magnesium chloride. Preference is given to using titanium(IV) chloride.

A particularly suitable Lewis acid for process step (XVII)+(XVIII)→(XIII) is boron trifluoride. Alternatively, it is also possible to use agents such as methanesulfonic acid or phosphorus pentoxide. The reaction can be carried out in a hydrocarbon, such as benzene, toluene, xylene, hexane or cyclohexane, or in a halogenated hydrocarbon, such as dichloromethane, trichloromethane, carbon tetrachloride, 1,2-dichloroethane, trichloroethylene or chlorobenzene, as solvent, or else without solvent.

Compounds of the formula (II), in which $R^4$ and $R^7$ each represent methyl, $R^5$ represents hydrogen or $(C_1-C_4)$-alkyl and $R^3$ represents, for example, cyclopentyl, can also be prepared by initially converting a compound of the formula (XIX)

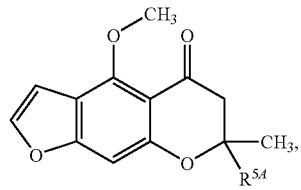
(XIX)

in which
$R^{5A}$ represents hydrogen or $(C_1-C_4)$-alkyl
by ozonolysis or dichromate oxidation into an o-hydroxybenzaldehyde derivative of the formula (XX)

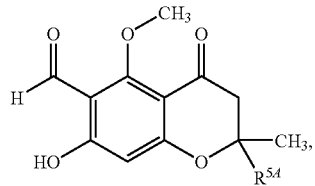
(XX)

in which $R^{5A}$ is as defined above,
then reacting by standard methods to give a compound of the formula (XXI)

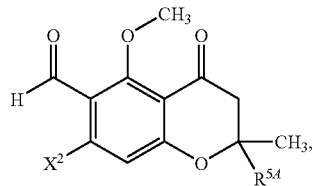
(XXI)

in which $R^{5A}$ is as defined above
and
$X^2$ represents a leaving group, such as tosylate, mesylate or, in particular, triflate,
then coupling this with cyclopentene in the presence of a suitable catalyst and a base to give a compound of the formula (XXII)

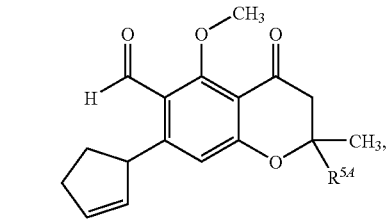
(XXII)

in which $R^{5A}$ is as defined above,
and subsequently hydrogenating in the presence of a suitable catalyst to give the cyclopentane derivative (XXIII)

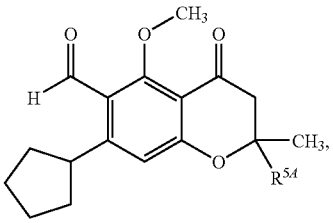
(XXIII)

in which $R^{5A}$ is as defined above
(cf. reaction scheme 1).

Compounds of the formula (XIX) can be obtained via a 1,4-addition of trialkylaluminum compounds or alkyl cuprates to visnagin (5-methoxy-2-methylfuranochromone) (XXIV)

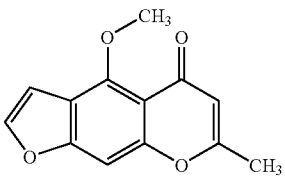
(XXIV)

or via a partial reduction of (XXIV) (cf. reaction scheme 1).

The leaving group $X^2$ used is preferably a triflate group (trifluoromethylsulfonate). To introduce this group in process step (XX)→(XXI), the phenol derivative (XX) is reacted in an inert solvent, such as dichloromethane or dimethylformamide, with trifluoromethanesulfonic anhydride or, preferably, with N,N-bis(trifluoromethanesulfonyl)aniline in the presence of a base, such as potassium carbonate, pyridine, 2,6-lutidine, 4-N,N-dimethylaminopyridine (DMAP), triethylamine or N,N-diisopropylethylamine.

Inert solvents for the process step (XXI)→(XXII) are, for example, ethers, such as diethyl ether, diisopropyl ether, methyl tert-butyl ether, dioxane, tetrahydrofuran, glycol dimethyl ether or diethylene glycol dimethyl ether, hydrocarbons, such as benzene, toluene, xylene, hexane, cyclohexane or mineral oil fractions, or other solvents, such as dimethylformamide, dimethyl sulfoxide, N,N'-dimethylpropylene urea (DMPU), N-methylpyrrolidone (NMP) or acetonitrile. It is also possible to use mixtures of the solvents mentioned. Preference is given to using acetonitrile.

Suitable catalysts for the process step (XXI)→(XXII) ["Heck coupling"] are, for example, palladium(II) acetate or palladium(II) trifluoroacetate, in combination with triphenylphosphine or tritolylphosphine, or bis(dibenzylideneacetone)palladium(0). The reaction is carried out with addition of a base such as potassium carbonate or N,N-diisopropylethylamine.

The reaction is generally carried out in a temperature range of from +20° C. to +120° C., preferably at from +40° C. to +100° C.

All reactions described above can be carried out at atmospheric, elevated or at reduced pressure (for example from 0.5 to 5 bar). In general, the reactions are in each case carried out at atmospheric pressure.

The compounds of the formulae (III), (VII), (XVa), (XVb), (XVII), (XVIII) and (XXIV) are commercially available, known from the literature or can be prepared analogously to processes known from the literature.

The preparation of the compounds according to the invention can be illustrated by synthesis schemes 1-8 below:

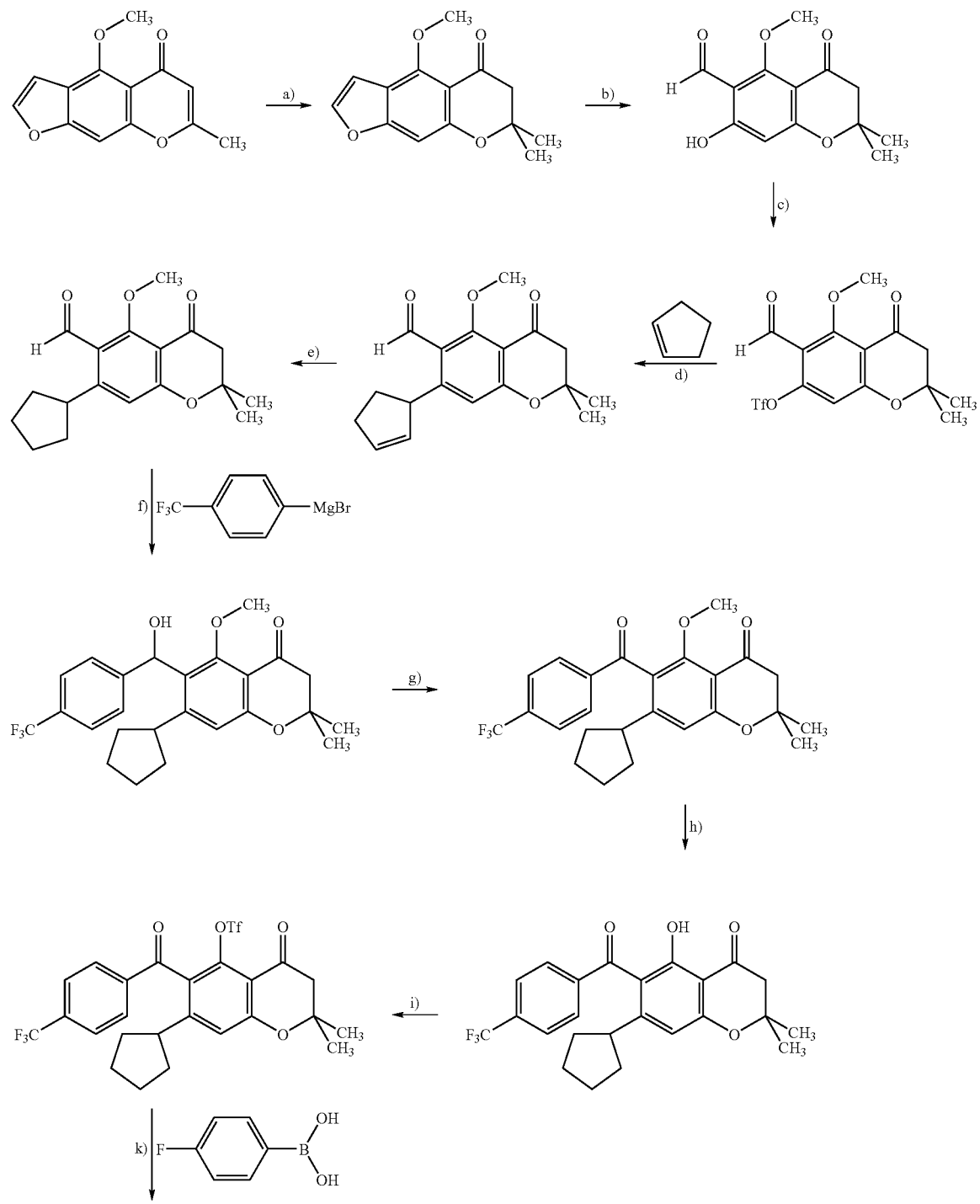

Scheme 1

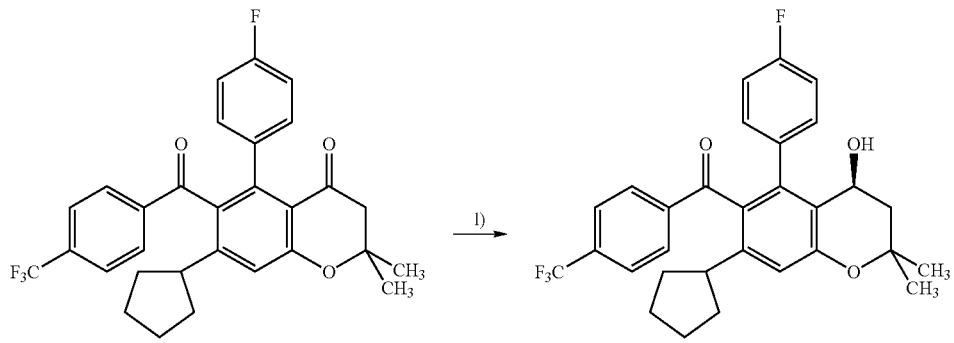
[a]: AlMe₃, Ni(acac)₂, THF/Et₂O, -20° C. → 0° C.; b): O₃, CH₂Cl₂, -78° C.; c): PhNTf₂, Et₃N, CH₂Cl₂, 0° C. → RT; d): Pd(OAc)₂, P(o-Tol)₃, i-Pr₂EtN, CH₃CN, 45° C.; e): H₂, 10% Pd/C, EtOAc, RT; f): THF, -78° C. → -20° C.; g): MnO₂, CH₂Cl₂, RT; h): BBr₃, CH₂Cl₂, -78° C.; i): PhNTf₂, K₂CO₃, DMF, diethylaniline complex, THF, 0° C. → RT].
Scheme 2
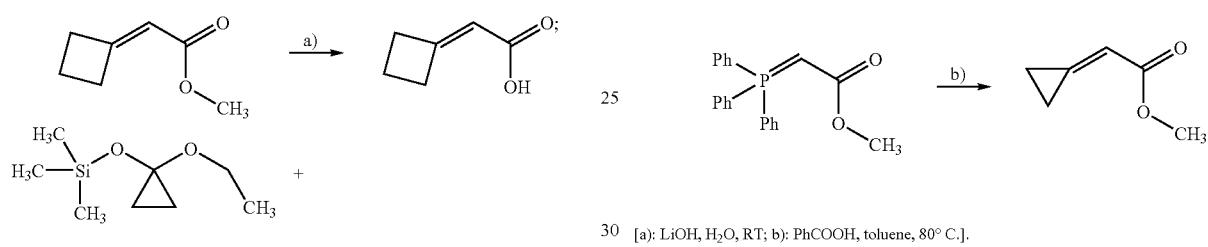
[a]: LiOH, H₂O, RT; b): PhCOOH, toluene, 80° C.].
Scheme 3
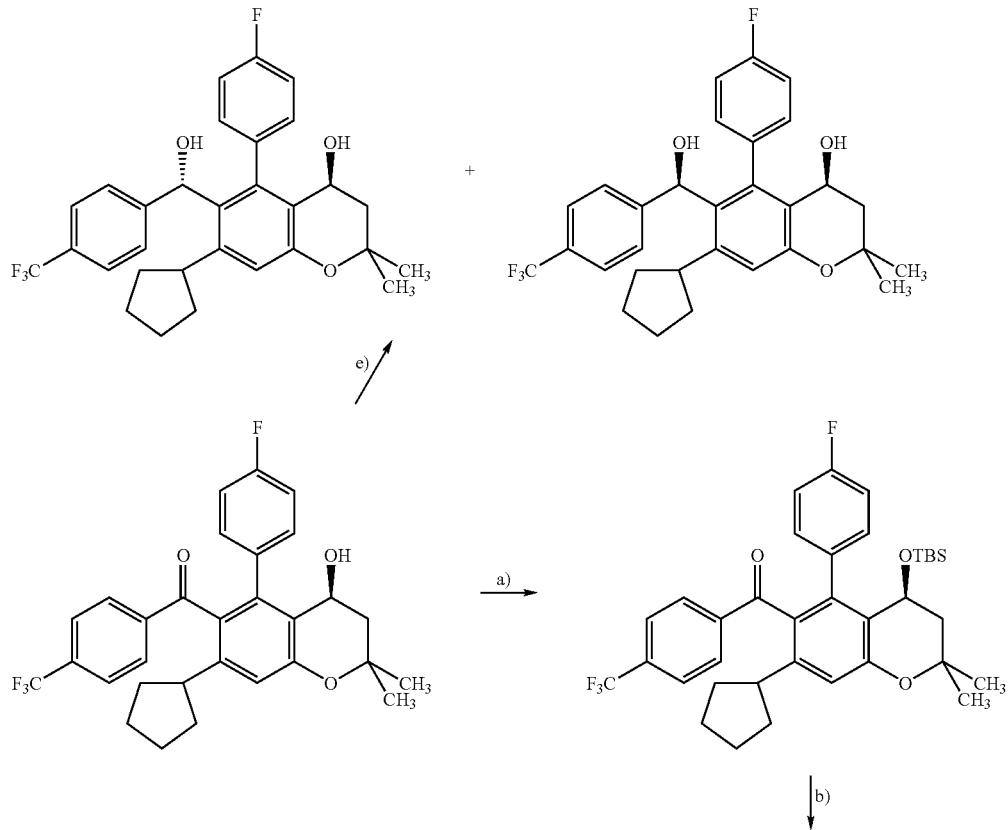

-continued
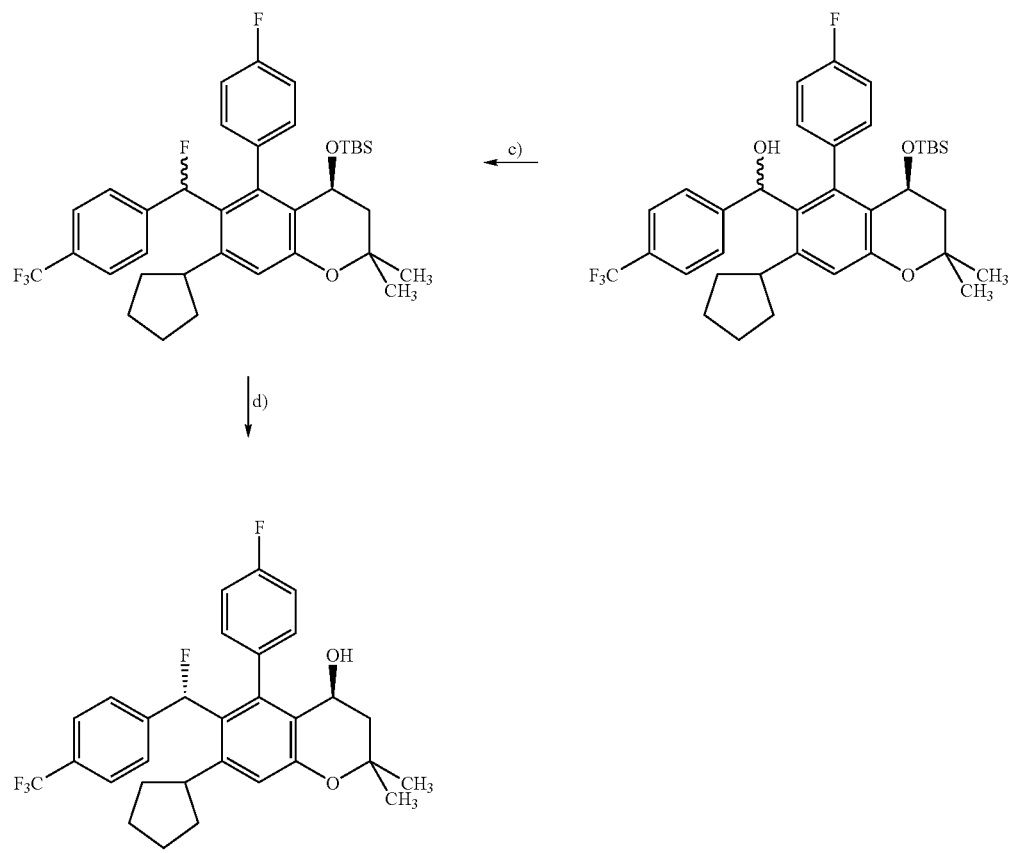
[a]: TBSOTf, lutidine, toluene, -20° C. → 0° C.; b): DIBAL-H, toluene, -78° C.; c): DAST, CH₂Cl₂, RT; d): TBAF, THF, RT; e): DIBAL-H, toluene, -78° C.].
Scheme 4
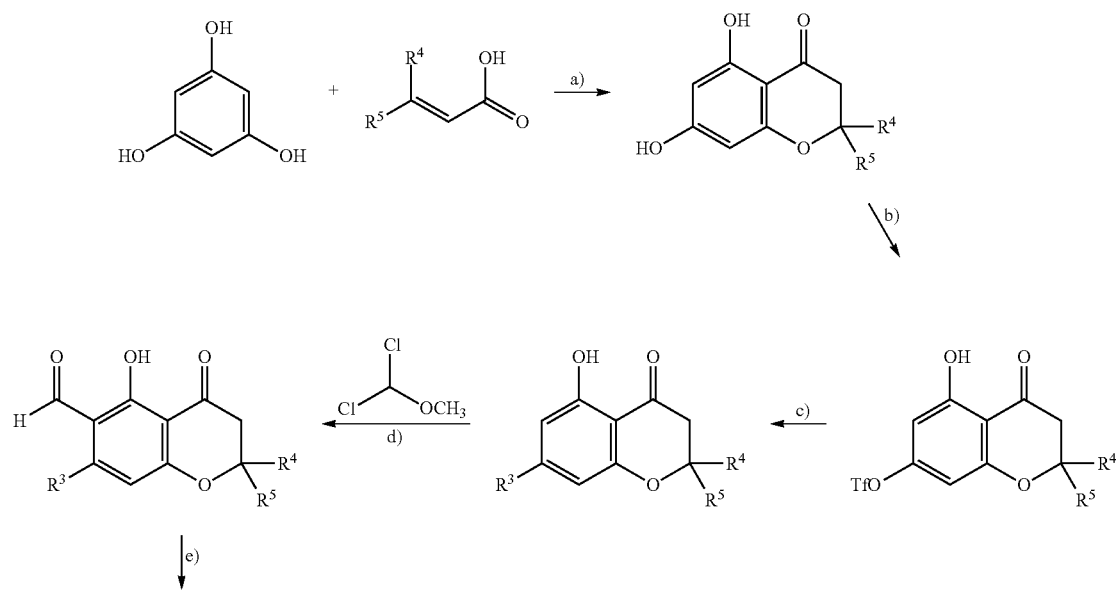

-continued
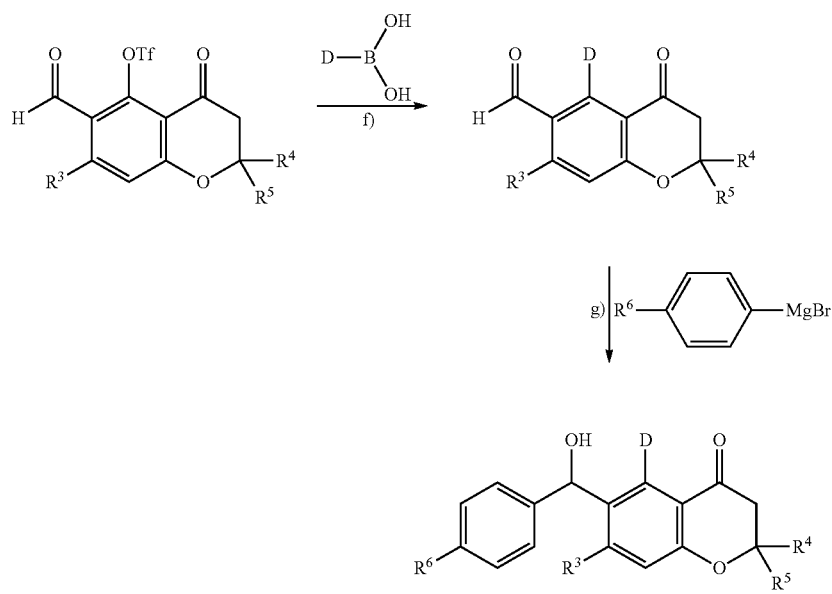
[a]: BF$_3$ x Et$_2$O, 70° C.; b): PhNTf$_2$, K$_2$CO$_3$, DMF, -20° C.; c): (R$^3$)$_2$Zn or R$^3$ZnBr, PdCl$_2$(dppf), LiCl, DMF, 0° C.; d): TiCl$_4$, -70° C. → RT; e): PhNTf$_2$, K$_2$CO$_3$, DMF, -20° C. → RT; f) Pd(PPh$_3$)$_4$, K$_3$PO$_4$, dioxane, 100° C.; g): THF, -78° C. → RT].
Scheme 5
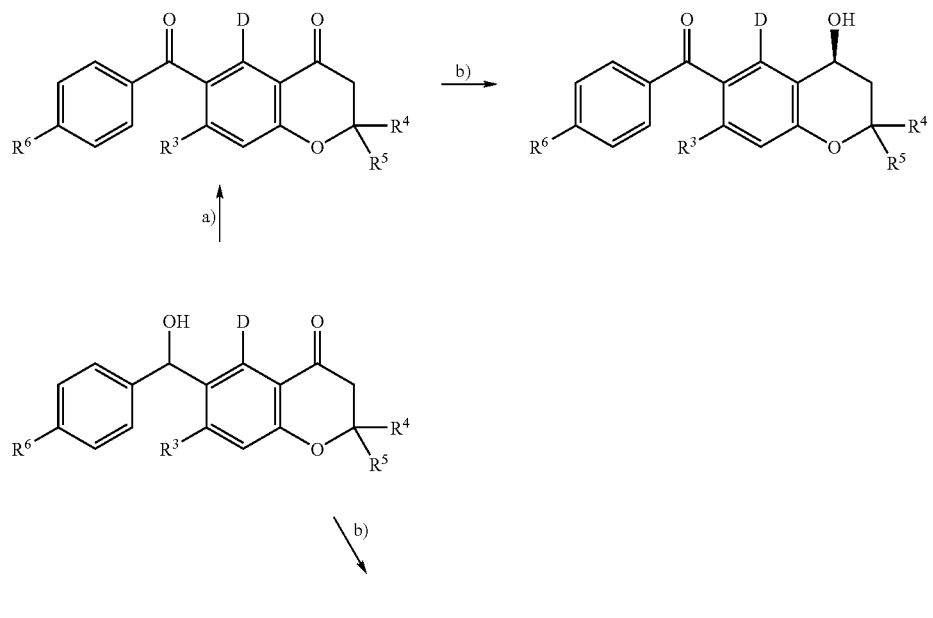
[a]: Dess-Martin periodinane, pyridine, CH$_2$Cl$_2$, -30° C. → 0° C.; b): (1R,2S)-aminoindanol, borane/N,N-diethylaniline complex, THF, RT].

Scheme 6
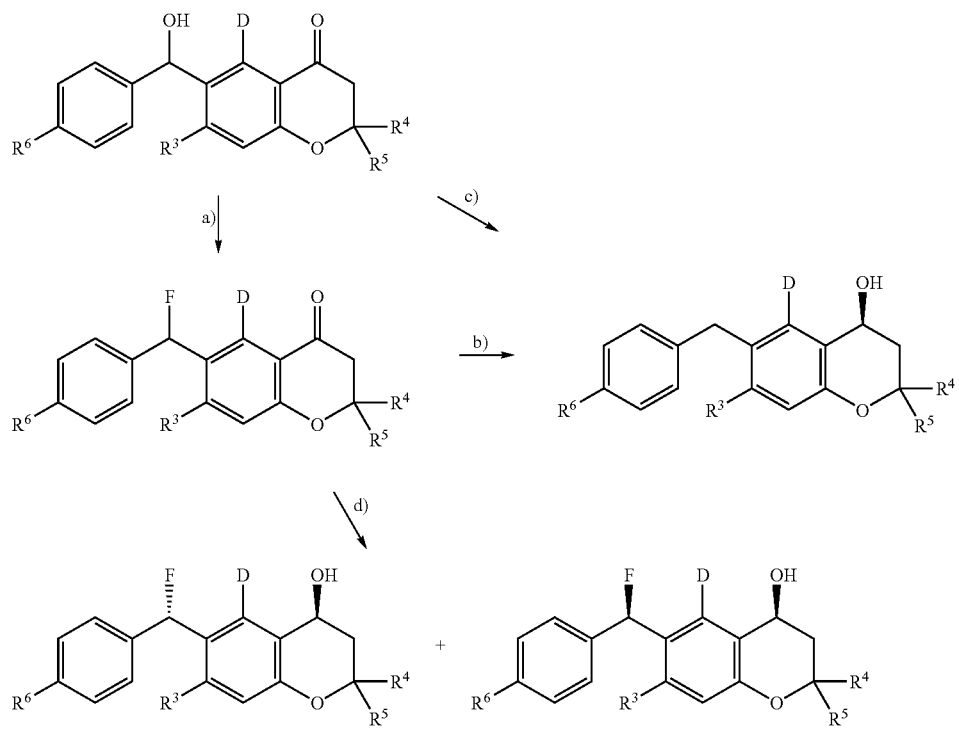
[a]: DAST, toluene, -78° C. → -60° C.; b): (1R,2S)-aminoindanol, borane/N,N-diethylaniline complex, THF, RT (for R6 = OCF3 or CMe3); c): 1. SOCl2, Et3N, THF, RT; 2. (1R,2S)-aminoindanol, borane/N,N-diethylaniline complex, THF, RT; 3. LiAlH4, THF, RT; d): (1R,2S)-aminoindanol, borane/N,N-diethylaniline complex, THF, RT (for R6 = CF3)].
Scheme 7
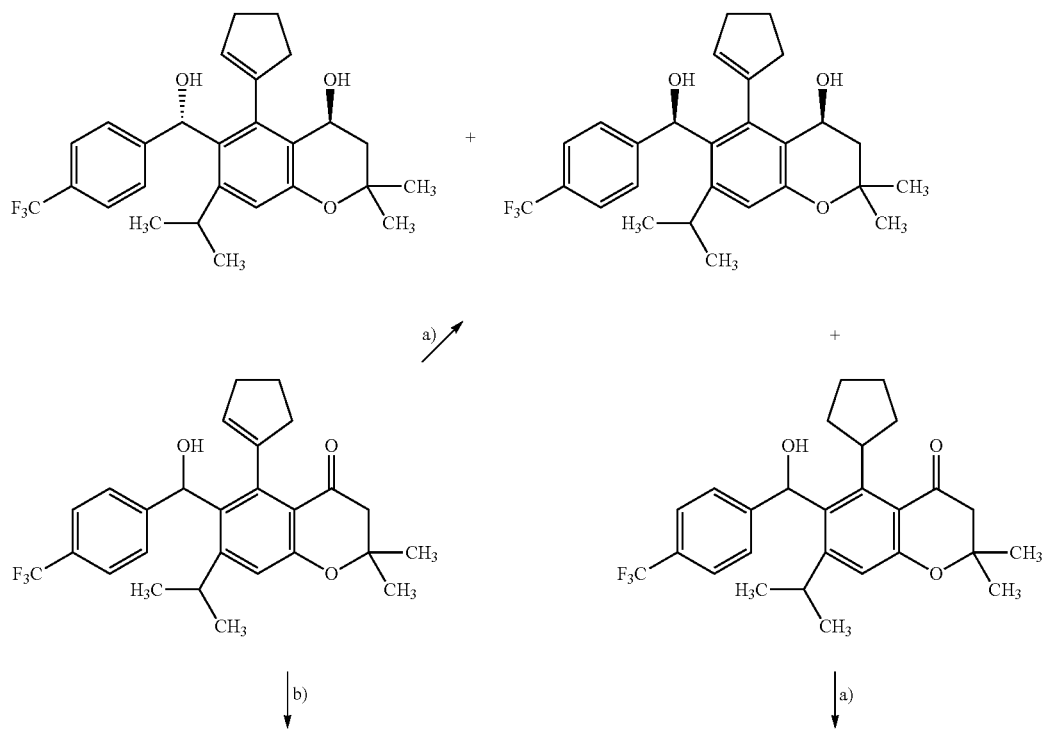

-continued
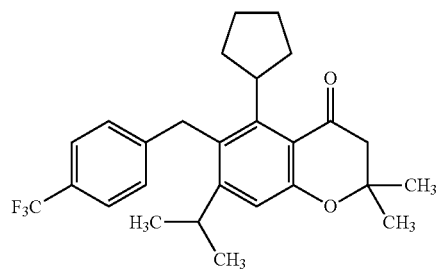
25
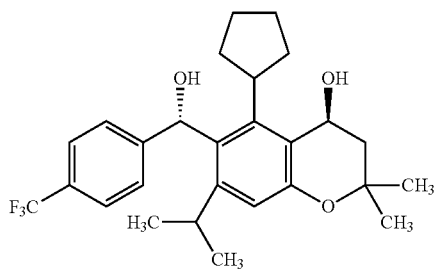
26
a)
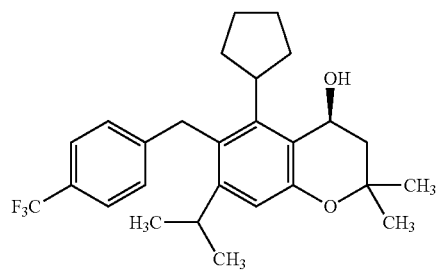
+
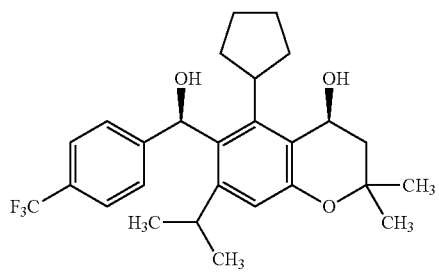
[a]: (1R,2S)-aminoindanol, borane/N,N-diethylaniline complex, THF, RT; b): H₂, Pd/C, EtOH].
Scheme 8
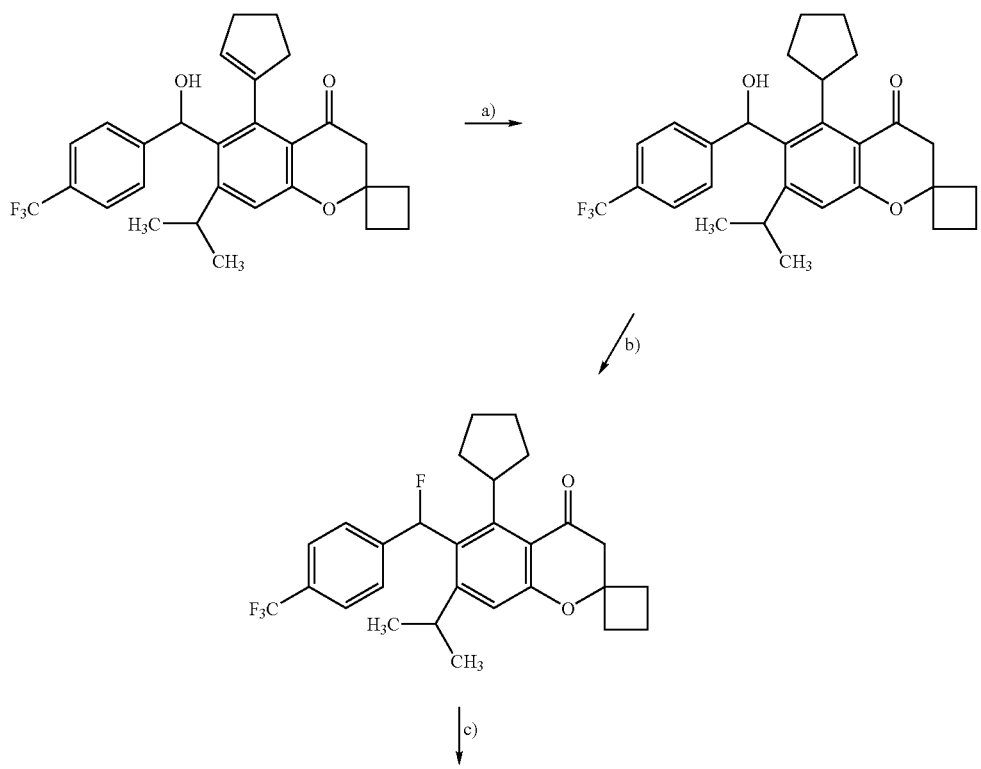

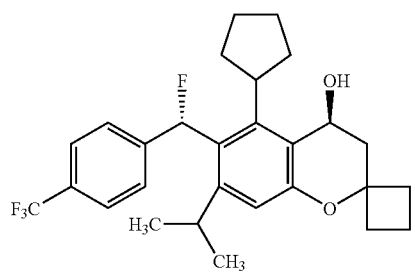 + 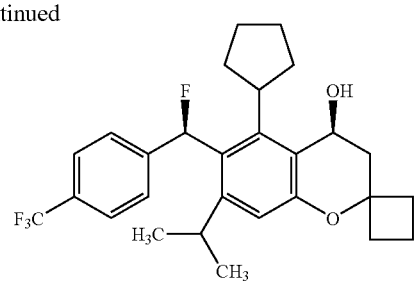

[a): H₂, 5% Rh cat., EtOH, RT; b): DAST, CH₂Cl₂, -78° C. → -15° C.; c): (1R,2S)-aminoindanol, borane/N,N-diethylaniline complex, THF, RT].

The compounds according to the invention have useful pharmacological properties and can be used for the prevention and treatment of disorders in humans and animals.

The compounds according to the invention open up a further treatment alternative and represent an advance of pharmacy. In comparison to the substances which have been employed previously or are known from the prior art, the compounds according to the invention have an improved spectrum of action. They are distinguished by great specificity and good tolerability. A particular advantage of the compounds according to the invention is their high activity in human plasma. At the same time, as a further advantage, they have a reduced tendency to deposit themselves in fatty tissue.

The compounds according to the invention are highly effective inhibitors of the cholesterol ester transfer protein (CETP) and stimulate reverse cholesterol transport. They elevate the HDL cholesterol concentration in the blood. The compounds according to the invention are particularly suitable for the treatment and for the primary or secondary prevention of coronary heart disease, for example myocardial infarction, angina pectoris, cardiac insufficiency, heart failure, pulmonary hypertension and ischemia-related heart damage (acute coronary syndrome). In addition, the compounds according to the invention can be used for the treatment and prevention of arteriosclerosis, peripheral vascular disorders, restenosis, stroke and Alzheimer's disease. Moreover, the compounds according to the invention can also be used for the treatment and prevention of hypolipoproteinemias, dyslipidemias, hypertriglyceridemias, hyperlipidemias, hypercholesterolemias, adiposity, obesity, pancreatitis, insulin-dependent and non-insulin-dependent diabetes, diabetic sequelae such as, for example, retinopathy, nephropathy and neuropathy, of combined hyperlipidemias and of the metabolic syndrome.

The pharmacological action of the compounds according to the invention can be determined using the CETP inhibition tests described below.

The present invention furthermore provides the use of the compounds according to the invention for the treatment and/or prevention of disorders, in particular the disorders mentioned above.

The present invention furthermore provides the use of the compounds according to the invention for preparing a medicament for the treatment and/or prevention of disorders, in particular the disorders mentioned above.

The present invention furthermore provides a method for the treatment and/or prevention of disorders, in particular the disorders mentioned above, using an effective amount of at least one of the compounds according to the invention.

The compounds according to the invention can be employed on their own or, if required, in combination with other active compounds. The present invention furthermore provides medicaments comprising at least one of the compounds according to the invention and one or more further active compounds, for the treatment and/or prevention of the disorders mentioned above. Active compounds suitable for combinations are, by way of example and by way of preference:
 antidiabetics,
 substances having antithrombotic action,
 hypotensive substances,
 lipid metabolism-modifying substances,
 anti-inflammatory substances,
 substances which stabilize arteriosclerotic plaque.

The compounds according to the invention can preferably be combined with one or more
 active compounds from the class of the antidiabetics mentioned in the Roten Liste [red list] 2002/II, chapter 12,
 agents having antithrombotic action, by way of example and by way of preference from the group of the platelet aggregation inhibitors or the anticoagulants,
 hypotensive agents, by way of example and by way of preference from the group of the calcium antagonists, angiotensin AII antagonists, ACE inhibitors, renin inhibitors, beta blockers, alpha blockers, phosphodiesterase inhibitors, stimulators of soluble guanylate cyclase, cGMP enhancers, adenosine receptor agonists, aldosterone antagonists, mineralocorticoid receptor antagonists, endothelin antagonists, ECE inhibitors, vasopeptidase inhibitors and diuretics, and/or
 active compounds which modify lipid metabolism, by way of example and by way of preference from the group of the thyroid receptor agonists, the cholesterol synthesis inhibitors, such as HMG-CoA reductase inhibitors, squalene synthase inhibitors, squalene epoxidase inhibitors or oxidosqualene cyclase inhibitors, the ACAT inhibitors, MTP inhibitors, PPAR agonists, fibrates, lipase inhibitors, cholesterol absorption inhibitors, bile acid reabsorption inhibitors, polymeric bile acid adsorbers, lipoprotein(a) antagonists, RXR modulators, FXR modulators, LXR modulators, ATP citrate lyase inhibitors, cannabinoid receptor 1 antagonists, leptin receptor agonists, bombesin receptor agonists, histamine receptor agonists and the antioxidants/radical scavengers.

Antidiabetics are to be understood as meaning, by way of example and by way of preference, insulin and insulin derivatives, and also orally effective compounds with hypoglycemic action.

Here, insulin and insulin derivatives include both insulins of animal, human or biotechnological origin and mixtures thereof.

The orally effective compounds with hypoglycemic action include, by way of example and by way of preference, sulfonylureas, biguanidines, meglitinide derivatives, oxadiazolidinones, thiazolidinediones, glucosidase inhibitors, glucagon antagonists, GLP-1 agonists, DPPIV inhibitors, ghrelin receptor antagonists, CCK 1 receptor agonists, leptin receptor agonists, insulin sensitizers, inhibitors of liver enzymes involved in the stimulation of gluconeogenesis and/or glycogenolysis, modulators of glucose uptake and potassium channel openers, such as, for example, those disclosed in WO 97/26265 and WO 99/03861.

In a preferred embodiment of the invention, the compounds according to the invention are administered in combination with insulin.

In a preferred embodiment of the invention, the compounds according to the invention are administered in combination with a sulfonylurea, such as, by way of example and by way of preference, tolbutamide, glibenclamide, glimepiride, glipizide or gliclazide.

In a preferred embodiment of the invention, the compounds according to the invention are administered in combination with a biguanide, such as, by way of example and by way of preference, metformin.

In a preferred embodiment of the invention, the compounds according to the invention are administered in combination with a meglitinide derivative, such as, by way of example and by way of preference, repaglinide or nateglinide.

In a preferred embodiment of the invention, the compounds according to the invention are administered in combination with a PPARgamma agonist, for example from the class of the thiazolidinediones, such as, by way of example and by way of preference, pioglitazone or rosiglitazone.

In a preferred embodiment of the invention, the compounds according to the invention are administered in combination with a mixed PPARalpha/gamma agonist, such as, by way of example and by way of preference, GI-262570 (farglitazar), GW 2331, GW 409544, AVE 8042, AVE 8134, AVE 0847, MK-0767 (KRP-297) or AZ-242.

In a preferred embodiment of the invention, the compounds according to the invention are administered in combination with a glucosidase inhibitor, such as, by way of example and by way of preference, acarbose, adiposin, voglibose or miglitol.

In a preferred embodiment of the invention, the compounds according to the invention are administered in combination with a DPPIV inhibitor, such as, by way of example and by way of preference, vildagliptin or sitaglipitin.

Agents with antithrombotic action are to be understood as meaning, preferably, compounds from the group of the platelet aggregation inhibitors, such as, by way of example and by way of preference, aspirin, clopidogrel, ticlopidine or dipyridamole, or of the anticoagulants.

In a preferred embodiment of the invention, the compounds according to the invention are administered in combination with a thrombin inhibitor, such as, by way of example and by way of preference, ximelagatran, melagatran, dabigatran, tanogitran, bivalirudin or clexane.

In a preferred embodiment of the invention, the compounds according to the invention are administered in combination with a GPIIb/IIIa antagonist, such as, by way of example and by way of preference, tirofiban or abciximab.

In a preferred embodiment of the invention, the compounds according to the invention are administered in combination with a factor Xa inhibitor, such as, by way of example and by way of preference, apixaban, razaxaban, otamixaban or rivaroxaban.

In a preferred embodiment of the invention, the compounds according to the invention are administered in combination with heparin or a low-molecular-weight (LMW) heparin derivative.

In a preferred embodiment of the invention, the compounds according to the invention are administered in combination with a vitamin K antagonist, such as, by way of example and by way of preference, coumarin.

Hypotensive agents are to be understood as meaning, by way of example and by way of preference, compounds from the group of the calcium antagonists, such as, by way of example and by way of preference, the compounds nifedipine, amlodipine, nitrendipine, nisoldipine, verapamil or diltiazem, of the angiotensin AII antagonists, ACE inhibitors, renin inhibitors, beta blockers, alpha blockers and the diuretics.

In a preferred embodiment of the invention, the compounds according to the invention are administered in combination with reserpine, minoxidil, diazoxide, dihydralazine, hydralazine and nitrous oxide-releasing substances, such as, by way of example and by way of preference, glycerol nitrate or sodium nitroprusside.

In a preferred embodiment of the invention, the compounds according to the invention are administered in combination with an angiotensin AII antagonist, such as, by way of example and by way of preference, losartan, valsartan, candesartan, telmisartan, embusartan, irbesartan, olmesartan, tasosartan or saprisartan.

In a preferred embodiment of the invention, the compounds according to the invention are administered in combination with an ACE inhibitor, such as, by way of example and by way of preference, enalapril, captopril, ramipril, delapril, fosinopril, quinopril, perindopril or trandolapril.

In a preferred embodiment of the invention, the compounds according to the invention are administered in combination with a renin inhibitor, such as, by way of example and by way of preference, aliskiren.

In a preferred embodiment of the invention, the compounds according to the invention are administered in combination with a beta blocker, such as, by way of example and by way of preference, propranolol or atenolol.

In a preferred embodiment of the invention, the compounds according to the invention are administered in combination with a diuretic, such as, by way of example and by way of preference, furosemide.

Lipid metabolism-modifying agents are to be understood as meaning, by way of example and by way of preference, compounds from the group of the thyroid receptor agonists, the cholesterol synthesis inhibitors, such as HMG-CoA reductase inhibitors or squalene synthesis inhibitors, the ACAT inhibitors, MTP inhibitors, PPAR agonists, fibrates, cholesterol absorption inhibitors, bile acid reabsorption inhibitors, lipase inhibitors, polymeric bile acid adsorbers, lipoprotein(a) antagonists and the cannabinoid receptor 1 antagonists.

In a preferred embodiment of the invention, the compounds according to the invention are administered in combination with a thyroid receptor agonist, such as, by way of example and by way of preference, D-thyroxine, 3,5,3'-triiodothyronine (T3), CGS 23425 or axitirome (CGS 26214).

In a preferred embodiment of the invention, the compounds according to the invention are administered in combination with a squalene synthesis inhibitor, such as, by way of example and by way of preference, BMS-188494 or TAK 475.

In a preferred embodiment of the invention, the compounds according to the invention are administered in combination with an ACAT inhibitor, such as, by way of example and by way of preference, avasimibe, eflucimibe or CS-505.

In a preferred embodiment of the invention, the compounds according to the invention are administered in combination with a cholesterol absorption inhibitor, such as, by way of example and by way of preference, ezetimibe, tiqueside or pamaqueside.

In a preferred embodiment of the invention, the compounds according to the invention are administered in combination with a bile acid reabsorbtion inhibitor, such as, by way of example and by way of preference, barixibat, AZD 7508, SC 435, SC 635, S-8921, 264W94 or HM 1453.

In a preferred embodiment of the invention, the compounds according to the invention are administered in combination with an MTP inhibitor, such as, by way of example and by way of preference, implitapide, BMS-201038 or R-103757.

In a preferred embodiment of the invention, the compounds according to the invention are administered in combination with a PPARalpha agonist, such as, for example, the fibrates fenofibrate, clofibrate, bezafibrate, ciprofibrate or gemfibrozil, or such as, by way of example and by way of preference, GW 9578, GW 7647, LY-518674 or NS-220.

In a preferred embodiment of the invention, the compounds according to the invention are administered in combination with a PPARdelta agonist, such as, by way of example and by way of preference, GW 501516.

In a preferred embodiment of the invention, the compounds according to the invention are administered in combination with a mixed PPARalpha/gamma agonist, such as, by way of example and by way of preference, GI-262570 (farglitazar), GW 2331, GW 409544, AVE 8042, AVE 8134, AVE 0847, MK-0767 (KRP-297) or AZ-242.

In a preferred embodiment of the invention, the compounds according to the invention are administered in combination with a mixed PPARalpha/gamma/delta agonist, such as, by way of example and by way of preference, MCC-555.

In a preferred embodiment of the invention, the compounds according to the invention are administered in combination with a lipase inhibitor from the group of the endothelial lipase inhibitors, the pancreatic lipase inhibitors, the gastric lipase inhibitors, the hormone-sensitive lipase inhibitors or the hepatic lipase inhibitors.

In a particularly preferred embodiment of the invention, the compounds according to the invention are administered in combination with an inhibitor of pancreatic lipase, preferably from the class of the lipstatins, such as, by way of example, orlistat.

In a preferred embodiment of the invention, the compounds according to the invention are administered in combination with a polymeric bile acid adsorber, such as, by way of example and by way of preference, cholestyramine, colestipol, colesolvam, CholestaGel or colestimide.

In a preferred embodiment of the invention, the compounds according to the invention are administered in combination with a lipoprotein(a) antagonist, such as, by way of example and by way of preference, gemcabene calcium (CI-1027) or nicotinic acid.

In a preferred embodiment of the invention, the compounds according to the invention are administered in combination with a cannabinoid receptor 1 antagonist, such as, by way of example and by way of preference, rimonabant.

In a preferred embodiment of the invention, the compounds according to the invention are administered in combination with an antagonist of the niacin receptor, such as, by way of example and by way of preference, niaspan, acipimox or niceritrol.

In a preferred embodiment of the invention, the compounds according to the invention are administered in combination with an antioxidant, such as, by way of example and by way of preference, probucol, AGI 1067 or Bo 653.

In a preferred embodiment of the invention, the compounds according to the invention are administered in combination with an LDL receptor inducer, such as, by way of example, lifibrol.

In a preferred embodiment of the invention, the compounds according to the invention are administered in combination with an HMG-CoA reductase inhibitor from the class of the statins, such as, by way of example and by way of preference, lovastatin, simvastatin, pravastatin, fluvastatin, atorvastatin, rosuvastatin, cerivastatin or pitavastatin.

The present invention also provides combinations of the compounds according to the invention with substances which reduce the gene expression of HMG-CoA reductase. Such substances may, for example, be inhibitors of HMG-CoA reductase transcription or HMG-CoA reductase translation. Inhibition of HMG-CoA reductase gene expression may be effected, for example, by inhibiting S1P (Site-1) protease, or by lowering the SREBP (sterol receptor binding protein) concentration.

The present invention also provides combinations of the compounds according to the invention with substances which may have anti-inflammatory action and/or stabilize arteriosclerotic plaque. Such substances may, for example, be active compounds from the class of the NSAIDs, the $Lp-PLA_2$ antagonists or the chemokine receptor antagonists, such as, by way of example, IL-8 receptor antagonists or MCP-1 antagonists.

In a preferred embodiment of the invention, the compounds according to the invention are administered in combination with an $Lp-PLA_2$ antagonist, such as, by way of example and by way of preference, darapladib or goxalapladib.

The active compound combinations according to the invention have useful pharmacological properties and can be used for the prophylaxis and treatment of disorders.

The active compound combinations according to the invention are particularly suitable for the treatment and for primary or secondary prevention of coronary heart disease, for example myocardial infarction, angina pectoris, cardiac insufficiency, heart failure, pulmonary hypertension and ischemia-related heart damage (acute coronary syndrome). In addition, the active compound combinations according to the invention can be used for the treatment and prevention of arteriosclerosis, peripheral vascular disorders, restenosis, stroke and Alzheimer's disease. Moreover, the active compound combinations mentioned can also be used for the treatment and prevention of hypolipoproteinemias, dyslipidemias, hypertriglyceridemias, hyperlipidemias, hypercholesterolemias, adiposity, obesity, pancreatitis, insulin-dependent and non-insulin-dependent diabetes, diabetic sequelae such as, for example, retinopathy, nephropathy and neuropathy, of combined hyperlipidemias and of the metabolic syndrome. Furthermore, the active compound combinations according to the invention are suitable for treating hypertension and inflammatory disorders.

The present invention furthermore provides medicaments comprising at least one compound according to the invention, usually together with one or more inert nontoxic pharmaceutically suitable auxiliaries, and their use for the purposes mentioned above.

The compounds according to the invention can act systemically and/or locally. For this purpose, they can be administered in the suitable manner, such as, for example, orally, parenterally, pulmonarily, nasally, sublingually, lingually, buccally, rectally, dermally, transdermally, conjunctivally, otically or as an implant or stent.

For these administration routes, the compounds according to the invention can be administered in suitable administration forms.

Suitable for oral administration are administration forms which work according to the prior art, deliver the compounds according to the invention rapidly and/or in modified form and which comprise the compounds according to the invention in crystalline and/or amorphisized and/or dissolved form, such as, for example, tablets (uncoated or coated tablets, for example tablets provided with enteric coatings or coatings which dissolve in a delayed manner or are insoluble and which control the release of the compound according to the invention), tablets which rapidly disintegrate in the oral cavity or films/wafers, films/lyophilizates, capsules (for example hard or soft gelatin capsules), sugar-coated tablets, granules, pellets, powders, emulsions, suspensions, aerosols or solutions.

Parenteral administration can be carried out with avoidance of an absorption step (for example intravenously, intraarterially, intracardially, intraspinally or intralumbarly) or with involvement of an absorption (for example intramuscularly, subcutaneously, intracutaneously, percutaneously or intraperitoneally). Suitable administration forms for parenteral administration are, inter alia, injection and infusion preparations in the form of solutions, suspensions, emulsions, lyophilizates or sterile powders.

Suitable for the other administration routes are, for example, pharmaceutical forms for inhalation (inter alia powder inhalers, nebulizers), nasal drops, solutions or sprays, tablets to be administered lingually, sublingually or buccally, films/wafers or capsules, suppositories, aural and ophthalmic preparations, vaginal capsules, aqueous suspensions (lotions, shaker mixtures), lipophilic suspensions, ointments, creams, transdermal therapeutic systems (for example patches), milk, pastes, foams, dusting powders, implants or stents.

Preference is given to oral or parenteral administration, in particular to oral administration.

The compounds according to the invention can be converted into the administration forms mentioned. This may take place in a manner known per se by mixing with inert nontoxic pharmaceutically suitable auxiliaries. These auxiliaries include, inter alia, carriers (for example microcrystalline cellulose, lactose, mannitol), solvents (for example liquid polyethylene glycols), emulsifiers and dispersants or wetting agents (for example sodium dodecylsulfate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides) and taste and/or odor correctants.

In general, it has been found to be advantageous to administer, in the case of parenteral administration, amounts of from about 0.001 to 1 mg/kg, preferably about 0.01 to 0.5 mg/kg, of body weight to obtain effective results. In the case of oral administration, the dosage is from about 0.01 to 100 mg/kg, preferably about 0.01 to 20 mg/kg and very particularly preferably 0.1 to 10 mg/kg, of body weight.

In spite of this, it may, if appropriate, be necessary to depart from the amounts mentioned, namely depending on the body weight, the administration route, the individual response to the active compound, the type of preparation and the time or interval at which administration takes place. Thus, in some cases, it may be sufficient to manage with less than the above-mentioned minimum amount, while in other cases the upper limit mentioned has to be exceeded. In the case of the administration of relatively large amounts, it may be advisable to divide these into a number of individual doses over the course of the day.

The following exemplary embodiments illustrate the invention. The invention is not limited to the examples.

The percentages in the tests and examples below are, unless indicated otherwise, percentages by weight; parts are parts by weight. Solvent ratios, dilution ratios and stated concentrations of liquid/liquid solutions are in each case based on volume.

A. EXAMPLES

Abbreviations abs. absolute
Ac acetyl
acac acetyl acetonate
analyt. analytic
BSA bovine serum albumin
CE cholesterol ester
CETP cholesterol ester transfer protein
DCI direct chemical ionization (in MS)
d day(s)
DAST diethylaminosulfur trifluoride
de diastereomeric excess
DIBAL-H diisobutylaluminum hydride
DMAP 4-N,N-dimethylaminopyridine
DMF N,N-dimethylformamide
DMP Dess-Martin periodinane reagent
DMSO dimethyl sulfoxide
EDTA ethylenediamine-N,N,N',N'-tetraacetic acid
ee enantiomeric excess
EI electron impact ionization (in MS)
eq. equivalent(s)
ESI electrospray ionization (in MS)
Et ethyl
EtOAc ethyl acetate
GC/MS gas chromatography-coupled mass spectrometry
h hour(s)
HDL high density lipoprotein
HPLC high pressure, high performance liquid chromatography
cat. catalyst
LC/MS liquid chromatography-coupled mass spectrometry
LDL low density lipoprotein
Me methyl
min minute(s)
MS mass spectrometry
MTBE methyl tert-butyl ether
NMR nuclear magnetic resonance spectrometry
PBS phosphate-buffered saline
$PdCl_2$(dppf) bis(diphenylphosphino)ferrocenepalladium(II) chloride
Ph phenyl
Pr propyl
prep. preparative
rac racemic
RT room temperature
$R_t$ retention time (in HPLC)
SPA scintillation proximity assay
TBAF tetra-n-butylammonium fluoride
TBS tert-butyldimethylsilyl
Tf triflate (trifluoromethylsulfonyl)
THF tetrahydrofuran
Tol tolyl
Tris tris(hydroxymethyl)aminomethane
UV ultraviolet spectrometry
v/v volume to volume ratio (of a solution)
w/v weight to volume ratio (of a solution)
LC/MS, GCIMS and HPLC Methods:
Method 1 (prep. HPLC):

Instrument type: Abimed Gilson 305; column: YMC GEL ODS-AQS-5/15 μm, 250 mm×30 mm; mobile phase: gradient acetonitrile/water 50:50→80:20 (15 min)→95:5 (27 min); flow rate: 40 ml/min; UV detection: 210 mm.

Method 2 (prep. HPLC, Chiral):
Column: Chiralpak AD-H, 250 mm×20 mm; mobile phase: isohexane/isopropanol 97:3 (20 min); flow rate: 15 ml/min; temperature: 24° C.; UV detection: 254 nm.

Method 3 (prep. HPLC):
Column: Kromasil 100 C18 5 μm, 250 mm×20 mm; mobile phase: acetonitrile/water 60:40 (9 min); flow rate: 25 ml/min; temperature: 40° C.; UV detection: 280 nm.

Method 4 (analyt. HPLC, chiral):
Instrument type: HP 1100; column: Chiralpak IA, 250 mm×4.6 mm; mobile phase: isopropanol/isohexane 3:97; flow rate: 1.5 ml/min; temperature: 24° C.; UV detection: 254 nm.

Method 5 (analyt. HPLC, chiral):
Instrument type: HP 1100; column: Chiralpak IA, 250 mm×4.6 mm; mobile phase: isopropanol/isohexane 3:97; flow rate: 1 ml/min; temperature: 24° C.; UV detection: 260 nm.

Method 6 (analyt. HPLC, chiral):
Instrument type: HP 1100; column: Chiralpak IA, 250 mm×4.6 mm, mobile phase: isopropanol/isohexane 3:97; flow rate: 2 ml/min; temperature: 24° C.; UV detection: 254 nm.

Method 7 (LC/MS):
MS instrument type: Micromass ZQ; HPLC instrument type: Waters Alliance 2795; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 8 (LC/MS):
Instrument: Micromass Quattro LCZ with HPLC Agilent series 1100; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min 3.0 min/4.5 min 2 ml/min; oven: 50° C.; UV detection: 208-400 nm.

Method 9 (LC/MS):
MS instrument type: Micromass ZQ; HPLC instrument type: HP 1100 series; UV DAD; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 10 (GC/MS):
Instrument: Micromass GCT, GC 6890; column: Restek RTX-35MS, 30 m×250 μm×0.25 μm; constant helium flow rate: 0.88 ml/min; oven: 60° C.; inlet: 250° C.; gradient: 60° C. (maintained for 0.30 min), 50° C./min→120° C., 16° C./min→250° C., 30° C./min→300° C. (maintained for 1.7 min).

Method 11 (analyt. HPLC):
Instrument: HP 1100 with DAD detection; column: Kromasil 100 RP-18, 60 mm×2.1 mm, 3.5 μm; mobile phase A: 5 ml of HClO$_4$ (70% strength)/liter of water, mobile phase B: acetonitrile; gradient: 0 min 2% B→0.5 min 2% B→4.5 min 90% B→6.5 min 90% B→6.7 min 2% B→7.5 min 2% B; flow rate: 0.75 ml/min; temperature: 30° C.; UV detection: 210 nm.

Method 12 (prep. HPLC):
Column: Kromasil C18, 250 mm×20, 25, 30 or 40 mm; mobile phase A: water+1% formic acid, mobile phase B: acetonitrile; gradient: 90-95% A→95% B; flow rate: 10-50 ml/min; room temperature; UV detection: 210-254 nm.

Starting Materials and Intermediates

Example 1A

4-Methoxy-7,7-dimethyl-6,7-dihydro-5H-furo[3,2-g]chromen-5-one

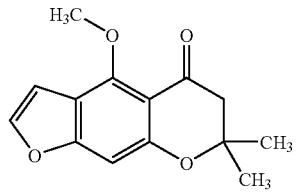

Under argon, 25 g of visnagin (108.6 mmol) are suspended in 500 ml of abs. diethyl ether and 50 ml of abs. tetrahydrofuran, 2.23 g (8.7 mmol) of nickel(II) acetylacetonate are added and the mixture is cooled to −20° C. At this temperature, 81.44 ml (162.9 mmol) of trimethylaluminum (2 M solution in hexane) are added slowly, and the mixture is then slowly warmed to 0° C. and stirring is continued. After one hour, 500 ml of saturated potassium/sodium tartrate solution are added (vigorous evolution of gas), and the mixture is then diluted with 500 ml of ethyl acetate. The organic phase is separated off and the aqueous phase is extracted once more with ethyl acetate. The combined organic phases are washed twice with saturated sodium chloride solution, dried over sodium sulfate, filtered and evaporated to dryness. The residue is chromatographed on silica gel (mobile phase: cyclohexane/ethyl acetate 5:1). This gives 23.28 g (86% of theory) of the title compound.

$^1$H-NMR (300 MHz, CDCl$_3$): δ=7.42 (d, 1H), 6.91 (d, 1H), 6.72 (s, 1H), 4.15 (s, 3H), 2.71 (s, 2H), 1.44 (s, 6H).

MS (ESIpos): m/z=247 (M+H)$^+$, 269 (M+Na)$^+$

HPLC (Method 11): R$_t$=4.30 min.

Example 2A

7-Hydroxy-5-methoxy-2,2-dimethyl-4-oxochroman-6-carbaldehyde

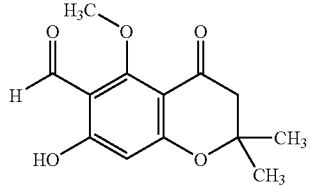

500 mg (2.03 mmol) of 4-methoxy-7,7-dimethyl-6,7-dihydro-5H-furo[3,2-g]chromen-5-one (Example 1A) and 666 mg (2.54 mmol) of triphenylphosphine are initially charged, and 50 ml of dichloromethane are added. The mixture is cooled to −78° C., and ozone is then introduced for about 5 min. Once the color of the solution has turned to blue, excess ozone is flushed out with oxygen. The solution is stirred for another two hours and slowly warmed to room temperature.

The mixture is concentrated and the residue that remains is purified on a silica gel column (mobile phase: cyclohexane/ethyl acetate 5:1) This gives 370 mg (72% of theory) of the title compound.

$^1$H-NMR (300 MHz, CDCl$_3$): δ=12.31 (s, 1H), 10.15 (s, 1H), 6.20 (s, 1H), 4.00 (s, 3H), 2.69 (s, 2H), 1.46 (s, 6H).

MS (ESIpos): m/z=251 (M+H)$^+$.

Example 3A

6-Formyl-5-methoxy-2,2-dimethyl-4-oxo-3,4-dihydro-2H-chromen-7-yl trifluoromethanesulfonate

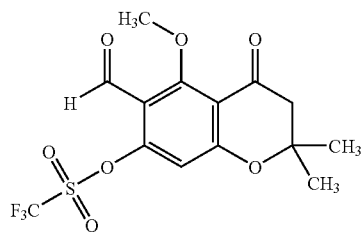

Under argon, 9.1 g (36.36 mmol) of 7-hydroxy-5-methoxy-2,2-dimethyl-4-oxochroman-6-carbaldehyde (Example 2A) and 10.14 ml (72.73 mmol) of triethylamine are dissolved in 180 ml of dichloromethane. The mixture is cooled to 0° C., 15.59 g (43.64 mmol) of N,N-bis(trifluoro-methanesulfonyl)aniline and a spatula tip of DMAP are added, cooling is removed and the mixture is stirred at room temperature for another 4 h. The mixture is then diluted with dichloromethane and washed in each case twice with water and saturated sodium chloride solution. The organic phase is dried over magnesium sulfate, filtered and concentrated to dryness. The residue is chromatographed on silica gel (mobile phase: gradient cyclohexane→cyclohexane/ethyl acetate 10:1→15:1→3:1). This gives 13.65 g (98% of theory) of the title compound.

$^1$H-NMR (300 MHz, CDCl$_3$): δ=10.27 (s, 1H), 6.68 (s, 1H), 4.01 (s, 3H), 2.77 (s, 2H), 1.51 (s, 6H).

MS (ESIpos): m/z=383 (M+H)$^+$.

Example 4A and Example 5A

7-Cyclopent-2-en-1-yl-5-methoxy-2,2-dimethyl-4-oxochroman-6-carbaldehyde (Example 4A) and 7-cyclopent-3-en-1-yl-5-methoxy-2,2-dimethyl-4-oxochroman-6-carbaldehyde (Example 5A)

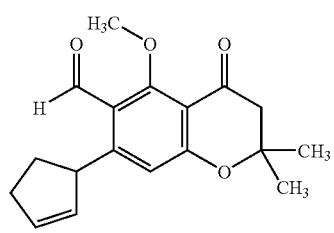

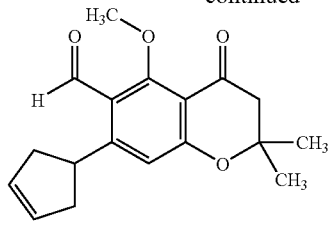

Under argon, 5 g (13.08 mmol) of 6-formyl-5-methoxy-2,2-dimethyl-4-oxo-3,4-dihydro-2H-chromen-7-yl trifluoromethanesulfonate (Example 3A), 46 ml (523.14 mmol) of cyclopentene and 2.73 ml (15.7 mmol) of N,N-diisopropylethylamine are dissolved in 125 ml of acetonitrile. 29.4 mg (0.13 mmol) of palladium(II) acetate and 79.6 mg (0.26 mmol) of tri-o-tolylphosphine are added, argon gas is passed through the solution and the mixture is then heated under reflux (42-45° C.). The mixture is stirred overnight, the same amounts of palladium(II) acetate and tri-o-tolylphosphine are added and stirring under reflux is continued. After a total of 54 h, the mixture is cooled and filtered through a layer of silica gel, and the filter cake is washed thoroughly with ethyl acetate. The solution is diluted with ethyl acetate, then washed twice with saturated sodium chloride solution, dried over sodium sulfate, filtered and concentrated. The residue obtained is chromatographed on silica gel (mobile phase: cyclohexane/ethyl acetate 10:1). This gives 3.35 g (85% of theory) of a mixture of the products 7-cyclopent-2-en-1-yl-5-methoxy-2,2-dimethyl-4-oxochroman-6-carbaldehyde and 7-cyclopent-3-en-1-yl-5-methoxy-2,2-dimethyl-4-oxochroman-6-carbaldehyde in a ratio of 7:3.

$^1$H-NMR (300 MHz, CDCl$_3$): δ=10.46 (s, 1H), 6.72/6.66 (s, 1H), 6.05-5.98 (m, 1H), 5.79-5.63 (m, 1H), 4.88-4.78 and 4.57-4.47 (m, 1H), 3.96/3.95 (s, 3H), 2.92-2.80 and 1.62-1.49 (m, 1H), 2.71 (s, 2H), 2.66-2.53 (m, 1H), 2.47-2.30 (m, 2H), 1.48 (s, 6H).

MS (DCI): m/z=301 (M+H)$^+$, 318 (M+NH$_4$)$^+$.

Example 6A

7-Cyclopentyl-5-methoxy-2,2-dimethyl-4-oxochroman-6-carbaldehyde

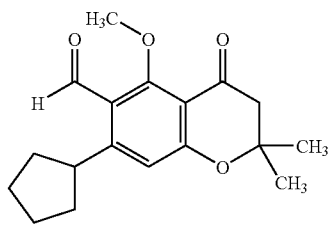

Under argon, 3.3 g (11 mmol) of the mixture of 7-cyclopent-2-en-1-yl-5-methoxy-2,2-dimethyl-4-oxochroman-6-carbaldehyde and 7-cyclopent-3-en-1-yl-5-methoxy-2,2-dimethyl-4-oxochroman-6-carbaldehyde (Example 4A/5A) are dissolved in 200 ml of ethyl acetate, 500 mg of palladium-on-carbon (10%) are added and hydrogen gas is charged at room temperature under atmospheric pressure. After one hour, the mixture is filtered through a layer of silica gel, the filter cake is washed thoroughly with ethyl acetate and the filtrate is concentrated. This gives 3.3 g (99% of theory) of the title compound.

¹H-NMR (400 MHz, CDCl₃): δ=10.42 (s, 1H), 6.78 (s, 1H), 4.04 (heptet, 1H), 3.92 (s, 3H), 2.71 (s, 2H), 2.12-2.03 (m, 2H), 1.83-1.68 (m, 4H), 1.57-1.43 (m, 8H).
MS (DCI): m/z=303 (M+H)⁺, 320 (M+NH₄)⁺.

Example 7A

7-Cyclopentyl-6-{hydroxy[4-(trifluoromethyl)phenyl]methyl}-5-methoxy-2,2-dimethyl-2,3-dihydro-4H-chromen-4-one

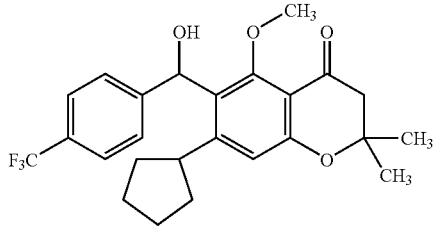

Under argon, 3.7 g (12.24 mmol) of 7-cyclopentyl-5-methoxy-2,2-dimethyl-4-oxochroman-6-carbaldehyde (Example 6A) are suspended in 150 ml of tetrahydrofuran and cooled to −78° C. 29.4 ml (14.68 mmol) of a freshly prepared 0.5 M solution of bromo[4-(trifluoro-methyl)phenyl]magnesium in tetrahydrofuran are added slowly. The mixture is then warmed to −20° C. and stirred at this temperature for 30 min. At −20° C., another 12.3 ml (6.15 mmol) of the above Grignard solution are added, and the mixture is stirred for a further 45 min. The mixture is then hydrolyzed using 5% strength sodium bicarbonate solution and then extracted repeatedly with ethyl acetate. The combined organic phases are washed twice with saturated sodium chloride solution, dried over sodium sulfate, filtered and concentrated. The crude product is chromatographed on silica gel (mobile phase: cyclohexane/ethyl acetate 20:1→2:1). This gives 2.35 g (43% of theory) of the title compound.

¹H-NMR (400 MHz, CDCl₃): δ=7.59 (d, 2H), 7.44 (d, 2H), 6.74 (s, 1H), 6.16 (d, 1H), 3.72 (d, 1H), 3.27-3.16 (m, 4H), 2.72-2.61 (m, 2H), 2.06-1.95 (m, 1H), 1.91-1.55 (m, 7H), 1.48 (s, 3H), 1.47 (s, 3H).
MS (DCI): m/z=449 (M+H)⁺, 466 (M+NH₄)⁺.

Example 8A

7-Cyclopentyl-5-methoxy-2,2-dimethyl-6-[4-(trifluoromethyl)benzoyl]-2,3-dihydro-4H-chromen-4-one

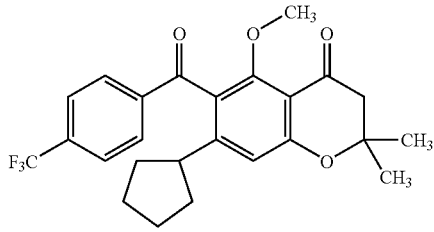

100 mg (0.22 mmol) of 7-cyclopentyl-6-{hydroxy[4-(trifluoromethyl)phenyl]methyl}-5-methoxy-2,2-dimethyl-2,3-dihydro-4H-chromen-4-one (Example 7A) are dissolved in 5 ml of dichloromethane, 194 mg (2.23 mmol) of manganese (IV) oxide are added and the mixture is stirred at room temperature overnight. The mixture is filtered through a layer of silica gel, the filter cake is washed thoroughly with ethyl acetate and the filtrate is concentrated to dryness. The crude product is chromatographed on silica gel (mobile phase: cyclohexane/ethyl acetate 10:1). This gives 82.5 mg (83% of theory) of the title compound.

¹H-NMR (400 MHz, CDCl₃): δ=7.93 (d, 2H), 7.70 (d, 2H), 6.78 (s, 1H), 3.64 (s, 3H), 2.78-2.68 (m, 3H), 1.92-1.81 (m, 2H), 1.79-1.70 (m, 2H), 1.62-1.50 (m, 4H), 1.49 (s, 6H).
MS (DCI): m/z=447 (M+H)⁺.

Example 9A

7-Cyclopentyl-5-hydroxy-2,2-dimethyl-6-[4-(trifluoromethyl)benzoyl]-2,3-dihydro-4H-chromen-4-one

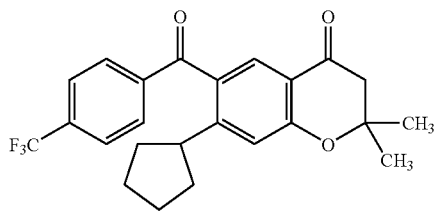

Under argon, 3.10 g (6.94 mmol) of 7-cyclopentyl-5-methoxy-2,2-dimethyl-6-[4-(trifluoro-methyl)benzoyl]-2,3-dihydro-4H-chromen-4-one (Example 8A) are dissolved in 30 ml of abs. dichloromethane. The mixture is cooled to −78° C., 6.25 ml (6.25 mmol) of boron tribromide (1 M in dichloromethane) are added and the yellowish solution is stirred at −78° C. After 1.5 h, another 6.25 ml (6.25 mmol) of boron tribromide (1 M in dichloromethane) are added, and stirring of the mixture is continued at −78° C. After 30 min, another 1.39 ml (1.39 mmol) of boron tribromide (1 M in dichloromethane) are added. After 30 min, 100 ml of water are added and the mixture is stirred for 30 min and allowed to warm to room temperature. The mixture is then extracted repeatedly with ethyl acetate. The combined organic phases are washed once with saturated sodium bicarbonate solution and once with saturated sodium chloride solution, dried over sodium sulfate, filtered and concentrated. The crude product is purified on a silica gel column (mobile phase: cyclohexane/ethyl acetate 25:1). This gives 1.85 g (62% of theory) of the title compound.

¹H-NMR (400 MHz, CDCl₃): δ=11.79 (s, 1H), 7.99 (d, 2H), 7.72 (d, 2H), 6.49 (s, 1H), 2.82 (heptet, 1H), 2.76 (s, 2H), 1.94-1.82 (m, 2H), 1.81-1.70 (m, 2H), 1.62-1.47 (m, 10H).
MS (DCI): m/z=433 (M+H)⁺, 450 (M+NH₄)⁺.

Example 10A

7-Cyclopentyl-2,2-dimethyl-4-oxo-6-[4-(trifluoromethyl)benzoyl]-3,4-dihydro-2H-chromen-5-yl trifluoromethanesulfonate

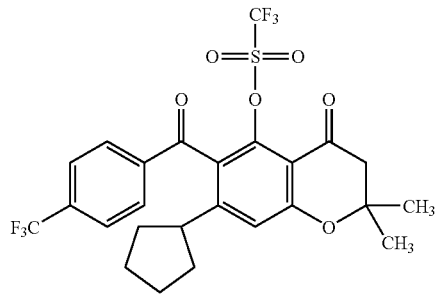

Under argon, 390 mg (0.90 mmol) of 7-cyclopentyl-5-hydroxy-2,2-dimethyl-6-[4-(trifluoro-methyl)benzoyl]-2,3-dihydro-4H-chromen-4-one (Example 9A) are dissolved in 3 ml of abs. dimethylformamide. The mixture is cooled to 0° C., 137 mg (0.99 mmol) of potassium carbonate are added and the mixture is stirred for 15 min and then cooled to −20° C. A solution of 338 mg (0.95 mmol) of N,N-bis(trifluoromethanesulfonyl)aniline in 1.5 ml of abs. dimethylformamide is slowly added dropwise. The mixture is stirred at −20° C. for one hour and then slowly warmed to room temperature, and stirring is continued. After 3 h, another 20 mg (0.06 mmol) of N,N-bis(trifluoromethanesulfonyl)aniline are added and stirring of the mixture at room temperature is continued. After 2 h, ammonium chloride solution is added, the mixture is diluted with water and ethyl acetate, the organic phase is separated off and the aqueous phase is extracted twice with ethyl acetate. The combined organic phases are washed twice with saturated sodium chloride solution, dried over magnesium sulfate, filtered and concentrated. The residue is chromatographed on silica gel (mobile phase: cyclohexane→cyclohexane/ethyl acetate 10:1). This gives 482 mg (95% of theory) of the title compound.

$^1$H-NMR (300 MHz, CDCl$_3$): δ=7.89 (d, 2H), 7.72 (d, 2H), 7.09 (s, 1H), 2.89 (heptet, 1H), 2.80 (s, 2H), 2.10-1.45 (m, 14H).

MS (ESIpos): m/z=565 (M+H)$^+$, 582 (M+NH$_4$)$^+$.

Example 11A

7-Cyclopentyl-5-(4-fluorophenyl)-2,2-dimethyl-6-[4-(trifluoromethyl)benzoyl]-2,3-dihydro-4H-chromen-4-one

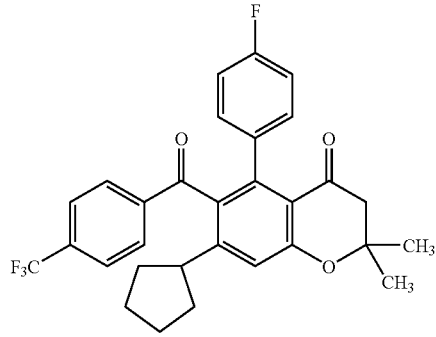

In a flask which had been dried by heating, 250 mg (0.44 mmol) of 7-cyclopentyl-2,2-dimethyl-4-oxo-6-[4-(trifluoromethyl)benzoyl]-3,4-dihydro-2H-chromen-5-yl trifluoromethanesulfonate (Example 10A), 81 mg (0.58 mmol) of 4-fluorophenylboronic acid, 160 mg (0.75 mmol) of potassium phosphate and 56 mg (0.05 mmol) of tetrakis(triphenylphosphine)palladium(0) are initially charged, and the apparatus is flushed by repeated evacuation and venting with argon. 4 ml of dioxane are then added, the apparatus is closed and the reaction mixture is heated under reflux overnight. The mixture is cooled and filtered through a layer of silica gel, the filter cake is washed thoroughly with ethyl acetate and the filtrate is concentrated. The crude product is purified on silica gel (mobile phase: cyclohexane→cyclohexane/ethyl acetate 10:1→5:1). This gives 194 mg (86% of theory) of the title compound.

$^1$H-NMR (300 MHz, CDCl$_3$): δ=7.60-7.49 (m, 4H), 7.15-6.45 (m, 5H), 2.81-2.60 (m, 3H), 2.18-1.96 (br. s, 1H), 1.84-1.45 (m, 13H).

MS (DCI): m/z=511 (M+H)$^+$, 528 (M+NH$_4$)$^+$.

Example 12A

[(4S)-7-Cyclopentyl-5-(4-fluorophenyl)-4-hydroxy-2,2-dimethyl-3,4-dihydro-2H-chromen-6-yl][4-(trifluoromethyl)phenyl]methanone

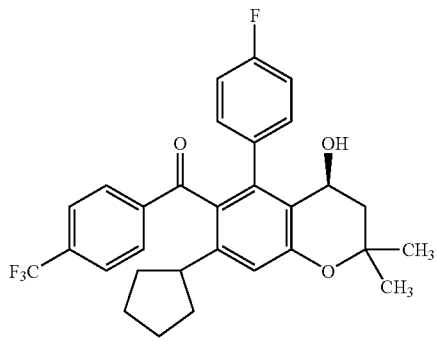

Under argon, 111 mg (0.71 mmol) of (1R,2S)-1-aminoindan-2-ol are initially charged in 100 ml of abs. tetrahydrofuran, 3.36 ml (18.89 mmol) of borane/N,N-diethylaniline complex are added with stirring and the mixture is stirred for 30 min. The mixture is then cooled to 0° C., and 2.41 g (4.72 mmol) of 7-cyclopentyl-5-(4-fluorophenyl)-2,2-dimethyl-6-[4-(trifluoromethyl)benzoyl]-2,3-dihydro-4H-chromen-4-one (Example 11A), dissolved in 150 ml of abs. tetrahydrofuran, are added. In a thawing ice bath, the mixture is slowly warmed to room temperature. After stirring overnight, methanol is added, the mixture is concentrated to dryness and the residue is taken up ethyl acetate. The mixture is washed twice with 1 N hydrochloric acid, twice with saturated sodium bicarbonate solution and twice with saturated sodium chloride solution. The organic phase is dried over sodium sulfate, filtered and concentrated. The residue is purified by column chromatography on silica gel (mobile phase: cyclohexane/ethyl acetate 10:1). This gives 1.72 g (71% of theory) of the title compound having an ee of 92%. Subsequent chromatographic separation of the enantiomers on a chiral phase [column: Chiralpak AD-H, 250×20 mm; mobile phase: isopropanol/isohexane 3:97; flow rate: 15 ml/min; 24° C.; detection: 254 nm] gives 1.3 g of the desired enantiomerically pure compound.

R$_t$=14.62 min [column: Chiralpak ID, 250×4.6 mm; mobile phase: isopropanol/isohexane 3:97; flow rate: 1.0 ml/min; detection: 254 nm].

$^1$H-NMR (300 MHz, CDCl$_3$): δ=7.61 (d, 2H), 7.54 (d, 2H), 7.20-6.74 (m, 5H), 4.70 (br. s, 1H), 2.72 (heptet, 1H), 2.02 (d, 2H), 2.00-1.41 (m, 14H).

MS (ESIpos): m/z=513 (M+H)$^+$.

Example 13A

[(4S)-4-{[tert-Butyl(dimethyl)silyl]oxy}-7-cyclopentyl-5-(4-fluorophenyl)-2,2-dimethyl-3,4-dihydro-2H-chromen-6-yl][4-(trifluoromethyl)phenyl]methanone

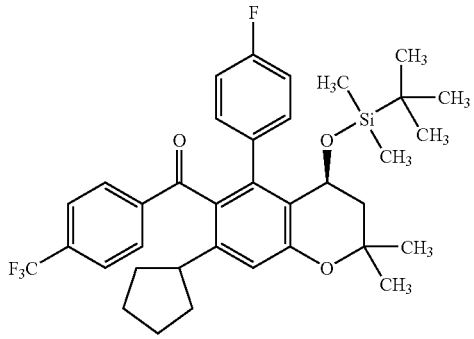

Under argon, 200 mg (0.39 mmol) of [(4S)-7-cyclopentyl-5-(4-fluorophenyl)-4-hydroxy-2,2-dimethyl-3,4-dihydro-2H-chromen-6-yl][4-(trifluoromethyl)phenyl]methanone (Example 12A) and 180 μl (1.56 mmol) of 2,6-dimethylpyridine are dissolved in 1.25 ml of toluene and cooled to −20° C. A solution of 0.18 ml (0.78 mmol) of tert-butyldimethylsilyl trifluoromethanesulfonate in 1.25 ml of toluene is added dropwise, and the mixture is stirred at −20° C. for 15 min, then warmed to 0° C. and stirred for 1 hour. Another 18 μl (0.078 mmol) of tert-butyldimethylsilyl trifluoromethanesulfonate are added, and stirring is continued for another 1.5 h. 5 ml of 0.1 N hydrochloric acid are added, and the mixture is extracted repeatedly with ethyl acetate. The organic phases are washed with a 1:1 mixture of saturated sodium bicarbonate solution and saturated sodium chloride solution and with saturated sodium chloride solution, dried over sodium sulfate, filtered and concentrated. The residue is purified by column chromatography on silica gel (mobile phase: cyclohexane/ethyl acetate 15:1). This gives 227 mg (93% of theory) of the title compound.

$^1$H-NMR (400 MHz, CDCl$_3$): δ 7.75-7.30 (br. s, 4H), 7.20-6.47 (m, 5H), 4.36 (br. s, 1H), 2.71 (br. s, 1H), 2.09 (dd, 1H), 2.00-1.90 (m, 1H), 1.80-1.61 (m, 4H), 1.59-1.41 (m, 10H), 0.69 (s, 9H), −0.12 (s, 3H), −0.73 (s, 3H).

MS (DCI): m/z=644 (M+NH)$^+$.

Example 14A

[(4S)-4-{[tert-Butyl(dimethyl)silyl]oxy}-7-cyclopentyl-5-(4-fluorophenyl)-2,2-dimethyl-3,4-dihydro-2H-chromen-6-yl][4-(trifluoromethyl)phenyl]methanol

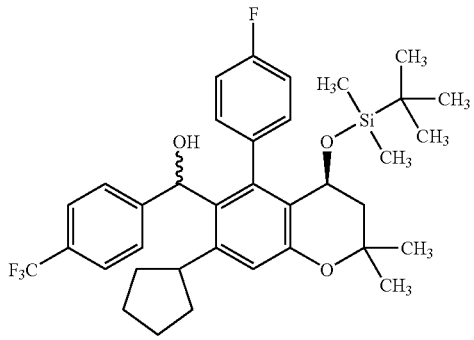

Under argon, 102 mg (0.16 mmol) of [(4S)-4-{[tert-butyl(dimethyl)silyl]oxy}-7-cyclopentyl-5-(4-fluorophenyl)-2,2-dimethyl-3,4-dihydro-2H-chromen-6-yl][4-(trifluoromethyl)phenyl]methanone (Example 13A) are initially charged in 2 ml of abs. toluene and cooled to −78° C. 250 μl (0.25 mmol) of a diisobutylaluminum hydride solution (1 M in hexane) are slowly added dropwise, and the mixture is stirred at −78° C. After 30 min, another 80 μl (0.08 mmol) of diisobutylaluminum hydride solution (1 M in hexane) are added dropwise, and the mixture is stirred for another 30 min. 20% strength sodium/potassium tartrate solution is added, and the mixture is extracted repeatedly with ethyl acetate. The combined organic phases are washed with saturated sodium chloride solution, dried over sodium sulfate, filtered and concentrated. The crude product obtained is purified by preparative thick-layer chromatography on silica gel (mobile phase: cyclohexane/ethyl acetate 5:1). This gives 47 mg (46% of theory) of the title compound which is used in the next step without further characterization.

Example 15A tert-Butyl[((4S)-7-cyclopentyl-5-(4-fluorophenyl)-6-{fluoro[4-(trifluoromethyl)phenyl]methyl}-2,2-dimethyl-3,4-dihydro-2H-chromen-4-yl)oxy]dimethylsilane

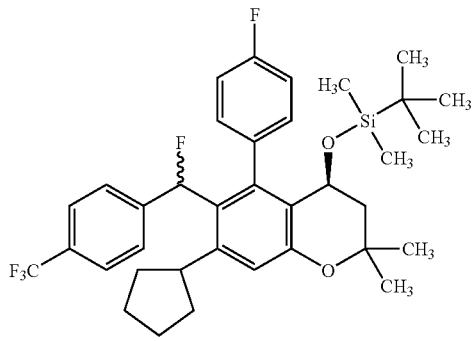

Under argon, 47 mg (0.07 mmol) of [(4S)-4-{[tert-butyl(dimethyl)silyl]oxy}-7-cyclopentyl-5-(4-fluorophenyl)-2,2-dimethyl-3,4-dihydro-2H-chromen-6-yl][4-(trifluoromethyl)phenyl]methanol (Example 14A) are dissolved in 500 μl of dichloromethane, and 16.3 μl (0.12 mmol) of diethylaminosulfur trifluoride are added slowly at room temperature. The mixture is stirred at room temperature for 1 h, water is then added and the mixture is extracted repeatedly with dichloromethane. The combined organic phases are washed once with saturated sodium bicarbonate solution and twice with saturated sodium chloride solution, dried over sodium sulfate, filtered and concentrated. The crude product is purified by preparative thick-layer chromatography on silica gel (mobile phase: cyclohexane/ethyl acetate 5:1). This gives 21 mg (45% of theory) of the title compound.

MS (ESIpos): m/z=499 [M−OSi(CH$_3$)$_2$C(CH$_3$)$_3$]$^+$.

Example 16A

5-Hydroxy-2,2-dimethyl-4-oxo-3,4-dihydro-2H-chromen-7-yl trifluoromethanesulfonate

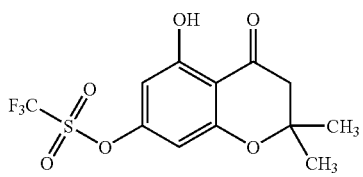

At 0° C., 4.88 g (35.3 mmol) of potassium carbonate are added to a solution of 6.69 g (32.1 mmol) of 5,7-dihydroxy-2,2-dimethyl-2,3-dihydro-4H-chromen-4-one [prepared according to L. Xie, Y. Takeuchi, M. Cosentino, A. T. McPhail, K.-H. Lee, *J. Med. Chem.* 44, 664-671 (2001)] in 80 ml of dimethylformamide, and the mixture is stirred at this temperature for 15 min. The mixture is then cooled to −20° C., and a solution of 11.48 g (31.1 mmol) of N-phenylbis(trifluoro-methanesulfonimide) in 50 ml of dimethylformamide is slowly added dropwise. The mixture is stirred at this temperature for 3 h, 10 ml of saturated sodium bicarbonate solution and 1000 ml of water are then added and the mixture is extracted twice with in each case 500 ml of ethyl acetate. The combined organic phases are washed with 200 ml of water and 200 ml of saturated sodium bicarbonate solution and dried over sodium sulfate, and the solvent is then removed under reduced pressure. Purification of the residue by column chromatography on silica gel (mobile phase: gradient cyclohexane→cyclohexane/ethyl acetate 20:1) gives the target product.

Yield: 8.50 g (78% of theory)
LC/MS (Method 9): $R_t$=2.94 min.
MS (ESIpos): m/z=341 (M+H)$^+$
$^1$H-NMR (CDCl$_3$, 300 MHz): δ=1.49 (s, 6H), 2.78 (s, 2H), 6.34 (d, 1H), 6.39 (d, 1H).

Example 17A

5-Hydroxy-7-isopropyl-2,2-dimethyl-2,3-dihydro-4H-chromen-4-one

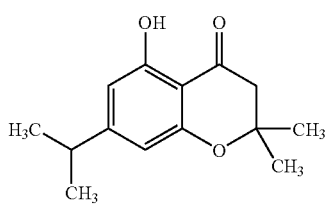

At 0° C., 450 mg (550 μmol) of bis(diphenylphosphino)ferrocenepalladium(II) chloride/dichloromethane complex are added to a solution of 4.25 g (12.5 mmol) of 5-hydroxy-2,2-dimethyl-4-oxo-3,4-dihydro-2H-chromen-7-yl trifluoromethanesulfonate (Example 16A) and 1.59 g (37.5 mmol) of lithium chloride in 80 ml of degassed dimethylformamide. 24.98 ml (24.98 mmol) of a 1 M solution of diisopropylzinc in toluene are then slowly added dropwise. After 10 min of stirring at 0° C., the mixture is warmed to room temperature and stirred at this temperature for a further 5 h. The reaction solution is hydrolyzed carefully with water, acidified with 1 M hydrochloric acid, diluted with 500 ml of water and extracted twice with in each case 500 ml of ethyl acetate. After washing with 100 ml of water and 50 ml of saturated sodium chloride solution, the combined organic phases are dried over magnesium sulfate and concentrated under reduced pressure. Chromatography of the residue on silica gel (mobile phase: cyclohexane/ethyl acetate 10:1) gives the target product as a 2:1 mixture with the isomer 5-hydroxy-2,2-dimethyl-7-propyl-2,3-dihydro-4H-chromen-4-one.

Yield: 2.06 g (66% of theory)
LC/MS (Method 7): $R_t$=2.60 min (main isomer), $R_t$=2.65 min (minor isomer)
MS (ESIpos): Main isomer: m/z=235 (M+H)$^+$; minor isomer: m/z=235 (M+H)$^+$
$^1$H-NMR (CDCl$_3$, 400 MHz): Main isomer: δ=1.21 (d, 6H), 1.46 (s, 6H), 2.71 (s, 2H), 2.73-2.85 (m, 1H), 6.28 (d, 1H), 6.37 (d, 1H), 11.62 (s, 1H); minor isomer: δ=0.94 (t, 3H), 1.46 (s, 6H), 1.58-1.71 (m, 2H), 2.48 (t, 2H), 2.72 (s, 2H), 6.22 (d, 1H), 6.30 (d, 1H), 11.64 (s, 1H).

The mixture of isomers is separated by preparative HPLC (Method 3), giving 1.03 g of isomerically pure 5-hydroxy-7-isopropyl-2,2-dimethyl-2,3-dihydro-4H-chromen-4-one:

$R_t$=3.35 min (HP 1100; Kromasil C18 5 μm, 250 mm×4 mm; 40° C.; flow rate: 1 ml/min; detection: 280 nm; mobile phase: acetonitrile/water 70:30).

Example 18A

5-Hydroxy-7-isopropyl-2,2-dimethyl-4-oxochroman-6-carbaldehyde

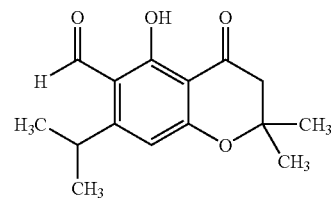

At −50° C., 13.19 ml (13.19 mmol) of a 1 M solution of titanium(IV) chloride in dichloromethane are added dropwise to a solution of 1.03 g (4.40 mmol) of 5-hydroxy-7-isopropyl-2,2-dimethyl-2,3-dihydro-4H-chromen-4-one (Example 17A) in 50 ml of dichloromethane, and the mixture is stirred at this temperature for 5 min. 437 μl (4.84 mmol) of dichloromethyl methyl ether are then slowly added dropwise. Over a period of 2.5 h, the mixture is allowed to thaw to −25° C. The mixture is then diluted with ethyl acetate and 1 M hydrochloric acid, the aqueous phase is extracted with ethyl acetate and the combined organic phases are dried over sodium sulfate. The solvent is removed under reduced pressure and the residue is purified by column chromatography on silica gel (mobile phase: cyclohexane/ethyl acetate 16:1).

Yield: 1.05 g (91% of theory)
LC/MS (Method 9): $R_t$=2.72 min.
MS (ESIpos): m/z=263 (M+H)$^+$ $^1$H-NMR (CDCl$_3$, 300 MHz): δ=1.19 (d, 6H), 1.52 (s, 6H), 2.78 (s, 2H), 4.02-4.17 (m, 1H), 6.46 (s, 1H), 10.49 (s, 1H), 12.70 (br. s, 1H).

Example 19A

6-Formyl-7-isopropyl-2,2-dimethyl-4-oxo-3,4-dihydro-2H-chromen-5-yl trifluoromethanesulfonate

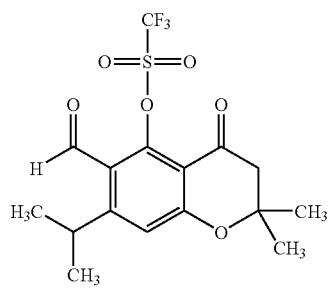

At 0° C., 1.35 g (9.77 mmol) of potassium carbonate are added to a solution of 2.33 g (8.88 mmol) of 5-hydroxy-7-isopropyl-2,2-dimethyl-4-oxochroman-6-carbaldehyde (Example 18A) in 20 ml of dimethylformamide, and the mixture is stirred at 0° C. for 15 min. At −20° C., a solution of 3.49 g (9.77 mmol) of N-phenylbis(trifluoromethanesulfonimide) in 15 ml of dimethylformamide is then added dropwise, and the mixture is stirred at this temperature for 1 h. Over a period of 3 h, the mixture is then allowed to thaw to 0° C., and a saturated ammonium chloride solution and 200 ml of water are then added. After extraction with 2×150 ml of ethyl acetate, washing of the combined organic phases with 150 ml of saturated sodium chloride solution and drying over magnesium sulfate, the solvent is removed under reduced pressure. Crystallization of the residue from cyclohexane gives the target product.

Yield: 2.65 g (76% of theory)
LC/MS (Method 7): R$_t$=2.76 min.
MS (ESIpos): m/z=395 (M+H)$^+$
$^1$H-NMR (CDCl$_3$, 300 MHz): δ=1.24 (d, 6H), 1.52 (s, 6H), 2.79 (s, 2H), 3.88-4.03 (m, 1H), 7.04 (s, 1H), 10.38 (s, 1H).

Example 20A 5-(4-Fluorophenyl)-7-isopropyl-2,2-dimethyl-4-oxochroman-6-carbaldehyde

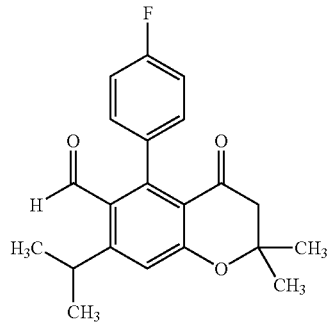

A solution of 800 mg (2.03 mmol) of 6-formyl-7-isopropyl-2,2-dimethyl-4-oxo-3,4-dihydro-2H-chromen-5-yl trifluoromethanesulfonate (Example 19A), 369 mg (2.64 mmol) of 4-fluorophenyl-boronic acid, 164 mg (142 μmol) of tetrakis(triphenylphosphine)palladium and 731 mg (3.45 mmol) of potassium carbonate and 10 ml of degassed dioxane is stirred at 100° C. overnight. After cooling to room temperature, ammonium chloride solution is added and the mixture is extracted twice with ethyl acetate. After drying of the combined organic phases over sodium sulfate, the solvent is removed under reduced pressure and the residue is purified by column chromatography (mobile phase: gradient cyclohexane→cyclohexane/ethyl acetate 20:1).

Yield: 616 mg (87% of theory)
LC/MS (Method 7): R$_t$=2.79 min.
MS (ESIpos): m/z=341 (M+H)$^+$
$^1$H-NMR (CDCl$_3$, 400 MHz): δ=1.28 (d, 6H), 1.49 (s, 6H), 2.64 (s, 2H), 3.87-4.02 (m, 1H), 7.02-7.24 (m, 2H), 9.60 (s, 1H).

Example 21A rac-5-(4-Fluorophenyl)-6-{hydroxy[4-(trifluoromethyl)phenyl]methyl}-7-isopropyl-2,2-dimethyl-2,3-dihydro-4H-chromen-4-one

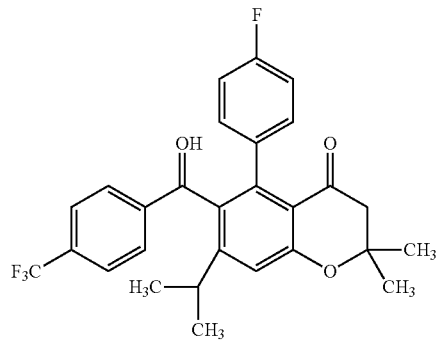

At −78° C., 2.29 ml (1.15 mmol) of a freshly prepared 0.5 M solution of bromo[4-(trifluoromethyl)phenyl]magnesium in tetrahydrofuran are slowly added dropwise to a solution of 300 mg (881 μmol) of 5-(4-fluorophenyl)-7-isopropyl-2,2-dimethyl-4-oxochroman-6-carbaldehyde (Example 20A) in 7 ml of tetrahydrofuran. The mixture is then allowed to thaw slowly to −20° C. and stirred at this temperature for 45 min. A 10% strength sodium bicarbonate solution is then added, the mixture is extracted three times with ethyl acetate and the combined organic phases are washed with saturated sodium chloride solution. The organic phases are dried over magnesium sulfate, the solvent is then removed under reduced pressure and the residue is purified by column chromatography on silica gel (mobile phase: gradient cyclohexane→cyclohexane/ethyl acetate 10:1).

Yield: 400 mg (85% of theory)
LC/MS (method 7): R$_t$=3.06 min
MS (ESIpos): m/z=503 (M+H)$^+$
$^1$H-NMR (CDCl$_3$, 400 MHz): δ=0.66 (d, 3H), 1.18 (d, 3H), 1.47 (s, 3H), 1.49 (s, 3H), 2.12 (d, 1H), 2.57 (d, 1H), 2.68 (d, 1H), 3.02-3.18 (m, 1H), 5.68-5.77 (m, 1H), 6.98 (s, 1H), 6.99-7.20 (m, 4H), 7.32 (d, 2H), 7.53 (d, 2H).

Example 22A rac-5-(4-Fluorophenyl)-6-{fluoro[4-(trifluoromethyl)phenyl]methyl}-7-isopropyl-2,2-dimethyl-2,3-dihydro-4H-chromen-4-one

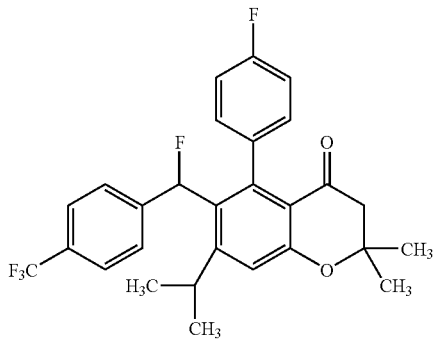

At −78° C., a solution of 51 µl (380 µmol) of diethylaminosulfur trifluoride in 1 ml of dichloromethane is slowly added dropwise to a solution of 170 mg (350 µmol) of rac-5-(4-fluorophenyl)-6-{hydroxy[4-(trifluoromethyl)phenyl]methyl}-7-isopropyl-2,2-dimethyl-2,3-dihydro-4H-chromen-4-one (Example 21A) in 4.5 ml of dichloromethane, and the mixture is stirred at this temperature for 2.5 h. The mixture is then allowed to thaw slowly to −20° C. Water is then added, and the mixture is extracted twice with ethyl acetate. The combined organic phases are dried over sodium sulfate and concentrated under reduced pressure. Crystallization of the residue from cyclohexane/ethyl acetate (10:1) gives 77 mg of the target product. Column chromatography of the concentrated mother liquor on silica gel (mobile phase: cyclohexane/ethyl acetate 20:1) gives a further 60 mg of the target compound.

Yield: 137 mg (78% of theory)
LC/MS (method 8): $R_t$=3.10 min
MS (ESIpos): m/z=489 (M+H)$^+$
$^1$H-NMR (CDCl$_3$, 300 MHz): δ=0.74 (d, 3H), 1.18 (d, 3H), 1.48 (s, 3H), 1.51 (s, 3H), 2.62 (d, 1H), 2.68 (d, 1H), 2.82-2.98 (m, 1H), 6.33 (d, 1H), 6.97 (d, 2H), 7.03 (s, 1H), 7.04-7.22 (m, 4H), 7.57 (d, 2H).

Example 23A 5-(4-Fluorophenyl)-7-isopropyl-2,2-dimethyl-6-[4-(trifluoromethyl)benzoyl]-2,3-dihydro-4H-chromen-4-one

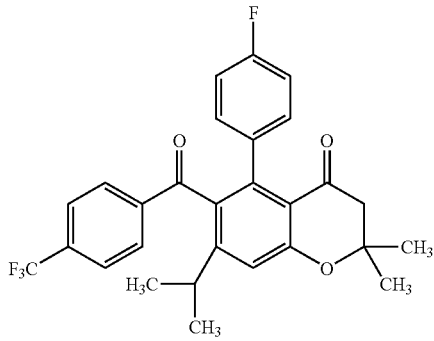

At 0° C., 174 mg (410 µmol) of 1,1-dihydro-1,1,1-triacetoxy-1,2-benziodoxol-3(1H)-one are added to a solution of 100 mg (207 µmol) of rac-5-(4-fluorophenyl)-6-{hydroxy[4-(trifluoromethyl)-phenyl]methyl}-7-isopropyl-2,2-dimethyl-2,3-dihydro-4H-chromen-4-one (Example 21A) in 4.5 ml of dichloromethane, and the mixture is stirred at this temperature for 4 h. The mixture is then diluted with dichloromethane and washed three times with 1 M aqueous sodium hydroxide solution. The organic phase is dried over magnesium sulfate and then concentrated under reduced pressure, and the residue is purified by column chromatography on silica gel (mobile phase: cyclohexane/ethyl acetate 20:1).

Yield: 86 mg (86% of theory)
LC/MS (method 9): $R_t$=3.32 min
MS (ESIpos): m/z=485 (M+H)$^+$
$^1$H-NMR (CDCl$_3$; 300 MHz): δ=0.98-1.37 (m, 6H), 1.39-1.64 (m, 6H), 2.57-2.79 (m, 3H), 6.44-7.19 (m, 4H), 7.03 (s, 1H), 7.53 (d, 2H), 7.58 (d, 2H).

Example 24A rac-5-(4-Fluorophenyl)-6-{hydroxy[4-(trifluoromethoxy)phenyl]methyl}-7-isopropyl-2,2-dimethyl-2,3-dihydro-4H-chromen-4-one

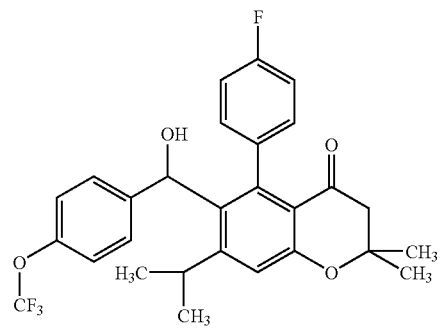

At −78° C., 2.35 ml (1.19 mmol) of a freshly prepared 0.5 M solution of bromo[4-(trifluoromethoxy)phenyl]magnesium in tetrahydrofuran are slowly added dropwise to a solution of 338 mg (990 µmol) of a 2:1 mixture of rac-5-(4-fluorophenyl)-7-isopropyl-2,2-dimethyl-4-oxochroman-6-carbaldehyde (Example 20A) and rac-5-(4-fluorophenyl)-7-n-propyl-2,2-dimethyl-4-oxochroman-6-carbaldehyde in 8 ml of tetrahydrofuran. The mixture is then allowed to thaw slowly to −20° C. and stirred at this temperature for 45 min. 10% strength sodium bicarbonate solution is then added, the mixture is extracted three times with ethyl acetate and the combined organic phases are washed with saturated sodium chloride solution. The organic phases are dried over magnesium sulfate, the solvent is then removed under reduced pressure and the residue is purified by preparative HPLC (method 1).

Yield: 293 mg (59% of theory)
LC/MS (method 7): $R_t$=3.06 min
MS (ESIpos): m/z=503 (M+H)$^+$
$^1$H-NMR (CDCl$_3$, 300 MHz): δ=0.66 (d, 3H), 1.18 (d, 3H), 1.47 (s, 3H), 1.49 (s, 3H), 2.12 (d, 1H), 2.57 (d, 1H), 2.68 (d, 1H), 3.02-3.18 (m, 1H), 5.68-5.77 (m, 1H), 6.98 (s, 1H), 6.99-7.18 (m, 6H), 7.22 (d, 6H).

Example 25A rac-5-(4-Fluorophenyl)-6-{fluoro[4-(trifluoromethoxy)phenyl]methyl}-7-isopropyl-2,2-dimethyl-2,3-dihydro-4H-chromen-4-one

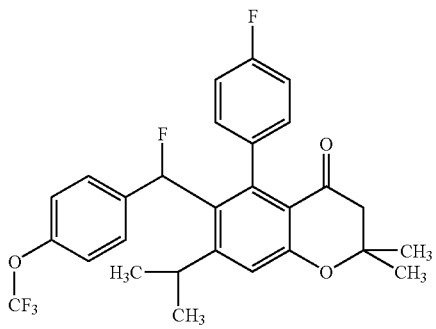

At −78° C., a solution of 45 μl (340 μmol) of diethylaminosulfur trifluoride in 1 ml of dichloromethane is slowly added dropwise to a solution of 157 mg (310 μmol) of rac-5-(4-fluorophenyl)-6-{hydroxy[4-(trifluoromethoxy)phenyl]methyl}-7-isopropyl-2,2-dimethyl-2,3-dihydro-4H-chromen-4-one (Example 24A) in 4 ml of dichloromethane, and the mixture is stirred at this temperature for 2.5 h. The mixture is then allowed to thaw slowly to −15° C. and stirred for a further 1.5 h. Water is then added, and the mixture is extracted twice with ethyl acetate. The combined organic phases are dried over sodium sulfate and concentrated under reduced pressure. Column chromatography of the residue on silica gel (mobile phase: gradient cyclohexane→cyclohexane/ethyl acetate 10:1→15:1) gives the target compound.

Yield: 145 mg (92% of theory)
LC/MS (method 9): $R_t$=3.42 min
MS (ESIpos): m/z=505 (M+H)$^+$.

Example 26A 5-(4-Fluorophenyl)-7-isopropyl-2,2-dimethyl-6-[4-(trifluoromethoxy)benzoyl]-2,3-dihydro-4H-chromen-4-one

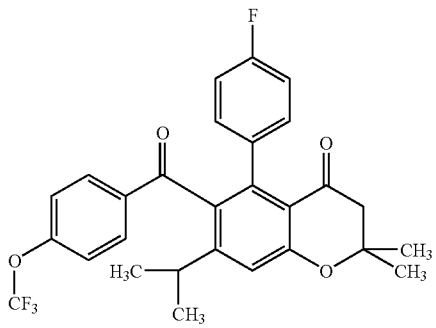

At 0° C., 185 mg (439 μmol) of 1,1-dihydro-1,1,1-triacetoxy-1,2-benziodoxol-3(1H)-one are added to a solution of 110 mg (220 μmol) of 5-(4-fluorophenyl)-6-{hydroxy[4-(trifluoromethoxy)-phenyl]methyl}-7-isopropyl-2,2-dimethyl-2,3-dihydro-4H-chromen-4-one (Example 24A) in 4.5 ml of dichloromethane, and the mixture is stirred at this temperature for 4 h. The mixture is then diluted with dichloromethane and washed three times with 1 M aqueous sodium hydroxide solution. The organic phase is dried over magnesium sulfate and then concentrated under reduced pressure, and the residue is purified by column chromatography on silica gel (mobile phase: gradient cyclohexane→cyclohexane/ethyl acetate 10:1).

Yield: 80 mg (68% of theory)
LC/MS (method 9): $R_t$=3.29 min
MS (ESIpos): m/z=467 (M+H)$^+$
$^1$H-NMR (CDCl$_3$, 300 MHz): δ=1.03-1.38 (m, 6H), 1.39-1.63 (m, 6H), 2.52-2.82 (m, 3H), 6.51-7.18 (m, 7H), 7.54 (d, 2H).

Example 27A rac-6-[(4-tert-Butylphenyl)(hydroxy)methyl]-5-(4-fluorophenyl)-7-isopropyl-2,2-dimethyl-2,3-dihydro-4H-chromen-4-one

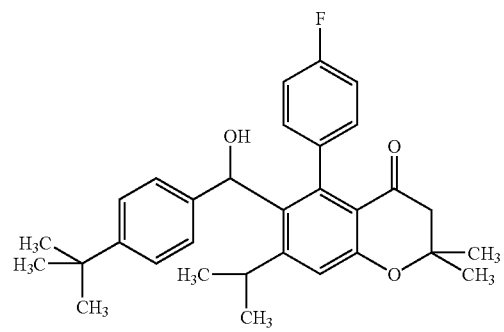

At −78° C., 2.12 ml (1.06 mmol) of a freshly prepared 0.5 M solution of bromo(4-tert-butylphenyl)magnesium in tetrahydrofuran are slowly added dropwise to a solution of 300 mg (880 μmol) of 5-(4-fluorophenyl)-7-isopropyl-2,2-dimethyl-4-oxochroman-6-carbaldehyde (Example 20A) in 7 ml of tetrahydrofuran. The mixture is then allowed to thaw slowly to −20° C. and stirred at this temperature for 45 min. 10% strength sodium bicarbonate solution is then added, the mixture is extracted three times with ethyl acetate and the combined organic phases are washed with saturated sodium chloride solution. The organic phases are dried over magnesium sulfate, the solvent is then removed under reduced pressure and the residue is purified by column chromatography on silica gel (mobile phase: gradient cyclohexane→cyclohexane/ethyl acetate 10:1).

Yield: 325 mg (78% of theory)
LC/MS (method 7): $R_t$=3.29 min
MS (ESIpos): m/z=475 (M+H)$^+$
$^1$H-NMR (CDCl$_3$, 300 MHz): δ=0.62 (d, 3H), 1.18 (d, 3H), 1.29 (s, 9H), 1.46 (s, 3H), 1.49 (s, 3H), 2.03 (d, 1H), 2.58 (d, 1H), 2.66 (d, 1H), 3.07-3.23 (m, 1H), 5.72 (d, 1H), 6.96 (s, 1H), 6.97-7.13 (m, 6H), 7.28-7.32 (m, 2H).

Example 28A rac-6-[(4-tert-Butylphenyl)(fluoro)methyl]-5-(4-fluorophenyl)-7-isopropyl-2,2-dimethyl-2,3-dihydro-4H-chromen-4-one

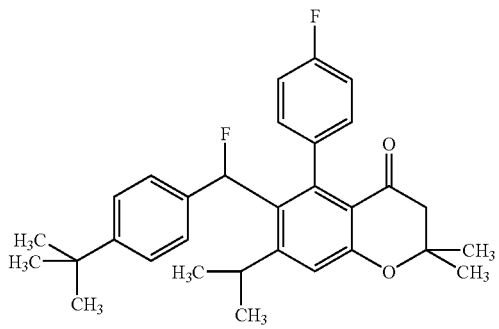

At −78° C., a solution of 46 μl (350 μmol) of diethylaminosulfur trifluoride in 1 ml of dichloromethane is slowly added dropwise to a solution of 150 mg (320 μmol) of rac-6-[(4-tert-butylphenyl)(hydroxy)methyl]-5-(4-fluorophenyl)-7-isopropyl-2,2-dimethyl-2,3-dihydro-4H-chromen-4-one (Example 27A) in 4.5 ml of dichloromethane, and the mixture is stirred at this temperature for 2.5 h. The mixture is then allowed to thaw slowly to −15° C. Water is then added, and the mixture is extracted twice with ethyl acetate. The combined organic phases are dried over sodium sulfate and concentrated under reduced pressure. Column chromatography of the residue on silica gel (mobile phase: gradient cyclohexane→cyclohexane/ethyl acetate 10:1→5:1) gives the target compound.

Yield: 127 mg (84% of theory)
LC/MS (method 7): R=3.42 min
MS (ESIpos): m/z=476 (M)$^+$
$^1$H-NMR (CDCl$_3$, 300 MHz): δ=0.73 (d, 3H), 1.16 (d, 3H), 1.29 (s, 9H), 1.48 (s, 3H), 1.50 (s, 3H), 2.59 (d, 1H), 2.68 (d, 1H), 2.95-3.11 (m, 1H), 6.30 (d, 1H), 6.89-7.33 (m, 9H).

Example 29A 6-(4-tert-Butylbenzoyl)-5-(4-fluorophenyl)-7-isopropyl-2,2-dimethyl-2,3-dihydro-4H-chromen-4-one

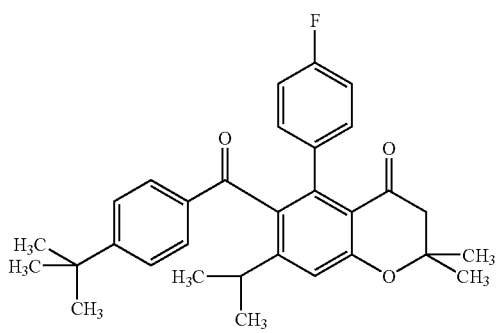

At 0° C., 340 mg (800 μmol) of 1,1-dihydro-1,1,1-triacetoxy-1,2-benziodoxol-3(1H)-one are added to a solution of 190 mg (400 μmol) of a 2:1 mixture of rac-6-[(4-tert-butylphenyl)(hydroxy)-methyl]-5-(4-fluorophenyl)-7-isopropyl-2,2-dimethyl-2,3-dihydro-4H-chromen-4-one (Example 27A) and rac-6-[(4-tert-butylphenyl)(hydroxy)methyl]-5-(4-fluorophenyl)-7-n-propyl-2,2-dimethyl-2,3-dihydro-4H-chromen-4-one in 7.5 ml of dichloromethane, and the mixture is stirred at this temperature for 4 h. The mixture is then diluted with dichloromethane and washed three times with 1 M aqueous sodium hydroxide solution. The organic phase is dried over magnesium sulfate and then concentrated under reduced pressure, and the residue is purified by preparative HPLC (method 1) and subsequent column chromatography on silica gel (mobile phase: gradient cyclohexane→cyclohexane/dichloromethane/ethyl acetate 20:20:0.5).

Yield: 54 mg (29% of theory)
LC/MS (method 8): R$_t$=3.31 min
MS (ESIpos): m/z=473 (M+H)$^+$
$^1$H-NMR (CDCl$_3$, 300 MHz): δ=1.14 (d, 3H), 1.25 (d, 3H), 1.28 (s, 9H), 1.48 (s, 3H), 1.54 (s, 3H), 2.53-2.82 (m, 3H), 6.47-6.61 (m, 1H), 6.62-6.73 (m, 1H), 6.83-6.98 (m, 1H), 7.03 (s, 1H), 7.04-7.16 (m, 1H), 7.28 (d, 2H), 7.43 (d, 2H).

Example 30A

7-Isopropyl-2,2-dimethyl-4-oxo-5-phenylchroman-6-carbaldehyde

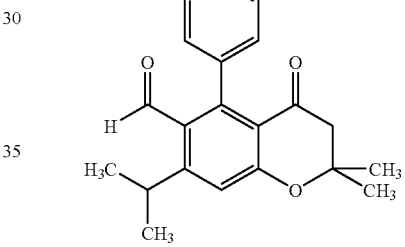

A solution of 350 mg (890 μmol) of a mixture of 6-formyl-7-isopropyl-2,2-dimethyl-4-oxo-3,4-dihydro-2H-chromen-5-yl trifluoromethanesulfonate (Example 19A) and 6-formyl-7-n-propyl-2,2-dimethyl-4-oxo-3,4-dihydro-2H-chromen-5-yl trifluoromethanesulfonate, 162 mg (1.33 mmol) of phenylboronic acid, 51 mg (40 μmol) of tetrakis(triphenylphosphine)palladium and 320 mg (1.51 mmol) of potassium phosphate in 6 ml of degassed dioxane is stirred at 100° C. overnight. After cooling to room temperature, the mixture is filtered through kieselguhr, the filter cake is washed with ethyl acetate and the filtrate is then concentrated under reduced pressure. Chromatography of the residue on silica gel (mobile phase: cyclohexane/ethyl acetate 9:1) gives the target compound as a 2:1 mixture with the corresponding n-propyl isomer.

Yield: 263 mg (92% of theory)
LC/MS (method 8): R$_t$=2.95 min (main isomer), R$_t$=2.99 min (minor isomer)
MS (ESIpos): main isomer: m/z=323 (M+H)$^+$; minor isomer: m/z=323 (M+H)$^+$
$^1$H-NMR (CDCl$_3$, 400 MHz): main isomer (target compound): δ=1.26 (d, 6H), 1.48 (s, 6H), 2.63 (s, 2H), 3.81-4.04 (m, 1H), 7.04 (s, 1H), 7.13-7.21 (m, 2H), 7.37-7.46 (m, 3H), 9.58 (s, 1H); minor isomer: δ=1.02 (t, 3H), 1.53 (s, 6H), 2.72 (s, 2H), 1.57-1.72 (m, 2H), 2.91-3.01 (m, 2H), 6.88 (s, 1H), 7.13-7.21 (m, 2H), 7.37-7.46 (m, 3H), 9.56 (s, 1H).

Example 31A rac-6-{Hydroxy[4-(trifluoromethoxy)phenyl]methyl}-7-isopropyl-2,2-dimethyl-5-phenyl-2,3-dihydro-4H-chromen-4-one

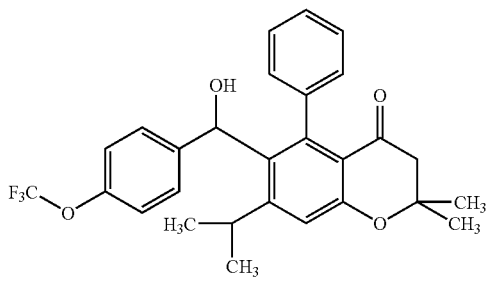

At −78° C., 1028 µl (510 µmol) of a freshly prepared 0.5 M solution of bromo[4-(trifluoromethoxy)phenyl]magnesium in tetrahydrofuran are slowly added dropwise to a solution of 138 mg (430 µmol) of a 2:1 mixture of 7-isopropyl-2,2-dimethyl-4-oxo-5-phenylchroman-6-carbaldehyde (Example 30A) and 7-n-propyl-2,2-dimethyl-4-oxo-5-phenyl-chroman-6-carbaldehyde in 4 ml of tetrahydrofuran. The mixture is then allowed to thaw slowly to −20° C. and stirred at this temperature for 45 min. To bring the reaction to completion, a further 342 µl (205 µmol) of the above Grignard solution are added dropwise, and the mixture is again stirred for 45 min. 10% strength sodium bicarbonate solution is added, the mixture is extracted three times with ethyl acetate and the combined organic phases are washed with saturated sodium chloride solution. The organic phases are dried over magnesium sulfate, the solvent is then removed under reduced pressure and the residue is purified by preparative HPLC (method 1), resulting in the removal of the n-propyl isomer from the target product.

Yield: 107 mg (52% of theory)
LC/MS (method 9): $R_t$=3.23 min
MS (ESIpos): m/z=485 (M+H)$^+$
$^1$H-NMR (CDCl$_3$, 300 MHz): δ=0.63 (d, 3H), 1.18 (d, 3H), 1.48 (s, 3H), 1.49 (s, 3H), 2.16 (d, 1H), 2.58 (d, 1H), 2.67 (d, 1H), 2.97-3.13 (m, 1H), 5.70-5.80 (m, 1H), 6.98 (s, 1H), 7.07-7.25 (m, 5H), 7.28-7.44 (m, 4H).

Example 32A

7-Isopropyl-2,2-dimethyl-5-phenyl-6-[4-(trifluoromethoxy)benzoyl]-2,3-dihydro-4H-chromen-4-one

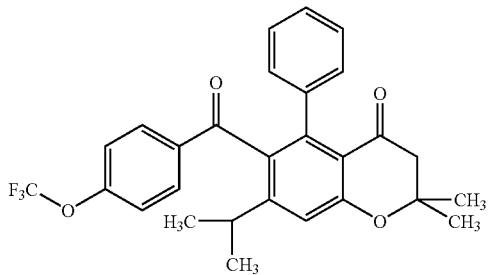

At 0° C., 166 mg (390 µmol) of 1,1-dihydro-1,1,1-triacetoxy-1,2-benziodoxol-3(1H)-one are added to a solution of 95 mg (197 µmol) of rac-6-{hydroxy[4-(trifluoromethoxy)phenyl]methyl}-7-iso-propyl-2,2-dimethyl-5-phenyl-2,3-dihydro-4H-chromen-4-one (Example 31A) in 3 ml of dichloromethane, and the mixture is stirred at this temperature for 4 h. The mixture is then diluted with dichloromethane and washed three times with 1 M aqueous sodium hydroxide solution. The organic phase is dried over magnesium sulfate and then concentrated under reduced pressure, and the residue is purified by column chromatography on silica gel (mobile phase: gradient cyclohexane→cyclohexane/ethyl acetate 10:1).

Yield: 61 mg (64% of theory)
LC/MS (method 9): $R_t$=3.23 min
MS (ESIpos): m/z=483 (M+H)$^+$
$^1$H-NMR (CDCl$_3$, 300 MHz): δ=1.07-1.38 (m, 6H), 1.39-1.63 (m, 6H), 2.53-2.82 (m, 3H), 6.51-6.78 (m, 1H), 6.81-6.97 (m, 1H), 7.00-7.32 (m, 6H), 7.51 (d, 2H).

Example 33A

5-Cyclohex-1-en-1-yl-7-isopropyl-2,2-dimethyl-4-oxochroman-6-carbaldehyde

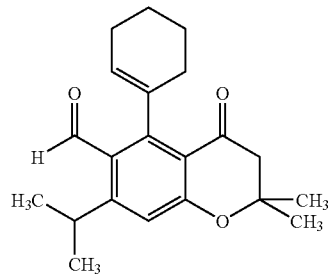

A solution of 365 mg (930 µmol) of 6-formyl-7-isopropyl-2,2-dimethyl-4-oxo-3,4-dihydro-2H-chromen-5-yl trifluoromethanesulfonate (Example 19A), 152 mg (1.20 mmol) of cyclohex-1-en-1-ylboronic acid, 75 mg (60 µmol) of tetrakis(triphenylphosphine)palladium and 334 mg (1.57 mmol) of potassium phosphate in 5.5 ml of degassed dioxane is stirred at 100° C. overnight. After cooling to room temperature, ammonium chloride solution is added and the mixture is extracted twice with ethyl acetate. The combined organic phases are dried over sodium sulfate, the solvent is then removed under reduced pressure and the residue is purified by column chromatography on silica gel (mobile phase:cyclohexane/ethyl acetate 20:1).

Yield: 203 mg (60% of theory)
LC/MS (method 8): $R_t$=3.21 min
MS (ESIpos): m/z=327 (M+H)$^+$
$^1$H-NMR (CDCl$_3$, 300 MHz): δ=1.19 (d, 3H), 1.25 (d, 3H), 1.44 (s, 3H), 1.49 (s, 3H), 1.56-1.73 (m, 1H), 1.73-2.07 (m, 4H), 2.12-2.27 (m, 2H), 2.42-2.48 (m, 1H), 2.62 (d, 1H), 2.73 (d, 1H), 3.84-4.00 (m, 1H), 5.38-5.48 (m, 1H), 6.91 (s, 1H), 10.09 (s, 1H).

Example 34A

5-Cyclopent-1-en-1-yl-7-isopropyl-2,2-dimethyl-4-oxochroman-6-carbaldehyde

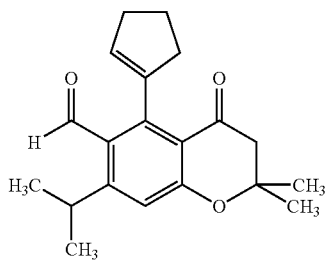

A solution of 550 mg (1.39 mmol) of 6-formyl-7-isopropyl-2,2-dimethyl-4-oxo-3,4-dihydro-2H-chromen-5-yl trifluoromethanesulfonate (Example 19A), 202 mg (1.81 mmol) of cyclopent-1-en-1-ylboronic acid, 112 mg (100 µmol) of tetrakis(triphenylphosphine)palladium and 503 mg (2.37 mmol) of potassium phosphate in 8 ml of degassed dioxane and stirred at 100° C. overnight. After cooling to room temperature, ammonium chloride solution is added and the mixture is extracted twice with ethyl acetate. The combined organic phases are dried over sodium sulfate, the solvent is then removed under reduced pressure and the residue is purified by column chromatography on silica gel (mobile phase: cyclohexane/ethyl acetate 20:1).

Yield: 235 mg (43% of theory)

LC/MS (method 8): $R_t$=3.11 min

MS (ESIpos): m/z=313 (M+H)$^+$ $^1$H-NMR (CDCl$_3$, 300 MHz): δ=1.22 (d, 6H), 1.47 (s, 6H), 2.06-2.23 (m, 2H), 2.49-2.62 (m, 4H), 2.68 (s, 2H), 3.83-4.00 (m, 1H), 5.51-5.58 (m, 1H), 6.92 (s, 1H), 9.98 (s, 1H).

Example 35A

5-Cyclohex-1-en-1-yl-6-{hydroxy[4-(trifluoromethyl)phenyl]methyl}-7-isopropyl-2,2-dimethyl-2,3-dihydro-4H-chromen-4-one

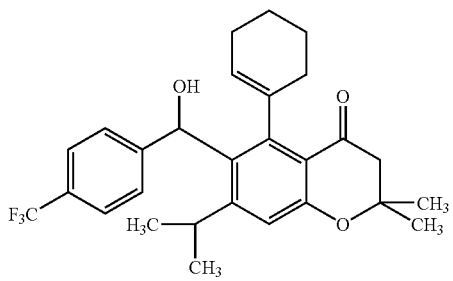

At −78° C., 2.03 ml (1.02 mmol) of a freshly prepared 0.5 M solution of bromo[4-(trifluoromethyl)phenyl]magnesium in tetrahydrofuran are slowly added dropwise to a solution of 255 mg (780 µmol) of 5-cyclohex-1-en-1-yl-7-isopropyl-2,2-dimethyl-4-oxochroman-6-carbaldehyde (Example 33A) in 6 ml of tetrahydrofuran. The mixture is then allowed to thaw slowly to −20° C. and stirred at this temperature for 45 min. A further 300 µl (193 µmol) of the above Grignard solution are added and stirring is continued for a further hour, the solution slowly thawing to 0° C. 10% strength sodium bicarbonate solution is then added, the mixture is extracted three times with ethyl acetate and the combined organic phases are washed with saturated sodium chloride solution. The organic phases are dried over magnesium sulfate and the solvent is then removed under reduced pressure. The residue is dissolved in a mixture of cyclohexane and ethyl:acetate (10:1), whereupon the target product crystallizes and is filtered off. The filtrate is concentrated and the residue is purified by column chromatography on silica gel (mobile phase: gradient cyclohexane→cyclohexane/ethyl acetate 20:1→10:1). The resulting target product is combined with the crystals. The compound is present in the form of atropisomers (1:1).

Yield: 304 mg (82% of theory)

LC/MS (method 8): $R_t$=3.34 min (isomer I), $R_t$=3.37 min (isomer II)

MS (ESIpos): isomer I: m/z=473 (M+H)$^+$; isomer II: m/z=473 (M+H)$^+$ $^1$H-NMR (CDCl$_3$, 300 MHz, isomer I [isomer II]): δ=0.54 [0.57] (d, 3H), 1.12 [1.14] (d, 3H), 1.42 [1.46] (s, 3H), 1.48 [1.50] (s, 3H), 1.64-2.03 (m, 5H), 2.06-2.25 (m, 2H), 2.28-2.49 (m, 1H), 2.58 [2.63] (d, 1H), 2.72 [2.79] (d, 1H), 2.89-3.09 (m, 1H), 5.33-5.40 [5.40-5.47] (m, 1H), 6.28-6.37 (m, 1H), 6.82 [6.83] (s, 1H), 7.34-7.46 (m, 2H), 7.54 (d, 2H).

Example 36A rac-5-Cyclopent-1-en-1-yl-6-{hydroxy[4-(trifluoromethyl)phenyl]methyl}-7-isopropyl-2,2-dimethyl-2,3-dihydro-4H-chromen-4-one

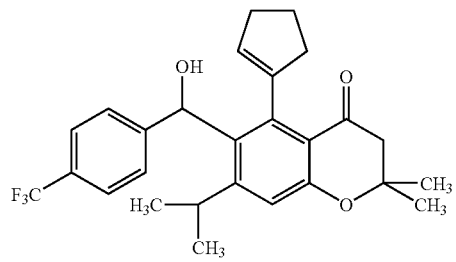

At −78° C., 780 µl (391 µmol) of a freshly prepared 0.5 M solution of bromo[4-(trifluoromethyl)phenyl]magnesium in tetrahydrofuran are slowly added dropwise to a solution of 94 mg (301 µmol) of 5-cyclopent-1-en-1-yl-7-isopropyl-2,2-dimethyl-4-oxochroman-6-carbaldehyde (Example 34A) in 2.3 ml of tetrahydrofuran. The mixture is then allowed to thaw slowly to −20° C. and stirred at this temperature for 45 min. 10% strength sodium bicarbonate solution is then added, the mixture is extracted three times with ethyl acetate and the combined organic phases are washed with saturated sodium chloride solution. The organic phases are dried over magnesium sulfate, the solvent is removed under reduced pressure and the residue is purified by column chromatography on silica gel (mobile phase: gradient cyclohexane→cyclohexane/ethyl acetate 20:1→10:1) and then by preparative HPLC (method 1).

Yield: 119 mg (79% of theory)

LC/MS (method 8): $R_t$=3.30 min

MS (ESIpos): m/z=459 (M+H)$^+$ $^1$H-NMR (CDCl$_3$, 300 MHz): δ=0.48-0.69 (m, 3H), 1.06-1.21 (m, 3H), 1.38-1.61 (m, 6H), 1.85-2.08 (m, 1H), 2.06-

2.90 (m, 8H), 2.62-3.12 (m, 1H), 5.38-5.52 (m, 1H), 6.18 (s, 1H), 6.83 (s, 1H), 7.33-7.44 (m, 2H), 7.56 (d, 2H).

Example 37A

5-Cyclohex-1-en-1-yl-7-isopropyl-2,2-dimethyl-6-[4-(trifluoromethyl)benzoyl]-2,3-dihydro-4H-chromen-4-one

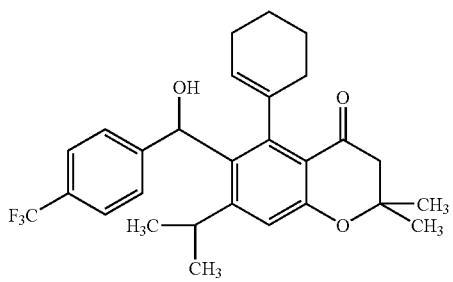

At 0° C., 153 mg (360 μmol) of 1,1-dihydro-1,1,1-triacetoxy-1,2-benziodoxol-3(1H)-one are added to a solution of 85 mg (180 μmol) of 5-cyclohex-1-en-1-yl-6-{hydroxy[4-(trifluoromethyl)phenyl]-methyl}-7-isopropyl-2,2-dimethyl-2,3-dihydro-4H-chromen-4-one (Example 35A) in 4 ml of dichloromethane, and the mixture is stirred at this temperature for 4 h. The mixture is then diluted with dichloromethane and washed three times with 1 M aqueous sodium hydroxide solution. The organic phase is dried over magnesium sulfate and then concentrated under reduced pressure, and the residue is purified by column chromatography on silica gel (mobile phase: gradient cyclohexane→cyclohexane/dichloromethane/ethyl acetate 20:20:0.5).

Yield: 61 mg (76% of theory)
LC/MS (method 9): $R_t$=3.21 min
MS (ESIpos): m/z=471 (M+H)$^+$
$^1$H-NMR (CDCl$_3$, 300 MHz): δ=0.65-1.10 (m, 2H), 1.15 (d, 3H), 1.19-1.70 (m, 12H), 1.71-2.25 (m, 3H), 2.64-2.92 (m, 3H), 4.87 and 5.47 (m, 1H), 6.94 (s, 1H), 7.65-7.97 (m, 4H).

Example 38A rac-5-Cyclopent-1-yl-6-{hydroxy[4-(trifluoromethyl)phenyl]methyl}-7-isopropyl-2,2-dimethyl-2,3-dihydro-4H-chromen-4-one

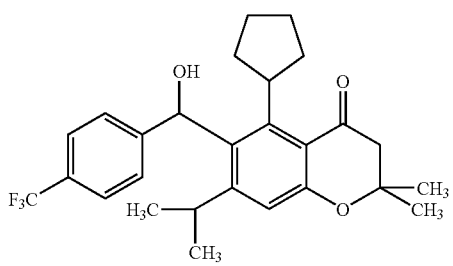

155 μl (872 μmol) of borane/N,N-diethylaniline complex are added slowly to a solution of 4.9 mg (33 μmol) of (1R, 2S)-1-aminoindan-2-ol in 5.0 ml of tetrahydrofuran, and the mixture is stirred for 30 min. A solution of 100 mg (218 μmol) of 5-cyclopent-1-en-1-yl-6-{hydroxy[4-(trifluoromethyl)phenyl]methyl}-7-isopropyl-2,2-dimethyl-2,3-dihydro-4H-chromen-4-one (Example 36A) in 5.0 ml of tetrahydrofuran is then, very slowly, added dropwise, and the mixture is stirred for 4 h. Methanol is then added, and the mixture is concentrated under reduced pressure. The residue is taken up in ethyl acetate and washed in each case twice with 1 M hydrochloric acid and saturated sodium bicarbonate solution and once with saturated sodium chloride solution. The organic phase is dried over sodium sulfate and then concentrated under reduced pressure. The crude product is purified by preparative HPLC (method 1). In addition to the title compound, the compounds described as Preparation Examples 22 and 23 are also isolated (for yield and analytical data see there).

Yield: 35 mg (35% of theory)
LC/MS (method 7): $R_t$=3.31 min
MS (ESIpos): m/z=461 (M+H)$^+$
$^1$H-NMR (CDCl$_3$, 400 MHz): δ=0.66 (br. m, 3H), 1.13 (d, 3H), 1.46 (s, 6H), 1.50-1.93 (m, 8H), 2.07 (m, 1H), 2.22 (d, 1H), 2.76 (s, 2H), 3.00 (s, 1H), 6.29 (m, 1H), 6.78 (s, 1H), 7.39 (d, 2H), 7.56 (d, 2H).

Example 39A

5-Cyclopentyl-7-isopropyl-2,2-dimethyl-6-[4-(trifluoromethyl)benzyl]-2,3-dihydro-4H-chromen-4-one

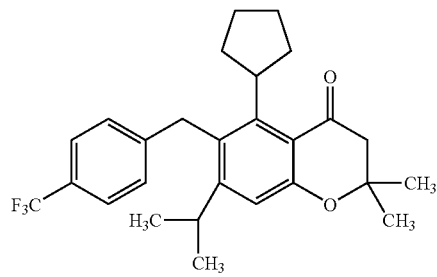

A mixture of 60 mg (130 μmol) of 5-cyclopent-1-en-1-yl-6-{hydroxy[4-(trifluoromethyl)phenyl]-methyl}-7-isopropyl-2,2-dimethyl-2,3-dihydro-4H-chromen-4-one (Example 36A) and 14 mg of palladium-on-carbon (10%) in 10 ml of ethanol is stirred under a hydrogen atmosphere at atmospheric pressure overnight. The suspension is filtered through Celite, the filter cake is washed with ethanol and the solvent is removed under reduced pressure. The residue is purified by column chromatography on silica gel (mobile phase: gradient cyclohexane→cyclohexane/ethyl acetate 40:1).

Yield: 23 mg (40% of theory)
LC/MS (method 7): $R_t$=3.42 min
MS (ESIpos): m/z=444 (M+H)$^+$.

Example 40A

Cyclobutylideneacetic Acid

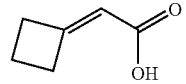

313 g (2.48 mol) of methyl cyclobutylideneacetate [prepared according to A. Goti et al., *Tetrahedron* 48 (25), 5283-5300 (1992)] are initially charged, a solution of 208 g (4.96 mol) of lithium hydroxide monohydrate in 4.38 liters of water is added at room temperature and the mixture is stirred at room temperature for 3.5 h. The mixture is then cooled to 0° C., and the pH is adjusted to 3.5 using concentrated hydrochloric acid. The product is then filtered off with suction, washed with a little cold water and dried under reduced pressure. This gives 213 g (76% of theory) of the title compound.

$^1$H-NMR (400 MHz, CDCl$_3$): δ=11.80 (br. s, 1H), 5.61-5.58 (m, 1H), 3.14 (t, 2H), 2.85 (t, 2H), 2.10 (quin, 2H).

MS (ESIpos): m/z=113 (M+H)$^+$.

Example 41A

Methyl Cyclopropylideneacetate

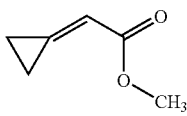

A suspension of 100 g (574 mmol) of [(1-ethoxycyclopropyl)oxy](trimethyl)silane, 250 g (746 mmol) of methyl(triphenylphosphoranylidene)acetate and 9.1 g (75 mmol) of benzoic acid in 1.64 liters of toluene is stirred at about 80° C. overnight. The mixture is then chromatographed directly on a silica gel column (mobile phase: 20 liters of petroleum ether→20 liters of dichloromethane). The product fractions are combined and concentrated at 400 mbar and 45° C. This gives 63 g (86% of theory) of the title compound as a colorless oil [see also F. Seyed-Mahdavi et al., *Tetrahedron Lett.* 27 (51), 6185-6188 (1986)].

$^1$H-NMR (300 MHz, CDCl$_3$): δ=6.21 (s, 1H), 3.72 (s, 3H), 1.42 (t, 2H), 1.20 (t, 2H).

GC/MS (method 10): R$_t$=3.03 min

MS (EIpos): m/z=112 (M)$^+$.

Example 42A 5,7-Dihydroxyspiro[chromen-2,1'-cyclobutan]-4(3H)-one

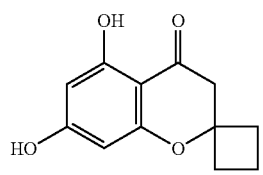

8 g (49.34 mmol) of 1,3,5-trihydroxybenzene dihydrate and 6.64 g (59.21 mmol) of cyclo-butylideneacetic acid (Example 40A) are initially charged, 25 ml (197.4 mmol) of boron trifluoride/diethyl ether complex are added and the mixture is then heated to 70° C. After three hours, the mixture is cooled, poured into 600 ml of ice-water, acidified with 6 N hydrochloric acid and extracted repeatedly with ethyl acetate. The combined organic phases are washed twice with saturated sodium chloride solution, dried over sodium sulfate, filtered and concentrated. The crude product is taken up in dichloromethane and stirred, and insoluble solid is then filtered off. Silica gel is added to the filtrate, the mixture is concentrated and the residue is purified chromatographically on silica gel (mobile phase: cyclohexane→cyclohexane/ethyl acetate 5:1). This gives 4.7 g (43% of theory) of the title compound.

$^1$H-NMR (300 MHz, CDCl$_3$): δ=12.00 (s, 1H), 6.25 (br. s, 1H), 5.96 (d, 1H), 5.93 (d, 1H), 2.86 (s, 2H), 2.40-2.25 (m, 2H), 2.22-2.10 (m, 2H), 2.00-1.86 (m, 1H), 1.80-1.62 (m, 1H).

MS (DCI): m/z=221 (M+H)$^+$, 238 (M+NH$_4$)$^+$.

Example 43A 5,7-Dihydroxyspiro[chromen-2,1'-cyclopropan]-4(3H)-one

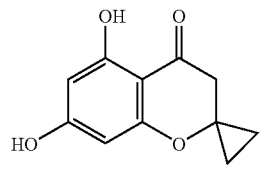

Under argon, 112 g (690 mmol) of 1,3,5-trihydroxybenzene dihydrate are dissolved in 230 ml abs. dimethylformamide, 28.82 g (230 mmol) of methyl cyclopropylideneacetate (Example 41A) and 20 g of 4 Å molecular sieve (as powder) are added and the mixture is stirred at a bath temperature of 130° C. overnight. 1 liter of 1 N hydrochloric acid is then added, and the mixture is extracted repeatedly with ethyl acetate. The combined organic phases are washed once with water and once with saturated sodium chloride solution, dried over sodium sulfate and concentrated. 230 ml (2.99 mol) of trifluoroacetic acid are added to the product obtained, and the mixture is heated to 75° C. and stirred for 8 hours. The mixture is then cooled, water is added and the mixture is extracted repeatedly with ethyl acetate. The combined organic phases are washed twice with saturated sodium chloride solution, dried over sodium sulfate, filtered and concentrated. The residue is purified on silica gel (mobile phase: dichloromethane/methanol 100:1→100:3). The product fractions are combined and concentrated. Dichloromethane is added to the residue obtained, the mixture is stirred briefly and the precipitate is filtered off with suction and dried under high vacuum. This gives 2.25 g (5% of theory) of the target compound. The mother liquor is then purified again on a silica gel column (mobile phase: dichloromethane/methanol 100:1). This gives a further 3.41 g (7% of theory) of the title compound.

$^1$H-NMR (400 MHz, CDCl$_3$): δ=12.08 (s, 1H), 6.61 (br. s, 1H), 5.99 (d, 1H), 5.88 (d, 1H), 2.77 (s, 2H), 1.08-1.04 (m, 2H), 0.71-0.66 (m, 2H).

MS (ESIpos): m/z=207 (M+H)$^+$.

Example 44A

5-Hydroxy-4-oxo-3,4-dihydrospiro[chromen-2,1'-cyclobutan]-7-yl trifluoromethanesulfonate

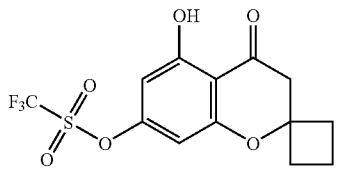

Under argon, 21.96 g (99.7 mmol) of 5,7-dihydroxyspiro[chromen-2,1'-cyclobutan]-4(3H)-one (Example 42A) are dissolved in 600 ml of abs. dimethylformamide. The mixture is cooled to 0° C., 15.16 g (109.7 mmol) of potassium carbonate are added and the mixture is stirred for 15 min and then cooled to −20° C. A solution of 37.41 g (104.7 mmol) of N,N-bis(trifluoromethanesulfonyl)-aniline in 200 ml of abs. dimethylformamide is slowly added dropwise. After a total of 5 hours of stirring, ammonium chloride solution is added to the mixture. The mixture is diluted with water and ethyl acetate, the organic phase is separated off and the aqueous phase is extracted two more times with ethyl acetate. The combined organic phases are washed twice with saturated sodium chloride solution, dried over magnesium sulfate, filtered and concentrated. The residue is adsorbed on silica gel and purified on a silica gel column (mobile phase: cyclohexane/ethyl acetate 30:1). This gives 28 g (80% of theory) of the title compound.

$^1$H-NMR (500 MHz, CDCl$_3$): δ=11.89 (s, 1H), 6.41 (s, 1H), 6.40 (s, 1H), 2.96 (s, 2H), 2.42-2.31 (m, 2H), 2.26-2.15 (m, 2H), 2.04-1.92 (m, 1H), 1.80-1.68 (m, 1H).

MS (ESIneg): m/z=351 (M−H)$^-$.

Example 45A

5-Hydroxy-4-oxo-3,4-dihydrospiro[chromen-2,1'-cyclopropan]-7-yl trifluoromethanesulfonate

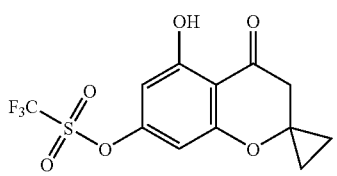

The target compound is prepared analogously to Example 44A from 5.5 g of the compound from Example 43A. This gives 5.4 g (60% of theory) of the target product.

$^1$H-NMR (400 MHz, CDCl$_3$): δ=11.95 (s, 1H), 6.48 (s, 1H), 6.33 (s, 1H), 2.88 (s, 2H), 1.18-1.09 (m, 2H), 0.80-0.72 (m, 2H).

Example 46A

5-Hydroxy-7-isopropylspiro[chromen-2,1'-cyclobutan]-4(3H)-one

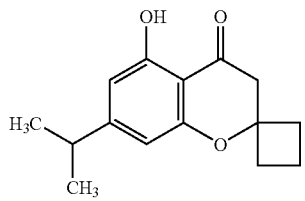

Under argon, 16 g (45.42 mmol) of 5-hydroxy-4-oxo-3,4-dihydrospiro[chromen-2,1'-cyclobutan]-7-yl trifluoromethanesulfonate (Example 44A), 3.71 g (4.54 mmol) of [1,1'-bis(diphenylphosphino)ferrocene]dichloropalladium (II) and 5.78 g (136.25 mmol) of lithium chloride are suspended in 400 ml of abs. dimethylformamide. The mixture is cooled to 0° C., 90.8 ml (90.8 mmol) of diisopropylzinc (1 M solution in toluene) are added and the mixture is stirred at this temperature for 4 hours. At 0° C., saturated ammonium chloride solution is then added to the mixture. The mixture is diluted with water, 1 N hydrochloric acid and ethyl acetate, the organic phase is separated off and the aqueous phase is extracted repeatedly with ethyl acetate. The combined organic phases are washed twice with water and once with saturated sodium chloride solution, dried over sodium sulfate, filtered and concentrated. The residue is adsorbed on silica gel and purified on a silica gel column (mobile phase: cyclohexane→cyclohexane/ethyl acetate 20:1). This gives 9.6 g (86% of theory) of the title compound.

$^1$H-NMR (500 MHz, CDCl$_3$): δ=11.59 (s, 1H), 6.38 (s, 1H), 6.32 (s, 1H), 2.88 (s, 2H), 2.80 (heptet, 1H), 2.38-2.29 (m, 2H), 2.20-2.12 (m, 2H), 1.98-1.89 (m, 1H), 1.78-1.68 (m, 1H), 1.21 (d, 6H).

MS (ESIpos): m/z=247 (M+H)$^+$.

Example 47A

5-Hydroxy-7-isopropylspiro[chromen-2,1'-cyclopropan]-4(3H)-one

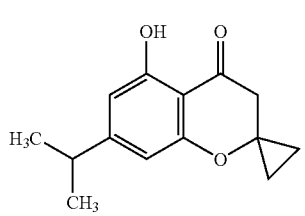

The title compound is prepared analogously to Example 46A from 5.4 g of 5-hydroxy-4-oxo-3,4-dihydrospiro[chromen-2,1'-cyclopropan]-7-yl trifluoromethanesulfonate (Example 45A). This gives 5.4 g (89% of theory) of the target product having a purity of about 87%.

$^1$H-NMR (400 MHz, CDCl$_3$): δ=11.67 (s, 1H), 6.42 (s, 1H), 6.27 (s, 1H), 2.83-2.73 (m, 3H), 1.21 (d, 6H), 1.11-1.05 (m, 2H), 0.72-0.66 (m, 2H).

MS (DCI): m/z=233 (M+H)$^+$, 250 (M+NH$_4$)$^+$.

The main imparity present is the n-propyl isomer:

5-hydroxy-7-propylspiro[chromen-2,1'-cyclopropan]-4(3H)-one

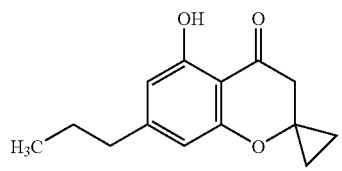

¹H-NMR (400 MHz, CDCl₃): δ=11.68 (s, 1H), 6.38 (s, 1H), 6.22 (s, 1H), 2.80 (s, 2H), 2.49 (t, 2H), 1.68-1.57 (m, 2H), 1.11-1.05 (m, 2H), 0.93 (t, 3H), 0.72-0.66 (m, 2H).

Example 48A

7-Cyclopentyl-5-hydroxyspiro[chromen-2,1'-cyclobutan]-4(3H)-one

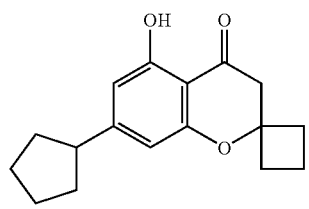

Under argon, 8.45 g (24.0 mmol) of 5-hydroxy-4-oxo-3,4-dihydrospiro[chromen-2,1'-cyclobutan]-7-yl trifluoromethanesulfonate (Example 44A), 3.92 g (4.8 mmol) of [1,1'-bis(diphenylphosphino)-ferrocene]dichloropalladium (II) and 6.10 g (144.0 mmol) of lithium chloride are suspended in 250 ml of abs. dimethylformamide. The mixture is cooled to 0° C., 216 ml (108 mmol) of (cyclopentyl)zinc bromide (0.5 M solution in tetrahydrofuran) are added and the mixture is stirred at room temperature overnight. Saturated ammonium chloride solution is then added to the mixture. The mixture is diluted with water, 1 N hydrochloric acid and ethyl acetate, the organic phase is separated off and the aqueous phase is extracted repeatedly with ethyl actate. The combined organic phases are washed twice with water and once with saturated sodium chloride solution, dried over sodium sulfate, filtered and concentrated. The residue is adsorbed on silica gel and purified on a silica gel column (mobile phase: cyclohexane→cyclohexane/ethyl acetate 10:1). This gives 6.2 g (94% of theory) of the title compound in a purity of 90%.

¹H-NMR (300 MHz, CDCl₃): δ=11.60 (s, 1H), 6.38 (s, 1H), 6.32 (s, 1H), 2.97-2.83 (m, 3H), 2.40-2.27 (m, 2H), 2.22-2.11 (m, 2H), 2.10-1.88 (m, 3H), 1.86-1.50 (m, 7H).

MS (ESIpos): m/z=273 (M+H)⁺.

Example 49A

5-Hydroxy-7-isopropyl-4-oxo-3,4-dihydrospiro[chromen-2,1'-cyclobutane]-6-carbaldehyde

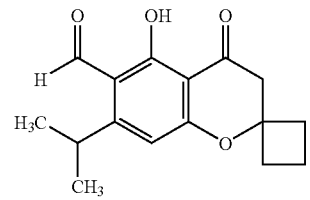

Under argon, 9.60 g (39 mmol) of 5-hydroxy-7-isopropyl-spiro[chromen-2,1'-cyclobutan]-4(3H)-one (Example 46A) are dissolved in 400 ml of abs. dichloromethane and cooled to −70° C. At this temperature, 97.44 ml (97.44 mmol) of titanium(IV) chloride (1 M solution in dichloromethane) are added dropwise such that the temperature does not exceed −65° C. The mixture is stirred briefly at −70° C., 3.88 ml (42.87 mmol) of dichloromethyl methyl ether are then added and the mixture is subsequently warmed to 0° C. After 3 hours at this temperature, the reaction mixture is added carefully to ice-water and extracted four times with dichloromethane. The combined organic phases are washed three times with saturated sodium chloride solution, dried over magnesium sulfate, filtered and evaporated to dryness. The crude product obtained is adsorbed on silica gel and purified on a silica gel column (mobile phase: cyclohexane→cyclohexane/ethyl acetate 30:1). This gives 8.1 g (76% of theory) of the title compound in a purity of 77%.

¹H-NMR (400 MHz, CDCl₃): δ=12.86-12.55 (br. s, 1H), 10.51 (s, 1H), 6.50 (s, 1H), 4.18-4.05 (m, 1H), 2.96 (s, 2H), 2.48-2.32 (m, 2H), 2.28-2.17 (m, 2H), 2.06-1.92 (m, 1H), 1.83-1.68 (m, 1H), 1.21 (d, 6H).

MS (DCI): m/z=275 (M+H)⁺, 292 (M+NH₄)⁺.

The main impurity present is the n-propyl isomer:

5-hydroxy-4-oxo-7-propyl-3,4-dihydrospiro[chromen-2,1'-cyclobutane]-6-carbaldehyde

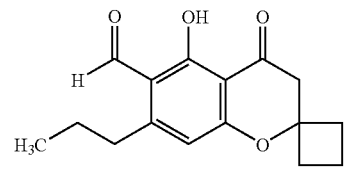

¹H-NMR (400 MHz, CDCl₃): δ=12.80-12.55 (br. s, 1H), 10.49 (s, 1H), 6.31 (s, 1H), 2.98-2.92 (m, 4H), 2.48-2.32 (m, 2H), 2.28-2.17 (m, 2H), 2.06-1.92 (m, 1H), 1.83-1.68 (m, 1H), 1.65-1.58 (m, 2H), 1.00 (t, 3H).

Example 50A

6-Formyl-7-isopropyl-4-oxo-3,4-dihydrospiro[chromen-2,1'-cyclobutan]-5-yl trifluoromethanesulfonate

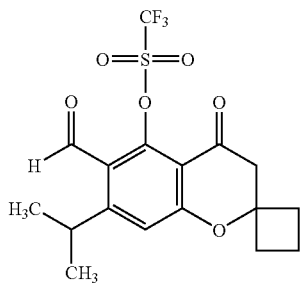

Under argon, 2.16 g (7.87 mmol) of 5-hydroxy-7-isopropyl-4-oxo-3,4-dihydrospiro[chromen-2,1'-cyclobutane]-6-carbaldehyde (Example 49A) are dissolved in 40 ml of abs. dimethylformamide. The mixture is cooled to 0° C., 1.2 g (8.66 mmol) of potassium carbonate are added, the mixture is stirred for 15 min and a solution of 3.16 g (8.66 mmol) of N,N-bis(trifluoromethanesulfonyl)-aniline in 38 ml of abs. dimethylformamide is slowly added dropwise at −20° C. The mixture is briefly stirred with cooling and then slowly warmed to room temperature. After a total of 4 hours, ammonium chloride solution is added, the mixture is diluted with water and ethyl acetate and the organic phase is separated off. The aqueous phase is extracted three times with ethyl acetate and the combined organic phases are washed twice with saturated sodium chloride solution, dried over magnesium sulfate, filtered and concentrated. The residue is adsorbed on silica gel and purified on a silica gel column (mobile phase: cyclohexane/ethyl acetate 50:1→20:1). This gives 1.42 g (42% of theory) of the title compound. A mixed fraction is re-purified on silica gel as described above. This gives a further 1.94 g (39% of theory) of the title compound having a purity of 65%.

$^1$H-NMR (300 MHz, CDCl$_3$): δ=10.36 (s, 1H), 7.10 (s, 1H), 4.02-3.87 (m, 1H), 2.96 (s, 2H), 2.48-2.33 (m, 2H), 2.29-2.19 (m, 2H), 2.06-1.90 (m, 1H), 1.85-1.68 (m, 1H), 1.24 (d, 6H).

MS (DCI): m/z=424 (M+NH$_4$)$^+$.

Example 51A 5-(4-Fluorophenyl)-7-isopropyl-4-oxo-3,4-dihydrospiro[chromen-2,1'-cyclobutane]-6-carbaldehyde

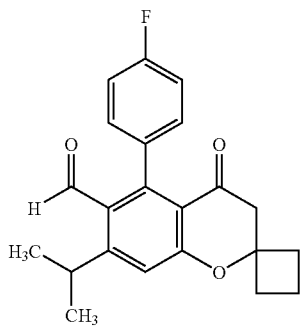

Under argon, 4.00 g (9.84 mmol) of 6-formyl-7-isopropyl-4-oxo-3,4-dihydrospiro[chromen-2,1'-cyclobutan]-5-yl trifluoromethanesulfonate (Example 50A), 1.79 g (12.8 mmol) of 4-fluorophenyl-boronic acid, 3.55 g (16.73 mmol) of tripotassium phosphate and 1.25 g (1.08 mmol) of tetrakis(triphenylphosphine)palladium(0) are initially charged and the apparatus is flushed by repeated evacuation and venting with argon. 100 ml of abs. dioxane are then added, the apparatus is closed and the mixture is heated under reflux. After stirring overnight, the mixture is cooled and filtered through a layer of silica gel, the filter cake is washed thoroughly with ethyl acetate and the filtrate is concentrated. The residue is adsorbed on silica gel and chromatographed on a silica gel column (mobile phase: cyclohexane→cyclohexane/ethyl acetate 25:1). The crude product obtained is triturated with hot petroleum ether and cooled slowly, and the precipitate is filtered off with suction. This gives 3.2 g of the target compound in a purity of about 90%.

The main impurity present is the n-propyl isomer:

5-(4-fluorophenyl)-4-oxo-7-propyl-3,4-dihydrospiro[chromen-2,1'-cyclobutane]-6-carbaldehyde

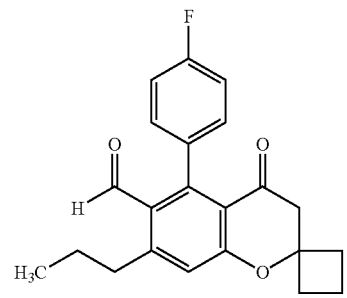

Subsequent chromatographic separation on a chiral phase [column: Daicel Chiralpak AD-H, 250×20 mm; mobile phase: ethanol/isohexane 30:70; flow rate: 15 ml/min; 22° C.; detection: 260 nm] gives 2.78 g (80% of theory) of the pure title compound.

R$_t$=4.12 min [column: Chiralpak AD-H, 250×4.6 mm; mobile phase: ethanol/isohexane 30:70; flow rate: 1 ml/min; detection: 260 nm].

$^1$H-NMR (400 MHz, CDCl$_3$): δ=9.59 (s, 1H), 7.16-7.07 (m, 5H), 3.98-3.88 (m, 1H), 2.81 (s, 2H), 2.46-2.34 (m, 2H), 2.26-2.16 (m, 2H), 2.02-1.89 (m, 1H), 1.78-1.60 (m, 1H), 1.28 (d, 6H).

MS (DCI): m/z=353 (M+H)$^+$, 370 (M+NH$_4$)$^+$.

Example 52A 5-(4-Fluorophenyl)-6-{hydroxy[4-(trifluoromethyl)phenyl]methyl}-7-isopropylspiro[chromen-2,1'-cyclobutan]-4(3H)-one

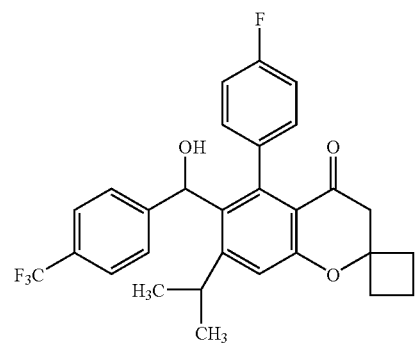

Under argon, 0.70 g (1.99 mmol) of 5-(4-fluorophenyl)-7-isopropyl-4-oxo-3,4-dihydrospiro-[chromen-2,1'-cyclobutane]-6-carbaldehyde (Example 51A) is suspended in 30 ml of tetrahydrofuran and cooled to −78° C. 5.25 ml (2.62 mmol) of a freshly prepared 0.5 M solution of [4-(trifluoromethyl)phenyl]magnesium bromide in tetrahydrofuran are added slowly. The mixture is stirred briefly at −78° C. and then warmed to 0° C. After about 30 min, the mixture is hydrolyzed with sodium bicarbonate solution, diluted with water and extracted repeatedly with ethyl acetate. The combined organic phases are washed twice with saturated sodium chloride solution, dried over sodium sulfate, filtered and concentrated. The crude product is purified a little at a time by preparative HPLC (method 12). This gives 0.635 g (64% of theory) of the title compound.

$^1$H-NMR (300 MHz, CDCl$_3$): δ=7.55 (d, 2H), 7.32 (d, 2H), 7.15-6.95 (m, 5H), 5.72 (s, 1H), 3.12-2.98 (m, 1H), 2.79 (s, 2H), 2.49-2.30 (m, 2H), 2.29 (d, 1H), 2.26-2.12 (m, 2H), 2.01-1.86 (m, 1H), 1.78-1.60 (m, 1H), 1.20 (d, 3H), 0.62 (d, 3H).

MS (DCI): m/z=499 (M+H)$^+$, 516 (M+NH$_4$)$^+$.

Example 53A 5-(4-Fluorophenyl)-6-{fluoro[4-(trifluoromethyl)phenyl]methyl}-7-isopropylspiro[chromen-2,1'-cyclobutan]-4(3H)-one

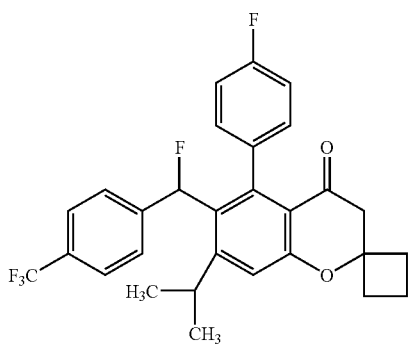

Under argon, 180 mg (0.32 mmol) of 5-(4-fluorophenyl)-6-{hydroxy[4-(trifluoromethyl)phenyl]-methyl}-7-isopropylspiro[chromen-2,1'-cyclobutan]-4(3H)-one (Example 52A) are dissolved in 3.2 ml of toluene, 52 µl (0.39 mmol) of diethylaminosulfur trifluoride are slowly added at −78° C. and the mixture is stirred at −78° C. for 1 h. The temperature is then slowly increased to −60° C. After 2 h, water is added and the mixture is extracted twice with ethyl acetate. The combined organic phases are washed once with saturated sodium bicarbonate solution and once with saturated sodium chloride solution, dried over sodium sulfate, filtered and concentrated. The crude product is purified on a silica gel column (mobile phase: cyclohexane/ethyl acetate 12:1). This gives 107 mg (66% of theory) of the title compound.

$^1$H-NMR (300 MHz, CDCl$_3$): δ=7.59 (d, 2H), 7.26 (d, 2H), 7.22-7.04 (m, 3H), 6.99-6.95 (m, 2H), 6.32 (d, 1H), 2.95-2.83 (m, 1H), 2.80 (s, 2H), 2.49-2.30 (m, 2H), 2.25-2.14 (m, 2H), 2.02-1.86 (m, 1H), 1.78-1.62 (m, 1H), 1.19 (d, 3H), 0.73 (d, 3H).

MS (DCI): m/z=501 (M+H)$^+$, 518 (M+NH$_4$)$^+$.

Example 54A 5-(4-Fluorophenyl)-7-isopropyl-6-[4-(trifluoromethyl)benzoyl]spiro[chromen-2,1'-cyclobutan]-4(3H)-one

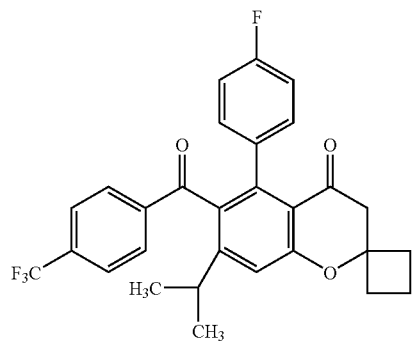

107 mg (0.25 mmol) of 1,1-dihydro-1,1,1-triacetoxy-1,2-benziodoxol-3(1H)-one are dissolved in 1 ml abs. of dichloromethane and cooled to −30° C. 14 µl (0.17 mmol) of pyridine are added, followed by the dropwise addition of 84 mg (0.17 mmol) of 5-(4-fluorophenyl)-6-{hydroxy[4-(trifluoromethyl)phenyl]methyl}-7-isopropylspiro[chromen-2,1'-cyclobutan]-4(3H)-one (Example 52A), dissolved in 0.6 ml of abs. dichloromethane. The mixture is slowly warmed to 0° C. and stirred at this temperature for 1.5 h. The mixture is diluted with ethyl acetate, 5 ml of 1 N aqueous sodium hydroxide solution are added and the mixture is then extracted twice with ethyl acetate. The combined organic phases are washed once with 1 N hydrochloric acid and twice with saturated sodium chloride solution, dried over magnesium sulfate, filtered and concentrated. The crude product obtained is dried under high vacuum and then reacted without further purification. This gives 89 mg (>100% of theory) of the title compound.

$^1$H-NMR (300 MHz, CDCl$_3$): δ=7.58 (q, 4H), 7.12-6.48 (m, 5H), 2.82 (s, 2H), 2.78-2.68 (m, 1H), 2.49-2.36 (m, 2H), 2.28-2.15 (m, 2H), 2.03-1.90 (m, 1H), 1.78-1.68 (m, 1H), 1.22 (br. s, 6H).

MS (DCI): m/z=497 (M+H)$^+$, 514 (M+NH$_4$)$^+$.

Example 55A

6-[(4-tert-Butylphenyl)(hydroxy)methyl]-5-(4-fluorophenyl)-7-isopropylspiro[chromen-2,1'-cyclo-butan]-4(3H)-one

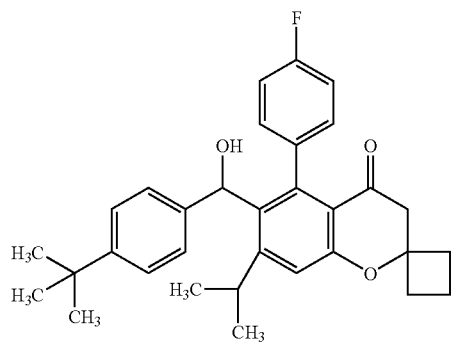

Under argon, 0.30 g (0.851 mmol) of 5-(4-fluorophenyl)-7-isopropyl-4-oxo-3,4-dihydrospiro-[chromen-2,1'-cyclobutane]-6-carbaldehyde (Example 51A) is suspended in 6 ml of tetrahydrofuran and cooled to −78° C. 2.54 ml (1.28 mmol) of a freshly prepared 0.5 M solution of [4-(tert-butyl)phenyl]magnesium bromide in tetrahydrofuran are added slowly. The mixture is briefly stirred at −78° C. and then warmed to 0° C. After about 1.5 h, saturated ammonium chloride solution is added and the mixture is diluted with a little 1 N hydrochloric acid and extracted repeatedly with ethyl acetate. The combined organic phases are washed twice with saturated sodium chloride solution, dried over sodium sulfate, filtered and concentrated. The crude product is purified a little at a time by preparative HPLC (method 12). This gives 0.239 g (58% of theory) of the title compound.

$^1$H-NMR (400 MHz, CDCl$_3$): δ=7.29 (d, 2H), 7.13-6.95 (m, 7H), 5.72 (s, 1H), 3.18 (heptet, 1H), 2.79 (s, 2H), 2.46-2.30 (m, 2H), 2.23-2.12 (m, 2H), 2.09-1.88 (m, 2H), 1.76-1.62 (m, 1H), 1.30 (s, 9H), 1.19 (d, 3H), 0.63 (d, 3H).

LC/MS (method 9): R$_t$=3.44 min

MS (ESIpos): m/z=487 (M+H)$^+$.

Example 56A

6-[(4-tert-Butylphenyl)(fluoro)methyl]-5-(4-fluorophenyl)-7-isopropylspiro[chromen-2,1'-cyclo-butan]-4(3H)-one

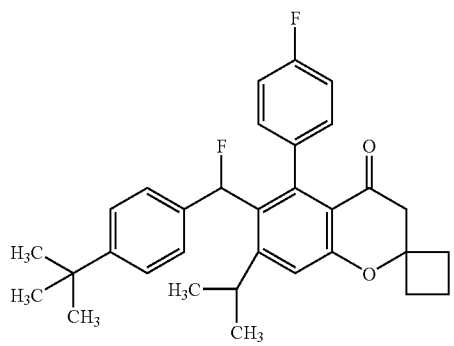

Under argon, 110 mg (0.23 mmol) of 6-[(4-tert-butylphenyl)(hydroxy)methyl]-5-(4-fluorophenyl)-7-isopropylspiro[chromen-2,1'-cyclobutan]-4(3H)-one (Example 55A) are dissolved in 2.3 ml of toluene, 36 μl (0.27 mmol) of diethylaminosulfur trifluoride are added slowly at −78° C. and the mixture is stirred at −78° C. for 1 h. The temperature is then slowly increased to −60° C. After 2 h, water is added and the mixture is extracted twice with ethyl acetate. The combined organic phases are washed once with saturated sodium bicarbonate solution and once with saturated sodium chloride solution, dried over sodium sulfate, filtered and concentrated. The crude product is purified on a silica gel column (mobile phase: cyclohexane/ethyl acetate 12:1). This gives 92 mg (83% of theory) of the title compound.

$^1$H-NMR (300 MHz, CDCl$_3$): δ=7.30 (d, 2H), 7.22-7.14 (m, 1H), 7.12-7.01 (m, 4H), 6.99-6.94 (m, 2H), 6.31 (d, 1H), 3.10-2.98 (m, 1H), 2.79 (s, 2H), 2.48-2.30 (m, 2H), 2.25-2.13 (m, 2H), 2.00-1.86 (m, 1H), 1.76-1.63 (m, 1H), 1.29 (s, 9H), 1.18 (d, 3H), 0.72 (d, 3H).

Example 57A 6-(4-tert.-Butylbenzoyl)-5-(4-fluorophenyl)-7-isopropylspiro[chromen-2,1'-cyclobutan]-4(3H)-one

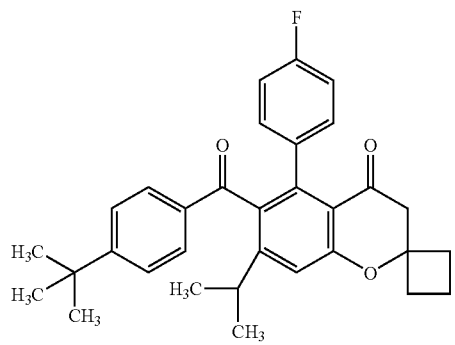

91 mg (0.21 mmol) of 1,1-dihydro-1,1,1-triacetoxy-1,2-benziodoxol-3(1H)-one are dissolved in 1.4 ml of abs. dichloromethane and cooled to −30° C. 12 μl (0.14 mmol) of pyridine are added, followed by the dropwise addition of 68 mg (0.14 mmol) of 6-[(4-tert-butylphenyl)(hydroxy)-methyl]-5-(4-fluorophenyl)-7-isopropylspiro[chromen-2,1'-cyclobutan]-4(3H)-one (Example 55A), dissolved in 0.6 ml of abs. dichloromethane. The mixture is slowly warmed to 0° C. and stirred at this temperature for 1.5 h. The mixture is diluted with ethyl acetate, 5 ml of 1 N aqueous sodium hydroxide solution are added and the mixture is then extracted twice with ethyl acetate. The combined organic phases are washed once with 1 N hydrochloric acid and twice with saturated sodium chloride solution, dried over magnesium sulfate, filtered and concentrated. The crude product is dried under high vacuum and then reacted without further purification. This gives 81 mg (>100% of theory) of the title compound.

Example 58A 5-(4-Fluorophenyl)-6-{hydroxy[4-(trifluoromethoxy)phenyl]methyl}-7-isopropylspiro[chromen-2,1'-cyclobutan]-4(3H)-one

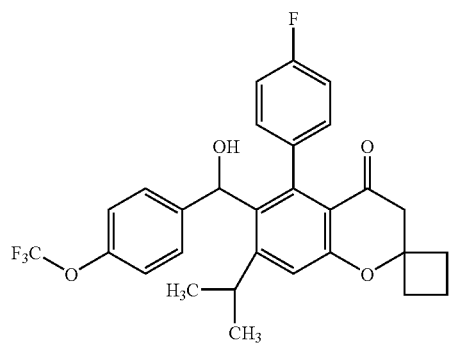

Under argon, 0.60 g (1.70 mmol) of 5-(4-fluorophenyl)-7-isopropyl-4-oxo-3,4-dihydrospiro-[chromen-2,1'-cyclobutane]-6-carbaldehyde (Example 51A) is suspended in 15 ml of tetrahydrofuran and cooled to −70° C. 4.3 ml (2.13 mmol) of a freshly prepared 0.5 M solution of [4-(trifluoromethoxy)

phenyl]magnesium bromide in tetrahydrofuran are added slowly. The mixture is stirred briefly at −78° C. and then warmed to 0° C. After 1 h, the mixture is hydrolyzed with sodium bicarbonate solution, diluted with water and extracted repeatedly with ethyl acetate. The combined organic phases are washed twice with saturated sodium chloride solution, dried over sodium sulfate, filtered and concentrated. The crude product is purified on a silica gel column (mobile phase: cyclohexane/ethyl acetate 25:1→10:1). This gives 710 mg (81% of theory) of the title compound in a purity of 70%.

$^1$H-NMR (400 MHz, CDCl$_3$): δ=7.22 (d, 2H), 7.15-6.97 (m, 7H), 5.71 (d, 1H), 3.11 (heptet, 1H), 2.79 (s, 2H), 2.47-2.30 (m, 2H), 2.23-2.13 (m, 2H), 2.11 (d, 1H), 1.99-1.88 (m, 1H), 1.76-1.63 (m, 1H), 1.19 (d, 3H), 0.64 (d, 3H).

MS (DCI): m/z=515 (M+H)$^+$, 532 (M+NH$_4$)$^+$.

Example 59A 5-(4-Fluorophenyl)-6-{fluoro[4-(trifluoromethoxy)phenyl]methyl}-7-isopropylspiro[chromen-2,1'-cyclobutan]-4(3H)-one

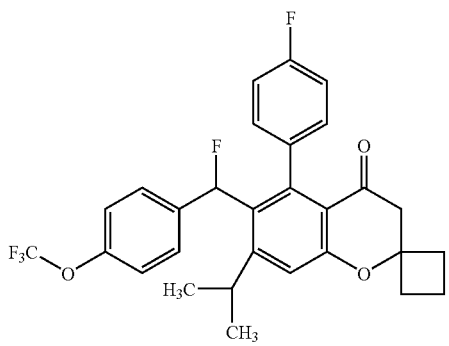

Under argon, 159 mg (0.31 mmol) of 5-(4-fluorophenyl)-6-{hydroxy[4-(trifluoromethoxy)phenyl]-methyl}-7-isopropylspiro[chromen-2,1'-cyclobutan]-4(3H)-one (Example 58A) are dissolved in 3.1 ml of toluene, 49 μl (0.37 mmol) of diethylaminosulfur trifluoride are slowly added at −78° C. and the mixture is stirred at −78° C. for 2 h. Water is then added, and the mixture is extracted twice with ethyl acetate. The combined organic phases are washed once with saturated sodium bicarbonate solution and once with saturated sodium chloride solution, and dried over sodium sulfate, filtered and concentrated. The crude product is purified on a silica gel column (mobile phase:cyclohexane/ethyl acetate 15:1). This gives 118 mg (74% of theory) of the title compound.

$^1$H-NMR (400 MHz, CDCl$_3$): δ=7.20-7.04 (m, 7H), 7.02-6.92 (m, 2H), 6.31 (d, 1H), 2.94 (heptet, 1H), 2.79 (s, 2H), 2.48-2.31 (m, 2H), 2.25-2.13 (m, 2H), 2.00-1.89 (m, 1H), 1.78-1.62 (m, 1H), 1.18 (d, 3H), 0.78 (d, 3H).

MS (DCI): m/z=517 (M+H)$^+$, 534 (M+NH$_4$)$^+$.

Example 60A 5-(4-Fluorophenyl)-7-isopropyl-6-[4-(trifluoromethoxy)benzoyl]spiro[chromen-2,1'-cyclobutan]-4(3H)-one

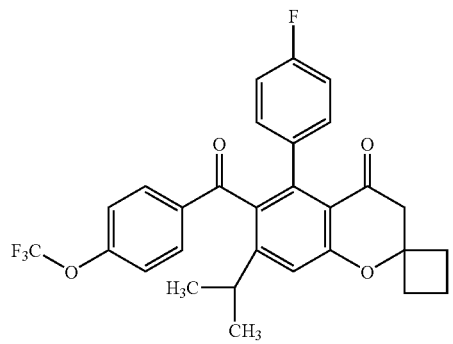

68 mg (0.16 mmol) of 1,1-dihydro-1,1,1-triacetoxy-1,2-benziodoxol-3(1H)-one are dissolved in 0.6 ml of abs. dichloromethane and cooled to −30° C. 9 μl (0.11 mmol) of pyridine are added, followed by the dropwise addition of 55 mg (0.11 mmol) of 5-(4-fluorophenyl)-6-{hydroxy[4-(trifluoromethoxy)phenyl]methyl}-7-isopropylspiro-[chromen-2,1'-cyclobutan]-4(3H)-one (Example 58A), dissolved in 0.4 ml of abs. dichloromethane. The mixture is slowly warmed to 0° C. and stirred at this temperature for 6 h. The mixture is diluted with ethyl acetate, 5 ml of 1 N aqueous sodium hydroxide solution are added and the mixture is then extracted twice with ethyl acetate. The combined organic phases are washed once with 1 N hydrochloric acid and twice with saturated sodium chloride solution, dried over magnesium sulfate, filtered and concentrated. The crude product is dried under high vacuum and then reacted without further purification. This gives 54 mg (98% of theory) of the title compound.

Example 61A

5-Cyclopent-1-en-1-yl-7-isopropyl-4-oxo-3,4-dihydrospiro[chromen-2,1'-cyclobutane]-6-carbaldehyde

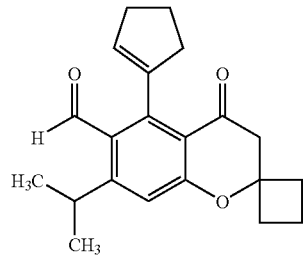

The title compound is prepared analogously to the procedure of Example 34A.

LC/MS (method 8): R$_t$=3.20 min

MS (ESIpos): m/z=325 (M+H)$^+$ $^1$H-NMR (CDCl$_3$, 300 MHz): δ=1.23 (d, 6H), 1.65-1.78 (m, 1H), 1.85-2.00 (m, 2H), 2.05-2.73 (m, 9H), 2.86 (s, 2H), 3.86-3.97 (m, 1H), 5.51-5.58 (m, 1H), 6.97 (s, 1H), 9.97 (s, 1H).

Example 62A rac-5-Cyclopent-1-en-1-yl-6-{hydroxy[4-(trifluoromethyl)phenyl]methyl}-7-isopropylspiro-[chromen-2,1'-cyclobutan]-4(3H)-one

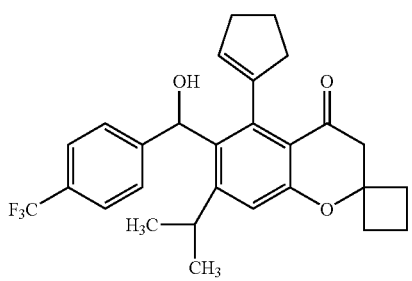

The title compound is prepared analogously to the procedure of Example 36A.

LC/MS (method 8): $R_t$=3.35 min
MS (ESIpos): m/z=471 (M+H)$^+$
MS (DCI): m/z=471 (M+H)$^+$, 488 (M+NH$_4$)$^+$
$^1$H-NMR (CDCl$_3$, 300 MHz): δ=0.44-0.70 (m, 3H), 1.06-1.21 (m, 3H), 1.60-1.80 (m, 1H), 1.83-2.05 (m, 2H), 2.06-2.64 (m, 9H), 2.69-2.93 (m, 3H), 2.94-3.12 (m, 1H), 5.38-5.51 (m, 1H), 6.14-6.24 (m, 1H), 6.89 (s, 1H), 7.31-7.47 (m, 2H), 7.56 (d, 2H).

Example 63A rac-5-Cyclopentyl-6-{hydroxy[4-(trifluoromethyl)phenyl]methyl}-7-isopropylspiro[chromen-2,1'-cyclobutan]-4(3H)-one

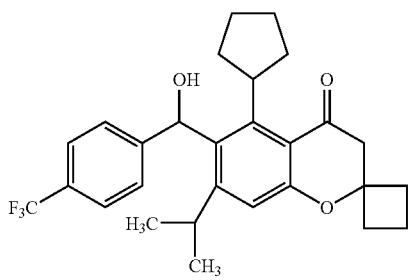

63 mg (0.031 mmol) of rhodium-on-carbon (5%) are added to a solution of 289 mg (0.61 mmol) of rac-5-cyclopent-1-en-1-yl-6-{hydroxy[4-(trifluoromethyl)phenyl]methyl}-7-isopropylspiro[chromen-2,1'-cyclobutan]-4(3H)-one (Example 62A) in 10 ml of ethanol, and the mixture is hydrogenated under a hydrogen pressure of 60 bar at room temperature for 18 h. For work-up, the suspension is filtered through kieselguhr, the filter cake is washed with ethyl acetate and the filtrate is concentrated under reduced pressure. The residue is taken up in 10 ml of ethanol, the same amount of rhodium-on-carbon is added again and the mixture is hydrogenated under a hydrogen pressure of 60 bar at room temperature for a further 18 h. The suspension is again filtered through kieselguhr, the filter cake is washed with ethyl acetate and the filtrate is concentrated under reduced pressure. The crude product is purified by chromatography on silica gel (mobile phase: cyclohexane/ethyl acetate 15:1).

Yield: 116 mg (40% of theory)
LC/MS (method 7): $R_t$=3.23 min
MS (ESIpos): m/z=473 (M+H)$^+$
$^1$H-NMR (CDCl$_3$, 300 MHz): δ=0.52-0.78 (m, 3H), 1.13 (d, 3H), 1.58-2.45 (m, 15H), 2.92 (s, 2H), 2.94-3.07 (m, 1H), 4.29-4.67 (br. m, 1H), 6.25-6.32 (m, 1H), 6.82 (s, 1H), 7.39 (d, 2H), 7.56 (d, 2H).

Example 64A rac-5-Cyclopentyl-6-{fluoro[4-(trifluoromethyl)phenyl]methyl}-7-isopropylspiro[chromen-2,1'-cyclobutan]-4(3H)-one

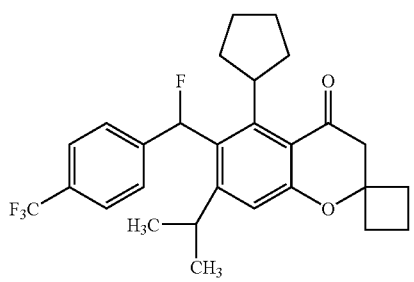

The title compound is prepared analogously to the procedure of Example 28A.

Yield: 192 mg (96% of theory)
LC/MS (method 7): $R_t$=3.42 min
MS (ESIpos): m/z=475 (M+H)$^+$
$^1$H-NMR (CDCl$_3$, 400 MHz): δ=0.72 (d, 3H), 1.11 (d, 3H), 1.58-2.45 (m, 14H), 2.79-2.99 (m, 3H), 4.38-4.53 (m, 1H), 6.84 (s, 1H), 6.96 (d, 1H), 7.33 (d, 2H), 7.59 (d, 2H).

WORKING EXAMPLES

Example 1 and Example 2

(4S)-7-Cyclopentyl-5-(4-fluorophenyl)-6-{(S)-hydroxy[4-(trifluoromethyl)phenyl]methyl}-2,2-dimethylchroman-4-ol (Example 1)

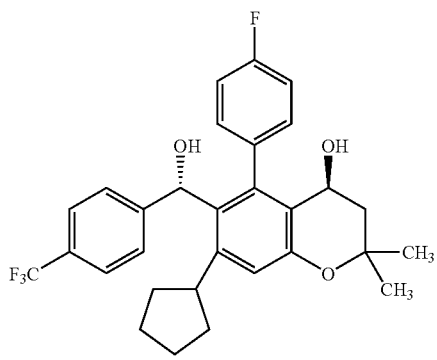

and (4S)-7-cyclopentyl-5-(4-fluorophenyl)-6-{(R)-hydroxy[4-(trifluoromethyl)phenyl]methyl}-2,2-dimethylchroman-4-ol (Example 2)

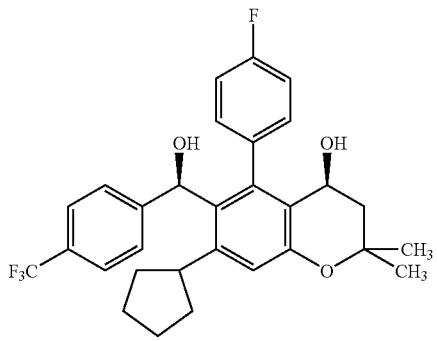

Under argon, 120 mg (0.23 mmol) of [(4S)-7-cyclopentyl-5-(4-fluorophenyl)-4-hydroxy-2,2-dimethyl-3,4-dihydro-2H-chromen-6-yl][4-(trifluoromethyl)phenyl]methanone (Example 12A) are initially charged in 2 ml of abs. toluene and cooled to −78° C. At this temperature, 0.59 ml (0.59 mmol) of diisobutylaluminum hydride solution (1 M in toluene) is slowly added dropwise, and stirring of the mixture is then continued at −78° C. for 2 h. Diisobutylaluminum hydride is then added in such an amount that no more starting material can be detected. Saturated potassium sodium tartrate solution is then added, and the mixture is diluted with water and extracted with ethyl acetate. The combined organic phases are washed once with saturated sodium chloride solution. The organic phase is dried over sodium sulfate, filtered and concentrated. The residue is purified by thick-layer chromatography (mobile phase: cyclohexane/ethyl acetate 5:1), resulting in the separation of the diastereomers.

Example 1

Yield: 62 mg (52% of theory)

$^1$H-NMR (400 MHz, CDCl$_3$): δ=7.51 (d, 2H), 7.35-7.27 (m, 3H), 7.18-7.02 (m, 3H), 6.89 (s, 1H), 5.69 (br. s, 1H), 4.57-4.52 (m, 1H), 3.03 (heptet, 1H), 2.09-1.95 (m, 4H), 1.78-1.53 (m, 5H), 1.52 (s, 3H), 1.42 (s, 3H), 1.36-1.24 (m, 2H).

MS (DCI): m/z=532 (M+NH$_4$)$^+$.

Example 2

Yield: 56 mg (46% of theory)

$^1$H-NMR (400 MHz, CDCl$_3$): δ=7.50 (d, 2H), 7.38-7.30 (m, 1H), 7.28 (d, 2H), 7.22-7.18 (m, 1H), 7.17-7.08 (m, 2H), 6.89 (s, 1H), 5.62 (br. s, 1H), 4.57-4.52 (m, 1H), 3.03 (heptet, 1H), 2.11 (d, 1H), 2.09-1.95 (m, 3H), 1.78-1.51 (m, 5H), 1.47 (s, 3H), 1.43 (s, 3H), 1.30-1.20 (m, 2H).

MS (DCI): m/z=532 (M+NH)$^+$.

Example 3

(4S)-7-Cyclopentyl-5-(4-fluorophenyl)-6-{(S)-fluoro[4-(trifluoromethyl)phenyl]methyl}-2,2-dimethylchroman-4-ol

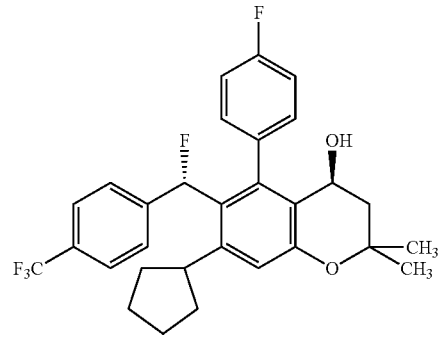

Under argon, 21 mg (0.033 mmol) of tert-butyl[((4S)-7-cyclopentyl-5-(4-fluorophenyl)-6-{fluoro[4-(trifluoromethyl)phenyl]methyl}-2,2-dimethyl-3,4-dihydro-2H-chromen-4-yl)oxy]dimethylsilane (Example 15A) are dissolved in 0.5 ml of tetrahydrofuran, 0.17 ml (0.17 mmol) of TBAF solution (1 M in tetrahydrofuran) is added and the mixture is stirred at room temperature. After 1 h, 1.5 ml of 0.2 N hydrochloric acid are added, and the mixture is repeatedly extracted with ethyl acetate. The combined organic phases are washed twice with saturated sodium chloride solution, dried over sodium sulfate, filtered and concentrated. The crude product is purified by preparative HPLC. The gives 11 mg (63% of theory) of the target compound having a de of 88%. Subsequent chromatographic separation of the isomers on a chiral phase [column: Chiralpak AD-H, 250×8 mm; mobile phase: isopropanol/isohexane 10:90; flow rate: 3 ml/min; 24° C.; detection: 254 nm] gives 4 mg of the diastereomerically pure compound.

R$_t$=4.54 min [Chiralpak IA, 250×4.6 mm; mobile phase: isopropanol/isohexane 3:97; flow rate: 1.5 ml/min; detection: 254 nm].

$^1$H-NMR (300 MHz, CDCl$_3$): δ=7.52 (d, 2H), 7.42-7.35 (m, 1H), 7.20 (d, 2H), 7.18-7.06 (m, 3H), 6.92 (s, 1H), 6.28 (d, 1H), 4.57 (q, 1H), 2.92 (heptet, 1H), 2.13-1.98 (m, 3H), 1.80-1.42 (m, 1H), 1.33-1.24 (m, 2H).

MS (ESIpos): m/z=499 (M−H$_2$O)$^+$.

Example 4

[(4S)-5-(4-Fluorophenyl)-4-hydroxy-7-isopropyl-2,2-dimethyl-3,4-dihydro-2H-chromen-6-yl][4-(trifluoromethyl)phenyl]methanone

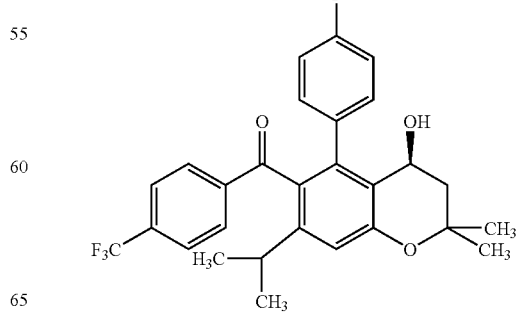

120 µl (680 µmol) of borane/N,N-diethylaniline complex are added slowly to a solution of 3.79 mg (30 µmol) of (1R,2S)-1-aminoindan-2-ol in 4 ml of tetrahydrofuran. The mixture is then cooled to 0° C., and a solution of 82 mg (170 µmol) of 5-(4-fluorophenyl)-7-isopropyl-2,2-dimethyl-6-[4-(trifluoromethyl)benzoyl]-2,3-dihydro-4H-chromen-4-one (Example 23A) in 4 ml of tetrahydrofuran is then slowly added dropwise. The mixture is allowed to thaw slowly and stirred at room temperature overnight. Methanol is then added, and the solvent is removed under reduced pressure. The residue is taken up in ethyl acetate and washed in each case twice with 1 M hydrochloric acid and saturated sodium bicarbonate solution and once with saturated sodium chloride solution. The organic phase is dried over sodium sulfate and then concentrated under reduced pressure. Purification of the residue by column chromatography on silica gel (mobile phase: gradient cyclohexane→cyclohexane/ethyl acetate 10:1) gives the target compound.

Yield: 65 mg (79% of theory, 91% ee)
HPLC (method 4): $R_f$=3.83 min
LC/MS (method 8): $R_t$=2.81 min
MS (ESIpos): m/z=487 (M+H)$^+$
$^1$H-NMR (CDCl$_3$, 300 MHz): δ=1.15 (d, 3H), 1.21 (d, 3H), 1.45 (s, 3H), 1.51 (s, 3H), 2.03 (d, 2H), 2.59-2.77 (m, 1H), 4.61-4.78 (m, 1H), 6.68-7.22 (m, 4H), 6.93 (s, 1H), 7.53 (d, 2H), 7.63 (d, 2H).

Example 5 and Example 6

(4S)-5-(4-Fluorophenyl)-6-{(S)-hydroxy[4-(trifluoromethyl)phenyl]methyl}-7-isopropyl-2,2-di-methyl-chroman-4-ol (Example 5)

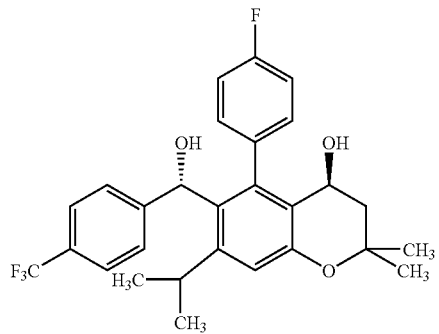

and (4S)-5-(4-fluorophenyl)-6-{(R)-hydroxy[4-(trifluoromethyl)phenyl]methyl}-7-isopropyl-2,2-di-methyl-chroman-4-ol (Example 6)

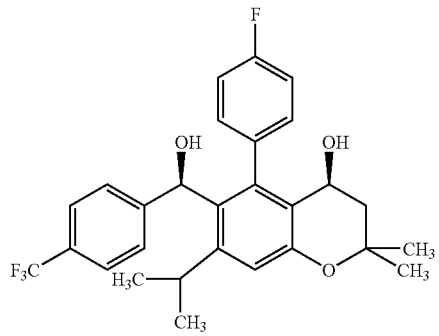

340 µl (1.89 mmol) of borane/N,N-diethylaniline complex are added slowly to a solution of 10.58 mg (70 µmol) of (1R,2S)-1-aminoindan-2-ol in ±1 ml of tetrahydrofuran, and the mixture is stirred for another 30 min. A solution of 230 mg (0.47 mmol) of rac-5-(4-fluorophenyl)-6-{hydroxy[4-(trifluoromethyl)phenyl]methyl}-7-isopropyl-2,2-dimethyl-2,3-dihydro-4H-chromen-4-one (Example 21A) in 11 ml of tetrahydrofuran are then very slowly added dropwise, and the mixture is stirred overnight. Methanol is then added, and the solvent is removed under reduced pressure. The residue is taken up in ethyl acetate and washed in each case twice with 1 M hydrochloric acid and saturated sodium bicarbonate solution and once with saturated sodium chloride solution. The organic phase is dried over sodium sulfate and then concentrated under reduced pressure. Purification of the residue by column chromatography on silica gel (mobile phase: gradient cyclohexane/dichloromethane/ethyl acetate 40:40:1→2:2:1) gives the diastereomerically pure target compounds.

Example 5

Yield: 119 mg (52% of theory, 91% ee)
HPLC (method 6): $R_t$=12.30 min
LC/MS (method 9): $R_t$=3.10 min
MS (DCI): m/z=506 (M+NH$_4$)$^+$
$^1$H-NMR (CDCl$_3$, 300 MHz): δ=0.72 (d, 3H), 1.18 (d, 3H), 1.42 (s, 3H), 1.49 (s, 3H), 1.99 (d, 2H), 2.03 (d, 1H), 2.90-3.08 (m, 1H), 4.54 (dd, 1H), 5.61-5.69 (m, 1H), 6.89 (s, 1H), 7.01-7.22 (m, 3H), 7.28-7.41 (m, 3H), 7.52 (d, 2H).

Example 6

Yield: 120 mg (52% of theory, 91% ee)
HPLC (method 6): $R_t$=14.45 min
LC/MS (method 9): $R_t$=3.16 min
MS (DCI): m/z=506 (M+NH$_4$)$^+$
$^1$H-NMR (CDCl$_3$, 300 MHz): δ=0.62 (d, 3H), 1.18 (d, 3H), 1.44 (s, 3H), 1.47 (s, 3H), 1.95-2.18 (m, 3H), 2.92-3.08 (m, 1H), 4.51-4.62 (m, 1H), 5.58-5.68 (m, 1H), 6.88 (s, 1H), 7.03-7.42 (m, 6H), 7.50 (d, 2H).

Example 7 and Example 8

(4S)-5-(4-Fluorophenyl)-6-{(S)-fluoro[4-(trifluoromethyl)phenyl]methyl}-7-isopropyl-2,2-dimethyl-chroman-4-ol (Example 7)

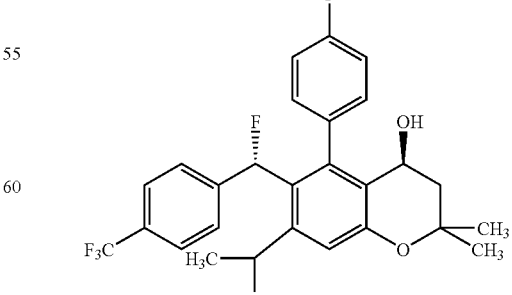

and (4S)-5-(4-fluorophenyl)-6-{(R)-fluoro[4-(trifluoromethyl)phenyl]methyl}-7-isopropyl-2,2-dimethylchroman-4-ol (Example 8)

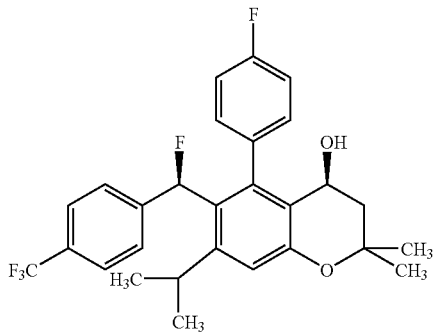

110 µl (630 µmol) of borane/N,N-diethylaniline complex are added slowly to a solution of 3.5 mg (20 µmol) of (1R, 2S)-1-aminoindan-2-ol in 4 ml of tetrahydrofuran, and the mixture is stirred at room temperature for 30 min. A solution of 77 mg (160 µmol) of 5-(4-fluorophenyl)-6-{(S)-fluoro[4-(trifluoromethyl)phenyl]methyl}-7-isopropyl-2,2-dimethyl-2,3-dihydro-4H-chromen-4-one (Example 22A) in 4 ml of tetrahydrofuran are then slowly added dropwise, and the mixture is stirred at room temperature for 6.5 h. Methanol is then added, and the solvent is removed under reduced pressure. The residue is taken up in ethyl acetate and washed in each case twice with 1 M hydrochloric acid and saturated sodium bicarbonate solution and once with saturated sodium chloride solution. The organic phase is dried over sodium sulfate and then concentrated under reduced pressure. Purification of the residue by column chromatography on silica gel (mobile phase: cyclohexane/ethyl acetate 20:1) gives the diastereomerically pure target compounds.

Example 7

Yield: 11 mg (14% of theory, 82% ee)
HPLC (method 4): $R_t$=3.52 min
LC/MS (method 8): $R_t$=2.96 min
MS (DCI): m/z=508 (M+NH$_4$)$^+$
$^1$H-NMR (CDCl$_3$, 300 MHz): δ=0.82 (d, 3H), 1.14 (d, 3H), 1.41 (s, 3H), 1.49 (s, 3H), 1.98 (d, 2H), 2.78-2.93 (m, 1H), 4.58 (dd, 1H), 6.26 (d, 1H), 6.91 (s, 1H), 6.97-7.28 (m, 6H), 7.52 (d, 2H).

Example 8

Yield: 10 mg (13% of theory, 86% ee)
HPLC (method 4): $R_t$=3.63 min
LC/MS (method 8): $R_t$=2.93 min
MS (DCI): m/z=508 (M+NH$_4$)$^+$
$^1$H-NMR (CDCl$_3$, 300 MHz): δ=0.73 (d, 3H), 1.18 (d, 3H), 1.45 (s, 3H), 1.48 (s, 3H), 1.97-2.03 (m, 2H), 2.78-2.96 (m, 1H), 4.55 (dd, 1H), 6.28 (d, 1H), 6.92 (s, 1H), 7.02-7.44 (m, 6H), 7.52 (d, 2H).

Example 9

(4S)-5-(4-Fluorophenyl)-7-isopropyl-2,2-dimethyl-6-[4-(trifluoromethyl)benzyl]chroman-4-ol

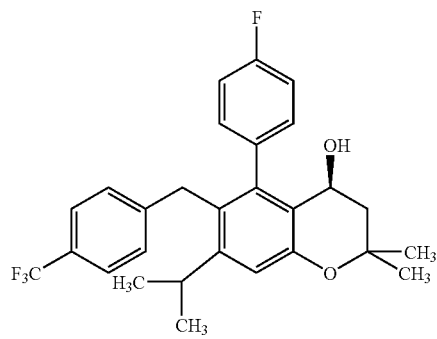

87 µl (490 µmol) of borane/N,N-diethylaniline complex are added slowly to a solution of 2.8 mg (20 µmol) of (1R, 2S)-1-aminoindan-2-ol in 3 ml of tetrahydrofuran, and the mixture is stirred at room temperature for 30 min. A solution of 60 mg (120 µmol) of 5-(4-fluorophenyl)-6-{(S)-fluoro[4-(trifluoromethyl)phenyl]methyl}-7-isopropyl-2,2-dimethyl-2,3-dihydro-4H-chromen-4-one (Example 22A) in 3 ml of tetrahydrofuran are then slowly added dropwise, and the mixture is stirred at room temperature for 3 days. Methanol is then added, and the solvent is removed under reduced pressure. The residue is taken up in ethyl acetate and washed in each case twice with 1 M hydrochloric acid and saturated sodium bicarbonate solution and once with saturated sodium chloride solution. The organic phase is dried over sodium sulfate and then concentrated under reduced pressure. Purification of the residue by column chromatography on silica gel (mobile phase:cyclohexane/ethyl acetate 20:1) gives the target compound.
Yield: 22 mg (36% of theory)
HPLC (method 4): $R_t$=3.38 min
LC/MS (method 9): $R_t$=3.42 min
MS (ESIpos): m/z=473 (M+H)$^+$
$^1$H-NMR (CDCl$_3$, 300 MHz): δ=1.12 (d, 3H), 1.16 (d, 3H), 1.43 (s, 3H), 1.48 (s, 3H), 1.98 (d, 2H), 2.78-2.98 (m, 1H), 3.71 (d, 1H), 3.80 (d, 1H), 4.56 (dd, 1H), 6.97-7.28 (m, 6H), 7.52 (d, 2H).

Example 10

[(4S)-5-(4-Fluorophenyl)-4-hydroxy-7-isopropyl-2,2-dimethyl-3,4-dihydro-2H-chromen-6-yl][4-(trifluoromethoxy)phenyl]methanone

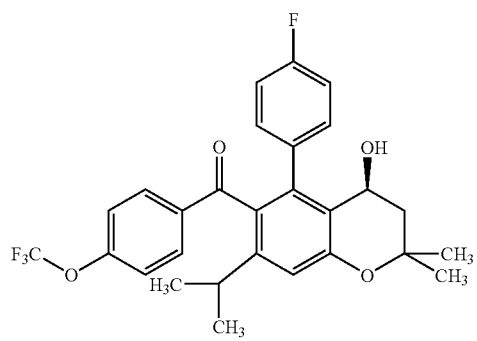

97 μl (540 μmol) of borane/N,N-diethylaniline complex are added slowly to a solution of 3.04 mg (20 μmol) of (1R,2S)-1-aminoindan-2-ol in 2.5 ml of tetrahydrofuran. The mixture is then cooled to 0° C., and a solution of 68 mg (140 μmol) of 5-(4-fluorophenyl)-7-isopropyl-2,2-dimethyl-6-[4-(trifluoromethoxy)benzoyl]-2,3-dihydro-4H-chromen-4-one (Example 26A) in 4 ml of tetrahydrofuran is then slowly added dropwise. The mixture is allowed to thaw slowly and stirred at room temperature overnight. To bring the reaction to completion, the reaction mixture is again cooled to 0° C., and a further 97 μl (540 μmol) of borane/N,N-diethylaniline complex are added. The mixture is then thawed slowly to room temperature and stirred at this temperature overnight. Methanol is then added, and the solvent is removed under reduced pressure. The residue is taken up in ethyl acetate and washed in each case twice with 1 M hydrochloric acid and saturated sodium bicarbonate solution and once with saturated sodium chloride solution. The organic phase is dried over sodium sulfate and then concentrated under reduced pressure. Purification of the residue by preparative HPLC (method 1) and subsequent chiral HPLC (method 2) gives the target compound.

Yield: 30 mg (44% of theory, 99.5% ee)

HPLC (method 4): $R_t$=5.20 min

LC/MS (method 8): $R_t$=3.28 min

MS (ESIpos): m/z=503 (M+H)$^+$ $^1$H-NMR (CDCl$_3$, 300 MHz): δ=1.17 (d, 3H), 1.21 (d, 3H), 1.46 (s, 3H), 1.51 (s, 3H), 2.02 (d, 2H), 2.62-2.79 (m, 1H), 4.71 (s, 1H), 6.61-7.23 (m, 7H), 7.56 (d, 2H).

In addition, in a second fraction, the enantiomer of the target product, [(4R)-5-(4-fluorophenyl)-4-hydroxy-7-isopropyl-2,2-dimethyl-3,4-dihydro-2H-chromen-6-yl][4-(trifluoromethoxy)phenyl]-methanone, is obtained:

Yield: 9 mg (13% of theory, 88% ee)

HPLC (method 4): $R_t$=8.06 min.

Example 11 and Example 12

(4S)-5-(4-Fluorophenyl)-6-{(S)-hydroxy[4-(trifluoromethoxy)phenyl]methyl}-7-isopropyl-2,2-di-methylchroman-4-ol (Example 11)

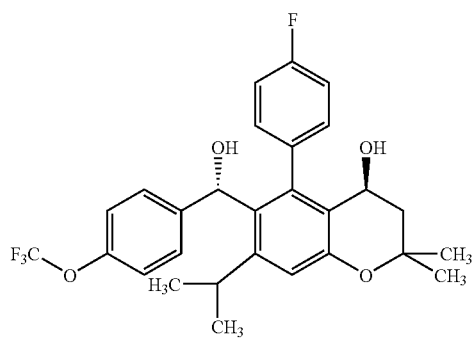

and (4S)-5-(4-fluorophenyl)-6-{(R)-hydroxy[4-(trifluoromethoxy)phenyl]methyl}-7-isopropyl-2,2-di-methylchroman-4-ol (Example 12)

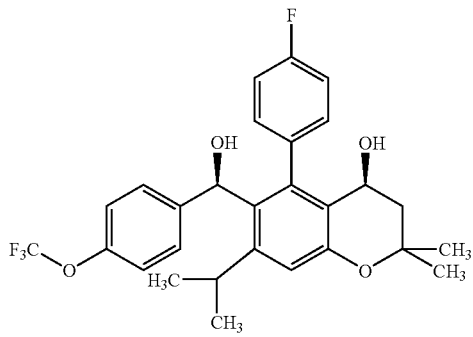

140 μl (800 μmol) of borane/N,N-diethylaniline complex are added slowly to a solution of 4.45 mg (30 μmol) of (1R,2S)-1-aminoindan-2-ol in 5 ml of tetrahydrofuran. The mixture is then cooled to 0° C., and a solution of 100 mg (200 μmol) of rac-5-(4-fluorophenyl)-6-{hydroxy[4-(trifluoromethoxy)phenyl]methyl}-7-isopropyl-2,2-dimethyl-2,3-dihydro-4H-chromen-4-one (Example 24A) in 5 ml of tetrahydrofuran is then slowly added dropwise. The mixture is allowed to thaw slowly and stirred at room temperature overnight. Methanol is then added, and the solvent is removed under reduced pressure. The residue is taken up in ethyl acetate and washed in each case twice with 1 M hydrochloric acid and saturated sodium bicarbonate solution and once with saturated sodium chloride solution. The organic phase is dried over sodium sulfate and then concentrated under reduced pressure. Purification of the residue by preparative HPLC (method 1) gives the diastereomerically pure target compounds.

Example 11

Yield: 39 mg (37% of theory, 86% ee)

HPLC (method 6): R=11.97 min

LC/MS (method 7): $R_t$=2.96 min

MS (ESIneg): m/z=549 (M−H+ HCOOH)$^-$

1H-NMR (CDCl$_3$, 300 MHz): δ=0.75 (d, 3H), 1.18 (d, 3H), 1.42 (s, 3H), 1.48 (s, 3H), 1.82-2.04 (m, 3H), 2.97-3.10 (m, 1H), 4.53 (dd, 1H), 5.62 (d, 1H), 6.88 (s, 1H), 7.02-7.18 (m, 5H), 7.19-7.33 (m, 3H).

Example 12

Yield: 32 mg (32% of theory, 84% ee)

HPLC (method 6): $R_t$=14.05 min

LC/MS (method 7): $R_t$=3.02 min

MS (ESIneg): m/z=549 (M−H+HCOOH)$^-$ $^1$H-NMR (CDCl$_3$, 300 MHz): δ=0.65 (d, 3H), 1.18 (d, 3H), 1.44 (s, 3H), 1.48 (s, 3H), 1.99 (d, 2H), 2.07 (d, 1H), 2.97-3.12 (m, 1H), 4.55 (dd, 1H), 5.60 (d, 1H), 6.88 (s, 1H), 7.03-7.38 (m, 8H).

Example 13

(4S)-5-(4-Fluorophenyl)-7-isopropyl-2,2-dimethyl-6-[4-(trifluoromethoxy)benzyl]chroman-4-ol

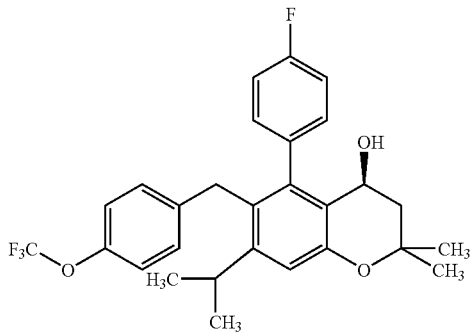

230 μl (1.29 mmol) of borane/N,N-diethylaniline complex are added slowly to a solution of 7.23 mg (50 μmol) of (1R,2S)-1-aminoindan-2-ol in 8 ml of tetrahydrofuran, and the mixture is stirred for 30 min. A solution of 163 mg (320 μmol) of rac-5-(4-fluorophenyl)-6-{fluoro[4-(trifluoromethoxy)phenyl]methyl}-7-isopropyl-2,2-dimethyl-2,3-dihydro-4H-chromen-4-one (Example 25A) in 8 ml of tetrahydrofuran is then slowly added dropwise. The mixture is stirred at room temperature overnight, methanol is then added and the solvent is removed under reduced pressure. The residue is taken up in ethyl acetate and washed in each case twice with 1 M hydrochloric acid and saturated sodium bicarbonate solution and once with saturated sodium chloride solution. The organic phase is dried over sodium sulfate and concentrated under reduced pressure. Purification of the residue by preparative HPLC (method 1) gives the target product.

Yield: 35 mg (22% of theory, 80% ee)
HPLC (method 4): $R_t$=3.44 min
LC/MS (method 9): $R_t$=3.42 min
MS (ESIpos): m/z=471 (M+H–H$_2$O)$^+$
$^1$H-NMR (CDCl$_3$, 300 MHz): δ=1.12 (d, 3H), 1.17 (d, 3H), 1.42 (s, 3H), 1.47 (s, 3H), 1.98 (d, 2H), 2.85-3.02 (m, 1H), 3.67 (d, 1H), 3.73 (d, 1H), 4.54 (dd, 1H), 6.80 (d, 2H), 6.88 (s, 1H), 6.91-7.17 (m, 6H).

Example 14

(4-tert-Butylphenyl)[(4S)-5-(4-fluorophenyl)-4-hydroxy-7-isopropyl-2,2-dimethyl-3,4-dihydro-2H-chromen-6-yl]methanone

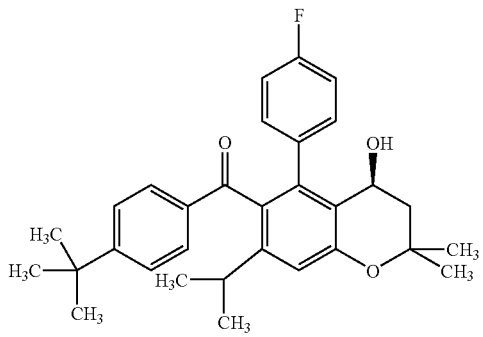

78 μl (540 μmol) of borane/N,N-diethylaniline complex are added slowly to a solution of 2.46 mg (20 μmol) of (1R,2S)-1-aminoindan-2-ol in 2 ml of tetrahydrofuran. The mixture is then cooled to 0° C., and a solution of 52 mg (110 μmol) of 6-(4-tert-butylbenzoyl)-5-(4-fluorophenyl)-7-isopropyl-2,2-dimethyl-2,3-dihydro-4H-chromen-4-one (Example 29A) in 3 ml of tetrahydrofuran are slowly added dropwise. The mixture is then allowed to thaw slowly and stirred at room temperature overnight. Methanol is then added, and the solvent is removed under reduced pressure. The residue is taken up in ethyl acetate and washed in each case twice with 1 M hydrochloric acid and saturated sodium bicarbonate solution and once with saturated sodium chloride solution. The organic phase is dried over sodium sulfate and then concentrated under reduced pressure. Purification of the residue by preparative HPLC (method 1) and subsequent chiral HPLC (method 2) gives the target compound.

Yield: 22 mg (42% of theory, 99.5% ee)
HPLC (method 5): $R_t$=5.71 min
LC/MS (method 7): $R_t$=3.22 min
MS (ESIpos): m/z=473 (M+H)$^+$
$^1$H-NMR (CDCl$_3$, 300 MHz): δ=1.03-1.38 (m, 6H), 1.29 (s, 9H), 1.46 (s, 3H), 1.49 (s, 3H), 2.02 (d, 2H), 2.62-2.83 (m, 1H), 4.72 (br. s, 1H), 6.53-7.24 (m, 7H), 7.37-7.59 (m, 2H).

In addition, in a second fraction, the enantiomer of the target product, (4-tert-butylphenyl)[(4R)-5-(4-fluorophenyl)-4-hydroxy-7-isopropyl-2,2-dimethyl-3,4-dihydro-2H-chromen-6-yl]methanone, is obtained:

Yield: 3 mg (5% of theory, 65% ee)
HPLC (method 5): $R_t$=8.26 min.

Example 15 and Example 16

(4S)-6-[(S)-(4-tert-Butylphenyl)(hydroxy)methyl]-5-(4-fluorophenyl)-7-isopropyl-2,2-dimethyl-chroman-4-ol (Example 15)

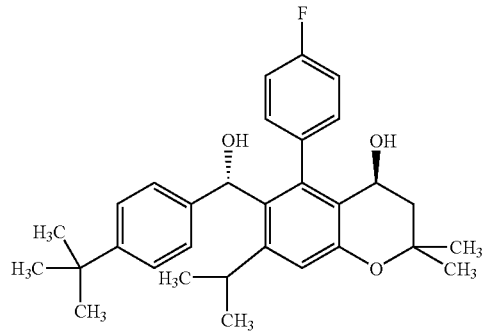

and (4S)-6-[(R)-(4-tert-butylphenyl)(hydroxy)methyl]-5-(4-fluorophenyl)-7-isopropyl-2,2-dimethyl-chroman-4-ol (Example 16)

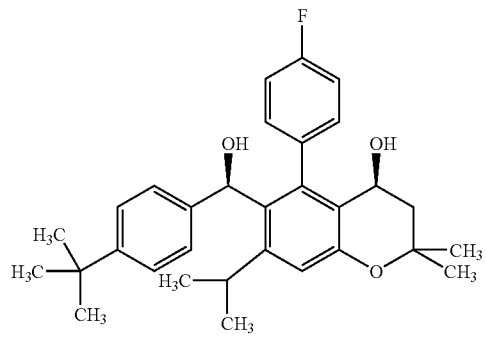

220 μl (1.26 mmol) of borane/N,N-diethylaniline complex are added very slowly to a solution of 7.07 mg (50 μmol) of (1R,2S)-1-aminoindan-2-ol in 7 ml of tetrahydrofuran, and the mixture is stirred at room temperature for 30 min. A solution of 150 mg (320 μmol) of rac-6-[(4-tert-butylphenyl)(hydroxy)methyl]-5-(4-fluorophenyl)-7-isopropyl-2,2-dimethyl-2,3-dihydro-4H-chromen-4-one (Example 27A) in 7 ml of tetrahydrofuran is then added very slowly dropwise over a period of 30 min. After a further 6 h of stirring, methanol is added and the solvent is removed under reduced pressure. The residue is taken up in ethyl acetate and washed in each case twice with 1 M hydrochloric acid and saturated sodium bicarbonate solution and once with saturated sodium chloride solution. The organic phase is dried over sodium sulfate and then concentrated under reduced pressure. Purification of the residue by column chromatography on silica gel (mobile phase: gradient cyclohexane→cyclohexane/ethyl acetate 10:1→5:1) gives the diastereomerically pure target products.

Example 15

Yield: 45 mg (30% of theory, 93% ee)
HPLC (method 6): $R_t$=13.02 min
LC/MS (method 9): $R_t$=3.29 min
MS (ESIneg): m/z=521 (M−H+HCOOH)⁻
$^1$H-NMR (CDCl$_3$, 300 MHz): δ=0.72 (d, 3H), 1.17 (d, 3H), 1.29 (s, 9H), 1.42 (s, 3H), 1.49 (s, 3H), 1.91-2.02 (m, 3H), 3.02-3.18 (m, 1H), 4.55 (dd, 1H), 5.63 (d, 1H), 6.98 (s, 1H), 7.00-7.22 (m, 5H), 7.22-7.37 (m, 3H).

Example 16

Yield: 49 mg (32% of theory, 96% ee)
HPLC (method 6): $R_t$=9.87 min
LC/MS (method 9): $R_t$=3.35 min
MS (ESIneg): m/z=521 (M−H+HCOOH)⁻
$^1$H-NMR (CDCl$_3$, 300 MHz): δ=0.63 (d, 3H), 1.18 (d, 3H), 1.27 (s, 9H), 1.43 (s, 3H), 1.47 (s, 3H), 1.93-2.08 (m, 3H), 3.02-3.18 (m, 1H), 4.58 (dd, 1H), 5.62 (d, 1H), 6.88 (s, 1H), 7.01-7.15 (m, 6H), 7.18-7.39 (m, 2H).

Example 17

(4S)-6-(4-tert-Butylbenzyl)-5-(4-fluorophenyl)-7-isopropyl-2,2-dimethylchroman-4-ol

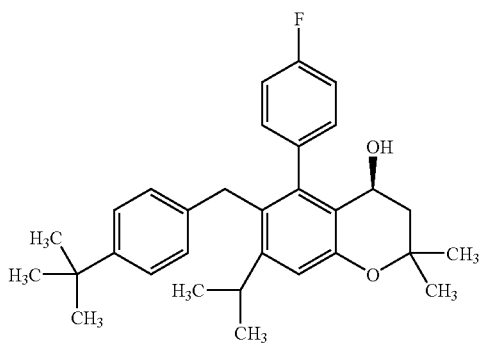

150 μl (840 μmol) of borane/N,N-diethylaniline complex are added slowly to a solution of 4.70 mg (30 μmol) of (1R,2S)-1-aminoindan-2-ol in 5 ml of tetrahydrofuran, and the mixture is stirred for 30 min. A solution of 100 mg (210 μmol) of rac-6-[(4-tert-butylphenyl)(fluoro)methyl]-5-(4-fluorophenyl)-7-isopropyl-2,2-dimethyl-2,3-dihydro-4H-chromen-4-one (Example 28A) in 5 ml of tetrahydrofuran is then slowly added dropwise. After 3 h of stirring at room temperature, methanol is added and the solvent is reduced under reduced pressure. The residue is taken up in ethyl acetate and washed in each case twice with 1 M hydrochloric acid and saturated sodium bicarbonate solution and once with saturated sodium chloride solution. The organic phase is dried over sodium sulfate and then concentrated under reduced pressure. Purification of the residue by column chromatography on silica gel (mobile phase: gradient cyclohexane→cyclohexane/ethyl acetate 10:1→5:1) gives the target product.

Yield: 37 mg (38% of theory, 90% ee)
HPLC (method 5): $R_t$=4.76 min
LC/MS (method 9): $R_t$=3.54 min
MS (ESIpos): m/z=443 (M+H−H$_2$O)⁺
MS (DCI): m/z=478 (M+NH$_4$)⁺
$^1$H-NMR (CDCl$_3$, 300 MHz): δ=1.10 (d, 3H), 1.13 (d, 3H), 1.27 (s, 9H), 1.42 (s, 3H), 1.48 (s, 3H), 1.97 (d, 2H), 2.93-3.08 (m, 1H), 3.61 (d, 1H), 3.70 (d, 1H), 4.57 (dd, 1H), 6.72 (d, 2H), 6.88 (s, 1H), 6.92-7.03 (m, 3H), 7.04-7.12 (m, 1H), 7.16 (d, 2H).

Example 18

[(4S)-4-Hydroxy-7-isopropyl-2,2-dimethyl-5-phenyl-3,4-dihydro-2H-chromen-6-yl][4-(trifluoromethoxy)phenyl]methanone

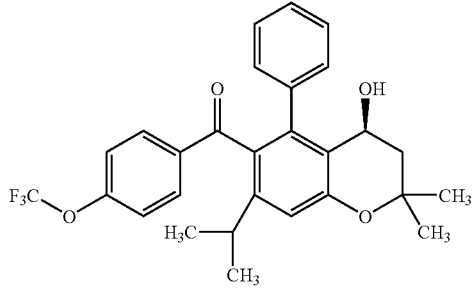

72 μl (410 μmol) of borane/N,N-diethylaniline complex are added slowly to a solution of 2.3 mg (20 μmol) of (1R,2S)-1-aminoindan-2-ol in 1.5 ml of tetrahydrofuran, and the mixture is stirred for 30 min. The mixture is then cooled to 0° C., and a solution of 49 mg (100 μmol) of 7-isopropyl-2,2-dimethyl-5-phenyl-6-[4-(trifluoromethoxy)benzoyl]-2,3-dihydro-4H-chromen-4-one (Example 32A) in 3.5 ml of tetrahydrofuran is slowly added dropwise. The mixture is allowed to thaw slowly and stirred at room temperature overnight. Methanol is then added, and the solvent is removed under reduced pressure. The residue is taken up in ethyl acetate and washed in each case twice with 1 M hydrochloric acid and saturated sodium bicarbonate solution and once with saturated sodium chloride solution. The organic phase is dried over sodium sulfate and then concentrated under reduced pressure. Purification of the residue by preparative HPLC (method 1) gives the target product.

Yield: 41 mg (83% of theory, 88% ee)
HPLC (method 6): $R_t$=4.08 min
LC/MS (method 8): $R_t$=3.16 min
MS (ESIpos): m/z=485 (M+H)⁺

¹H-NMR (CDCl₃, 400 MHz): δ=1.15 (d, 3H), 1.23 (d, 3H), 1.45 (s, 3H), 1.49 (s, 3H), 1.94-2.09 (m, 2H), 2.64-2.81 (m, 1H), 4.74 (s, 1H), 6.92 (s, 1H), 6.93-7.33 (m, 7H), 7.48-7.66 (m, 2H).

Example 19

(5-Cyclohex-1-en-1-yl-4-hydroxy-7-isopropyl-2,2-dimethyl-3,4-dihydro-2H-chromen-6-yl)[4-(tri-fluoromethyl)phenyl]methanone

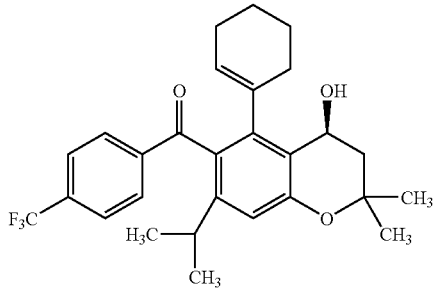

80 µl (450 µmol) of borane/N,N-diethylaniline complex are added slowly to a solution of 2.51 mg (17 µmol) of (1R,2S)-1-aminoindan-2-ol in 2.6 ml of tetrahydrofuran. The mixture is then cooled to 0° C., and a solution of 53 mg (112 µmol) of 5-cyclohex-1-en-1-yl-7-isopropyl-2,2-dimethyl-6-[4-(trifluoromethyl)benzoyl]-2,3-dihydro-4H-chromen-4-one (Example 37A) in 2.6 ml of tetrahydrofuran is slowly added dropwise. The mixture is allowed to thaw slowly and stirred at room temperature overnight. Methanol is then added, and the solvent is removed under reduced pressure. The residue is taken up in ethyl acetate and washed in each case twice with 1 M hydrochloric acid and saturated sodium bicarbonate solution and once with saturated sodium chloride solution. The organic phase is dried over sodium sulfate and then concentrated under reduced pressure. Purification of the residue by column chromatography on silica gel (mobile phase: cyclohexane→cyclohexane/ethyl acetate 20:1) and subsequent chiral HPLC (method 2) gives the target compound.

Yield: 15 mg (28% of theory, >99% ee)
HPLC (method 2): R_t=3.62 min
LC/MS (method 7): R_t=3.15 min
MS (ESIpos): m/z=473 (M+H)⁺.

Example 20 and Example 21

(4S)-5-Cyclohex-1-en-1-yl-6-{(S)-hydroxy[4-(trifluoromethyl)phenyl]methyl}-7-isopropyl-2,2-dimethylchroman-4-ol (Example 20)

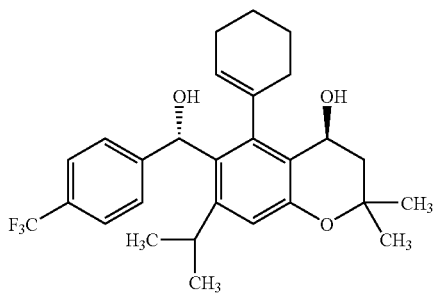

and (4S)-5-cyclohex-1-en-1-yl-6-{(R)-hydroxy[4-(trifluoromethyl)phenyl]methyl}-7-isopropyl-2,2-dimethylchroman-4-ol (Example 21)

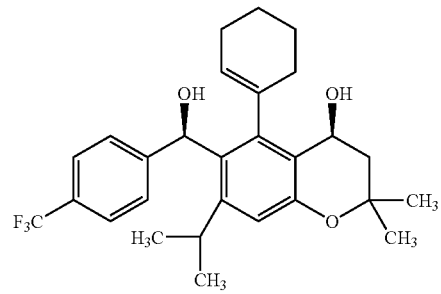

230 µl (1.27 mmol) of borane/N,N-diethylaniline complex are added very slowly to a solution of 7.10 mg (50 µmol) of (1R,2S)-1-aminoindan-2-ol in 7.5 ml of tetrahydrofuran, and the mixture is stirred at room temperature for 30 min. A solution of 150 mg (320 µmol) of 5-cyclohex-1-en-1-yl-6-{hydroxy[4-(trifluoromethyl)phenyl]methyl}-7-isopropyl-2,2-dimethyl-2,3-dihydro-4H-chromen-4-one (Example 35A) in 7.5 ml of tetrahydrofuran are then added very slowly dropwise over a period of 30 min. The mixture is stirred overnight, methanol is then added and the solvent is removed under reduced pressure. The residue is taken up in ethyl acetate and washed in each case twice with 1 M hydrochloric acid and saturated sodium bicarbonate solution and once with saturated sodium chloride solution. The organic phase is dried over sodium sulfate and then concentrated under reduced pressure. Purification of the residue by column chromatography on silica gel (mobile phase: gradient cyclohexane→cyclohexane/ethyl acetate 20:1→10:1→1:1) and subsequent preparative HPLC (method 1) gives the diastereomerically pure target compounds, which for their part are present as a mixture of two rotamers.

Example 20

Yield: 53 mg (36% of theory)
HPLC (method 6): R_t=6.31 min
LC/MS (method 9): R_t=3.24 min
MS (ESIneg): m/z=519 (M–H+HCOOH)⁻
¹H-NMR (CDCl₃, 400 MHz): δ=0.57 [0.62] (d, 3H), 1.08 [1.12] (d, 3H), 1.40 [1.42] (s, 3H), 1.50 [1.53] (s, 3H), 1.57-1.91 (m, 6H), 1.94-2.43 (m, 6H), 2.59 (s, 1H), 2.77-2.88 [2.89-3.03] (m, 1H), 4.68-4.77 [5.02-5.11] (m, 1H), 5.63-5.72 [5.78-5.87] (m, 1H), 6.03-6.11 [6.11-6.18] (m, 1H), 6.74 (s, 1H), 7.38-7.49 (m, 2H), 7.58 (d, 2H).

Example 21

Yield: 47 mg (26% of theory)
HPLC (method 6): R_t=9.92 min
LC/MS (method 9): R_t=3.28 min
MS (ESIneg): m/z=519 (M–H+HCOOH)⁻
¹H-NMR (CDCl₃, 400 MHz): δ=0.47 [0.59] (d, 3H), 1.12 [1.10] (d, 3H), 1.42 [1.45] (s, 3H), 1.47 [1.50] (s, 3H), 1.57-1.97 (m, 6H), 1.99-2.59 (m, 7H), 2.98 [2.86] (m, 1H), 5.08

[4.71] (m, 1H), 5.68 [5.88] (m, 1H), 6.09 [6.12] (m, 1H), 6.71 [6.76] (s, 1H), 7.34-7.43 (m, 2H), 7.48-7.58 (d, 2H).

Example 22 and Example 23

(4S)-5-Cyclopent-1-en-1-yl-6-{(S)-hydroxy[4-(trifluoromethyl)phenyl]methyl}-7-isopropyl-2,2-dimethylchroman-4-ol (Example 22)

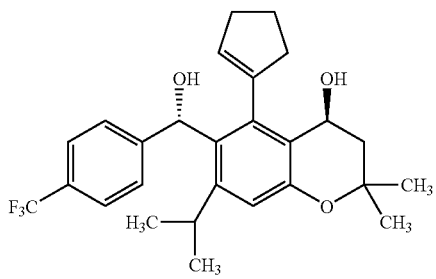

and (4S)-5-cyclopent-1-en-1-yl-6-{(R)-hydroxy[4-(trifluoromethyl)phenyl]methyl}-7-isopropyl-2,2-dimethylchroman-4-ol (Example 23)

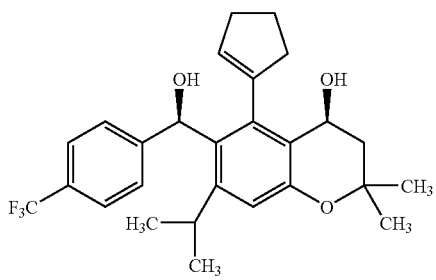

The title compounds are obtained as by-products in the preparation of Example 38A.

Example 22

Yield: 2.2 mg (2% of theory)
HPLC (method 6): $R_t$=10.67 min LC/MS (method 7): $R_t$=2.97 min
MS (ESIneg): m/z=505 (M−H+HCOOH)⁻
¹H-NMR (CDCl₃, 400 MHz): δ=0.61 (d, 3H), 1.14 (d, 3H), 1.42 (s, 3H), 1.51 (s, 3H), 1.84-2.16 (m, 6H), 2.35-3.05 (m, 5H), 4.65-4.72 (m, 1H), 5.82-5.90 (m, 1H), 5.97-6.04 (m, 1H), 6.76 (s, 1H), 7.42 (d, 2H), 7.56 (d, 2H).

Example 23

Yield: 7.3 mg (7% of theory)
HPLC (method 6): $R_t$=8.75 min
LC/MS (method 7): $R_t$=3.05 min
MS (ESIneg): m/z=505 (M−H+HCOOH)⁻
1H-NMR (CDCl₃, 400 MHz): δ=0.59 (d, 3H), 1.12 (d, 3H), 1.45 (s, 3H), 1.49 (s, 3H), 1.97-2.25 (m, 5H), 2.34-3.06 (m, 6H), 4.64-4.72 (m, 1H), 5.82-5.93 (m, 1H), 5.99-6.07 (m, 1H), 6.77 (s, 1H), 7.39 (d, 2H), 7.54 (d, 2H).

Example 24 and Example 25

(4S)-5-Cyclopent-1-yl-6-{(S)-hydroxy[4-(trifluoromethyl)phenyl]methyl}-7-isopropyl-2,2-dimethylchroman-4-ol (Example 24)

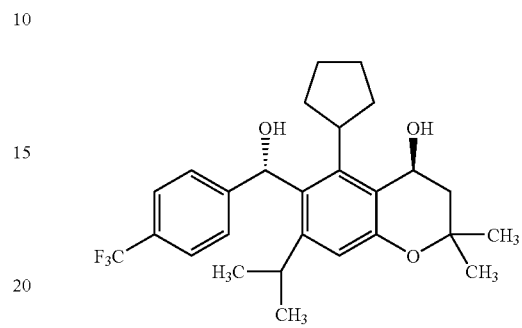

and (4S)-5-cyclopent-1-yl-6-{(R)-hydroxy[4-(trifluoromethyl)phenyl]methyl}-7-isopropyl-2,2-dimethylchroman-4-ol (Example 25)

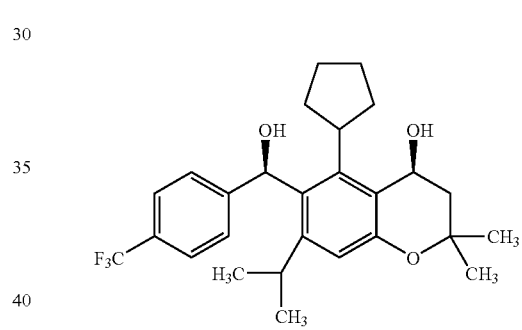

23 μl (130 μmol) of borane/N,N-diethylaniline complex are added to a solution of 0.1 mg (6.7 μmol) of (1R,2S)-1-aminoindan-2-ol in 1.0 ml of tetrahydrofuran, and the mixture is stirred for 30 min. A solution of 15 mg (33 μmol) of 5-cyclopent-1-yl-6-{hydroxy[4-(trifluormethyl)phenyl]methyl}-7-isopropyl-2,2-dimethyl-2,3-dihydro-4H-chromen-4-one (Example 38A) in 1.0 ml of tetrahydrofuran is then added dropwise, and the mixture is stirred for 2 h. Methanol is then added, and the mixture is concentrated under reduced pressure. The residue is taken up in ethyl acetate and washed in each case twice with 1 M hydrochloric acid and saturated sodium bicarbonate solution and once with saturated sodium chloride solution. The organic phase is dried over sodium sulfate and then concentrated under reduced pressure. Purification of the crude product by preparative HPLC (method 1) gives the diastereomerically pure target compounds.

Example 24

Yield: 5.4 mg (36% of theory)
HPLC (method 6): $R_t$=10.47 min
LC/MS (method 7): $R_t$=2.91 min
MS (ESIneg): m/z=507 (M−H+HCOOH)⁻
1H-NMR (CDCl₃, 400 MHz): δ=0.58 (br. d, 3H), 1.09 (d, 3H), 1.42 (s, 3H), 1.50 (s, 3H), 1.52-1.96 (m, 8H), 2.02-2.21

(m, 4H), 2.90 (m, 1H), 3.81 (m, 1H), 5.04 (m, 1H), 6.19 (m, 1H), 6.72 (s, 1H), 7.42 (d, 2H), 7.56 (d, 2H).

Example 25

Yield: 5.9 mg (36% of theory)

HPLC (method 6): $R_t$=18.45 min

LC/MS (method 7): $R_t$=3.18 min

MS (ESIneg): m/z=507 (M−H+HCOOH)⁻

$^1$H-NMR (CDCl$_3$, 400 MHz): δ=0.59 (br. m, 3H), 1.09 (d, 3H), 1.44 (s, 3H), 1.49 (s, 3H), 1.52-2.31 (m, 12H), 2.79-2.97 (m, 1H), 3.72-3.92 (m, 1H), 4.97-5.06 (m, 1H), 6.19 (m, 1H), 6.73 (s, 1H), 7.41 (d, 2H), 7.55 (d, 2H).

Example 26

(4S)-5-Cyclopentyl-7-isopropyl-2,2-dimethyl-6-[4-(trifluoromethyl)benzyl]chroman-4-ol

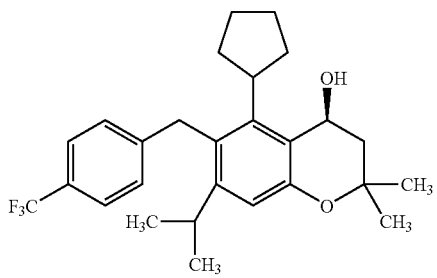

40 μl (210 μmol) of borane/N,N-diethylaniline complex are added slowly to a solution of 1.2 mg (10 μmol) of (1R, 2S)-1-aminoindan-2-ol in 1.5 ml of tetrahydrofuran, and the mixture is stirred for 30 min. A solution of 23 mg (50 μmol) of 5-cyclopentyl-7-isopropyl-2,2-dimethyl-6-[4-(trifluoromethyl)benzyl]-2,3-dihydro-4H-chromen-4-one (Example 39A) in 1.5 ml of tetrahydrofuran is then added very slowly dropwise, and the mixture is stirred for 2 h. Methanol is then added, and the mixture is concentrated under reduced pressure. The residue is taken up in ethyl acetate and washed in each case twice with 1 M hydrochloric acid and saturated sodium bicarbonate solution and once with saturated sodium chloride solution. The organic phase is dried over sodium sulfate and then concentrated under reduced pressure. Purification of the residue by preparative HPLC (method 1) gives the target product.

Yield: 17 mg (71% of theory, 70% ee)

HPLC (method 5): $R_t$=6.87 min

LC/MS (method 8): $R_t$=3.39 min

MS (ESIpos): m/z=429 (M+H−H$_2$O)⁺

$^1$H-NMR (CDCl$_3$, 400 MHz): δ=1.0 (d, 6H), 1.42 (s, 3H), 1.51 (s, 3H), 1.52-2.01 (m, 8H), 2.08 (dd, 1H), 2.19 (dd, 1H), 2.63-2.78 (m, 1H), 3.61-3.78 (m, 1H), 4.13 (s, 2H), 5.02 (s, 1H), 4.98-5.08 (m, 1H), 6.72 (s, 1H), 7.09 (d, 2H), 7.48 (d, 2H).

Example 27

[(4S)-5-(4-Fluorophenyl)-4-hydroxy-7-isopropyl-3,4-dihydrospiro[chromen-2,1'-cyclobutan]-6-yl]-[4-(trifluoromethyl)phenyl]methanone

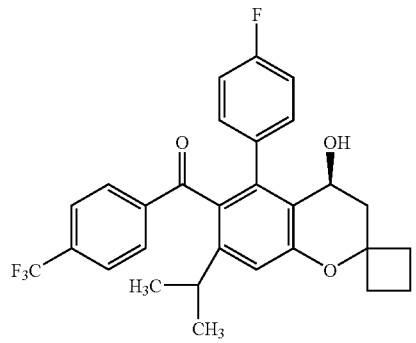

Under argon, 2.7 mg (0.02 mmol) of (1R,2S)-1-aminoindan-2-ol are dissolved in 2 ml of abs. tetrahydrofuran, 130 μl (0.72 mmol) of borane/N,N-diethylaniline complex are added and the mixture is stirred at room temperature for 30 min. 90 mg (0.18 mmol) of 5-(4-fluorophenyl)-7-isopropyl-6-[4-(trifluoromethyl)benzoyl]spiro[chromen-2,1'-cyclobutan]-4(3H)-one (Example 54A), dissolved in 2.5 ml of abs. tetrahydrofuran, are then added at room temperature over a period of 10 min, and the mixture is then stirred at room temperature for 5 h. 2 ml of methanol are added and the mixture is stirred for 15 min and then concentrated to dryness. The residue is taken up in ethyl acetate and washed twice with 1 N hydrochloric acid, twice with saturated sodium bicarbonate solution and twice with saturated sodium chloride solution. The organic phase is dried over sodium sulfate, filtered and concentrated. The crude product is purified by preparative HPLC. This gives 49 mg (54% of theory) of the title compound having an ee of 70%.

$R_t$=5.54 min [Chiralpak IA, 250×4.6 mm; mobile phase: isopropanol/isohexane 3:97; flow rate: 2 ml/min; detection: 260 nm].

$^1$H-NMR (400 MHz, CDCl$_3$): δ=7.62 (d, 2H), 7.52 (d, 2H), 7.22-6.70 (m, 5H), 4.62 (br. s, 1H), 2.75-2.59 (m, 3H), 2.48 (q, 1H), 2.33-2.23 (m, 2H), 2.22-2.15 (m, 1H), 2.07-1.92 (m, 2H), 1.81-1.69 (m, 1H), 1.19 (dd, 6H).

MS (DCI): m/z=498 (M+H)⁺, 516 (M+NH$_4$)⁺.

Example 28 and Example 29

(4S)-5-(4-Fluorophenyl)-6-{(S)-hydroxy[4-(trifluoromethyl)phenyl]methyl}-7-isopropyl-3,4-dihydrospiro[chromen-2,1'-cyclobutan]-4-ol
(Example 28)

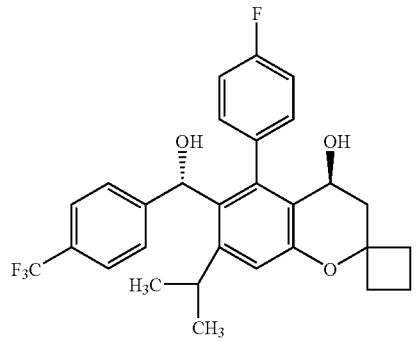

and (4S)-5-(4-fluorophenyl)-6-{(R)-hydroxy[4-(trifluoromethyl)phenyl]methyl}-7-isopropyl-3,4-dihydrospiro[chromen-2,1'-cyclobutan]-4-ol (Example 29)

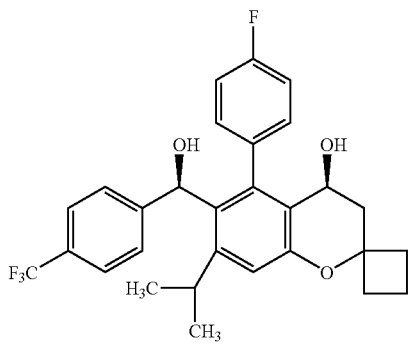

Under argon, 1.6 mg (0.011 mmol) of (1R,2S)-1-aminoindan-2-ol are dissolved in 1 ml of abs. tetrahydrofuran, 77 µl (0.43 mmol) of borane/N,N-diethylaniline complex are added and the mixture is stirred at room temperature for 30 min. After this time, 60 mg (0.108 mmol) of 5-(4-fluorophenyl)-6-{hydroxy[4-(trifluoromethyl)phenyl]methyl}-7-isopropylspiro[chromen-2,1'-cyclobutan]-4(3H)-one (Example 52A), dissolved in 2 ml of abs. tetrahydrofuran, are added at room temperature over a period of 10 min, and the mixture is then stirred at room temperature for 18 h. 2 ml of methanol are added and the mixture is stirred for 15 min and then concentrated to dryness. The residue is taken up in ethyl acetate and washed twice with 1 N hydrochloric acid, twice with saturated sodium bicarbonate solution and twice with saturated sodium chloride solution. The organic phase is dried over sodium sulfate, filtered and concentrated. The crude product obtained is purified by preparative thick-layer chromatography (mobile phase: cyclohexane/ethyl acetate 4:1), resulting in the separation of the diastereomers.

Example 28

Yield: 22 mg (41% of theory)

$^1$H-NMR (300 MHz, CDCl$_3$): δ=7.51 (d, 2H), 7.38-7.27 (m, 3H), 7.19-7.02 (m, 3H), 6.91 (s, 1H), 5.62 (br. s, 1H), 4.54-4.47 (m, 1H), 2.99 (heptet, 1H), 2.72-2.60 (m, 1H), 2.50-2.37 (m, 1H), 2.35-1.86 (m, 6H), 1.79-1.68 (m, 1H), 1.48 (br. s, 1H), 1.19 (d, 3H), 0.70 (d, 3H).

MS (DCI): m/z=501 (M+H)$^+$, 518 (M+NH$_4$)$^+$.

Example 29

Yield: 22 mg (41% of theory)

$^1$H-NMR (400 MHz, CDCl$_3$): δ=7.50 (d, 2H), 7.35-7.27 (m, 3H), 7.21-7.05 (m, 3H), 6.91 (s, 1H), 5.62 (br. s, 1H), 4.50 (br. s, 1H), 2.99 (heptet, 1H), 2.72-2.62 (m, 1H), 2.49-2.38 (m, 1H), 2.35-1.88 (m, 6H), 1.80-1.68 (m, 1H), 1.40 (d, 1H), 1.21 (d, 3H), 0.66 (d, 3H).

MS (DCI): m/z=501 (M+H)$^+$, 518 (M+NH$_4$)$^+$.

Example 30 and Example 31

(4S)-5-(4-Fluorophenyl)-6-{(S)-fluoro[4-(trifluoromethyl)phenyl]methyl}-7-isopropyl-3,4-dihydrospiro[chromen-2,1'-cyclobutan]-4-ol (Example 30)

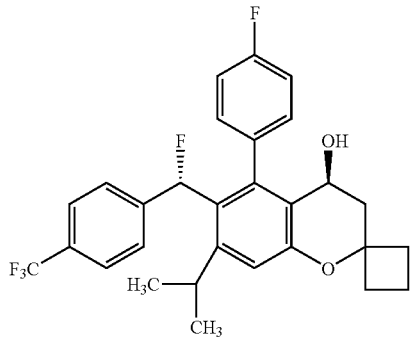

and (4S)-5-(4-fluorophenyl)-6-{(R)-fluoro[4-(trifluoromethyl)phenyl]methyl}-7-isopropyl-3,4-dihydro-spiro[chromen-2,1'-cyclobutan]-4-ol (Example 31)

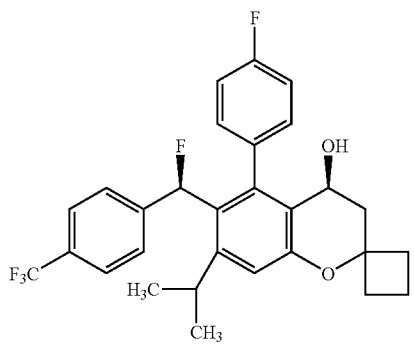

Under argon, 3.1 mg (0.02 mmol) of (1R,2S)-1-aminoindan-2-ol are dissolved in 3 ml of abs. tetrahydrofuran, 0.15 ml (0.84 mmol) of borane/N,N-diethylaniline complex are added and the mixture is stirred at room temperature for 30 min. After this time, 105 mg (0.21 mmol) of 5-(4-fluorophenyl)-6-{fluoro[4-(trifluoromethyl)phenyl]methyl}-7-isopropylspiro[chromen-2,1'-cyclobutan]-4(3H)-one (Example 53A), dissolved in 4 ml of abs. tetrahydrofuran, are added at room temperature over a period of 10 min, and the mixture is then stirred at room temperature for 6 h. 3 ml of methanol are added and the mixture is stirred for 15 min and then concentrated to dryness. The residue is taken up in ethyl acetate and washed twice with 1 N hydrochloric acid, twice with saturated sodium bicarbonate solution and twice with saturated sodium chloride solution. The organic phase is dried over sodium sulfate, filtered and concentrated. The crude product is purified on a silica gel column (mobile phase: cyclohexane→cyclohexane/ethyl acetate 10:1). This gives 110 mg of a mixture of the two target compounds. Subsequent chromatographic separation on a chiral phase [column: chiral silica gel selector based on poly(N-methacryloyl-L-leucine-tert-butylamide), 670 mm×40 mm; mobile phase: MTBE/ isohexane 15:85; flow rate: 80 ml/min; 24° C.; detection: 280 nm] gives 36 mg (36% of theory, 98% ee) of Example 30 and 45 mg (43% of theory, >99% ee) of Example 31.

Example 30

R$_t$=3.81 min [column: chiral silica gel selector based on poly(N-methacryloyl-L-leucine-tert-butylamide), 250 mm×4.6 mm; mobile phase: MTBE/isohexane 15:85; flow rate: 2 ml/min; detection: 270 nm].
$^1$H-NMR (400 MHz, CDCl$_3$): δ=7.54 (d, 2H), 7.27-7.14 (m, 4H), 7.12-6.99 (m, 2H), 6.96 (s, 1H), 6.28 (d, 1H), 4.57-4.50 (m, 1H), 2.94-2.83 (m, 1H), 2.71-2.62 (m, 1H), 2.50-2.39 (m, 1H), 2.35-2.22 (m, 2H), 2.21-2.10 (m, 1H), 2.00-1.89 (m, 2H), 1.80-1.68 (m, 1H), 1.42 (d, 1H), 1.18 (d, 3H), 0.81 (d, 3H).
MS (DCI): m/z=502 (M)$^+$, 520 (M+NH$_4$)$^+$.

Example 31

R$_t$=3.09 min [column: chiral silica gel selector based on poly(N-methacryloyl-L-leucine-tert-butylamide), 250 mm×4.6 mm; mobile phase: MTBE/isohexane 15:85; flow rate: 2 ml/min; detection: 270 nm].
$^1$H-NMR (400 MHz, CDCl$_3$): δ=7.53 (d, 2H), 7.38-7.32 (m, 1H), 7.21 (d, 2H), 7.11-7.00 (m, 3H), 6.96 (s, 1H), 6.28 (d, 1H), 4.53-4.48 (m, 1H), 2.88 (heptet, 1H), 2.72-2.63 (m, 1H), 2.50-2.39 (m, 1H), 2.36-2.29 (m, 1H), 2.28-2.11 (m, 2H), 2.01-1.89 (m, 2H), 1.80-1.69 (m, 1H), 1.40 (d, 1H), 1.19 (d, 3H), 0.76 (d, 3H).
MS (DCI): m/z=502 (M)$^+$, 520 (M+NH$_4$)$^+$.

Example 32

(4S)-5-(4-Fluorophenyl)-7-isopropyl-6-[4-(trifluoromethyl)benzyl]-3,4-dihydrospiro[chromen-2,1'-cyclobutan]-4-ol

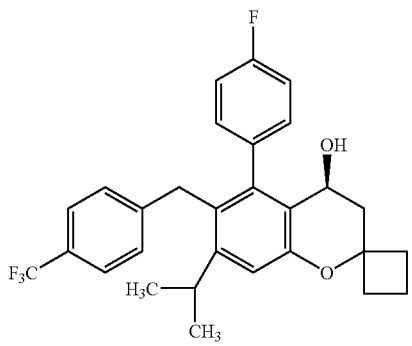

Under argon, 50 mg (0.10 mmol) of 5-(4-fluorophenyl)-6-{hydroxy[4-(trifluoromethyl)phenyl]-methyl}-7-isopropylspiro[chromen-2,1'-cyclobutan]-4(3H)-one (Example 52A) are dissolved in 1 ml of tetrahydrofuran, and 22 μl (0.16 mmol) of triethylamine are added. 10 μl (0.13 mmol) of thionyl chloride are then slowly added dropwise, and the mixture is stirred for 1.5 h. In the meantime, in a separate flask and under argon, 1.5 mg (0.01 mmol) of (1R,2S)-1-aminoindan-2-ol are dissolved in 2.7 ml of abs. tetrahydrofuran, 72 μl (0.40 mmol) of borane/N,N-diethylaniline complex are added and the mixture is stirred at room temperature for 30 min. This solution is then added dropwise to the first mixture, and the reaction mixture is stirred at room temperature overnight. In a further flask, under argon, another 1.5 mg (0.01 mmol) of (1R,2S)-1-aminoindan-2-ol are dissolved in 1 ml of abs. tetrahydrofuran, 54 μl (0.30 mmol) of borane/N,N-diethylaniline complex are added, the mixture is stirred at room temperature for 30 min and then again added dropwise to the reaction solution. The reaction mixture is then stirred at room temperature overnight again.

After this time, 0.5 ml (0.5 mmol) of lithium aluminum hydride solution (1 M in tetrahydrofuran) is then added dropwise at room temperature to the reaction mixture. After 2 and 4 h, in each case the same amounts of lithium aluminum hydride solution are added again. After a further hour, the mixture is diluted with tetrahydrofuran and poured into ice-water, and 5 ml of 6 N hydrochloric acid are added. The aqueous phase is extracted twice with ethyl acetate. The organic phases are washed once with 1 N hydrochloric acid, twice with saturated sodium bicarbonate solution and twice with saturated sodium chloride solution. The organic phase is dried over sodium sulfate, filtered and concentrated. The crude product is purified by preparative thick-layer chromatography (mobile phase: cyclohexane/ethyl acetate 5:1). Subsequent chromatographic separation of the enantiomers on a chiral phase [column: Chiralpak AD-H, 250×20 mm; mobile phase: isopropanol/isohexane 3:97; flow rate: 1.5 ml/min; 24° C.; detection: 260 μm] gives 8 mg (16% of theory) of the desired enantiomerically pure compound.

R$_t$=4.34 min [column: Chiralpak IA, 250×4.6 mm; mobile phase: isopropanol/isohexane 3:97; flow rate: 1.5 ml/min; detection: 260 nm].
$^1$H-NMR (400 MHz, CDCl$_3$): δ=7.40 (d, 2H), 7.11-7.06 (m, 1H), 7.02-6.88 (m, 6H), 4.54-4.48 (m, 1H), 3.81-3.69 (m, 2H), 2.89 (heptet, 1H), 2.70-2.61 (m, 1H), 2.49-2.38 (m, 1H), 2.32-2.10 (m, 3H), 2.00-1.89 (m, 2H), 1.80-1.66 (m, 1H), 1.41 (d, 1H), 1.17 (d, 3H), 1.12 (d, 3H).
MS (DCI): m/z=484 (M)$^+$, 502 (M+NH$_4$)$^+$.

Example 33

(4-tert-Butylphenyl)[(4S)-5-(4-fluorophenyl)-4-hydroxy-7-isopropyl-3,4-dihydrospiro[chromen-2,1'-cyclobutan]-6-yl]methanone Under argon, 2.1 mg (0.014 mmol) of (1R,2S)-1-aminoindan-2-ol are dissolved in 1.5 ml of abs. tetrahydrofuran, 99 μl (0.56 mmol) of borane/N,N-diethylaniline complex are added and the mixture is stirred at room temperature for 30 min. After this time, 81.5 mg (0.14 mmol) of 6-(4-tert-butylbenzoyl)-5-(4-fluorophenyl)-7-isopropylspiro[chromen-2,1'-cyclobutan]-4(3H)-one (Example 57A), dissolved in 2 ml of abs. tetrahydrofuran, are then added at room temperature over a period of 10 min, and the mixture is then stirred at room temperature for 4 h. 2 ml of methanol are added, and the mixture is stirred for 15 min and then concentrated to dryness.

The residue is taken up in ethyl acetate and washed twice with 1 N hydrochloric acid, twice with saturated sodium bicarbonate solution and twice with saturated sodium chloride solution. The organic phase is dried over sodium sulfate, filtered and concentrated. The crude product is purified by preparative HPLC. This gives 41 mg (60% of theory) of the title compound having an ee of 87%.

$R_t$=8.46 min [column: Chiralpak IA, 250×4.6 mm; mobile phase: isopropanol/isohexane 3:97; flow rate: 1.5 ml/min; detection: 230 nm].

$^1$H-NMR (400 MHz, CDCl$_3$): δ=7.48 (br. s, 2H), 7.28 (s, 2H), 7.24-6.55 (m, 5H), 4.65 (br. s, 1H), 2.80-2.56 (m, 2H), 2.46 (q, 1H), 2.33-2.12 (m, 3H), 2.07-1.90 (m, 2H), 1.80-1.69 (m, 1H), 1.30 (s, 9H), 1.25-1.09 (m, 6H).

MS (DCI): m/z=487 (M+H)$^+$, 504 (M+NH$_4$)$^+$.

Example 34 and Example 35

(4S)-6-[(S)-(4-tert-Butylphenyl)(hydroxy)methyl]-5-(4-fluorophenyl)-7-isopropyl-3,4-dihydro-spiro[chromen-2,1'-cyclobutan]-4-ol (Example 34)

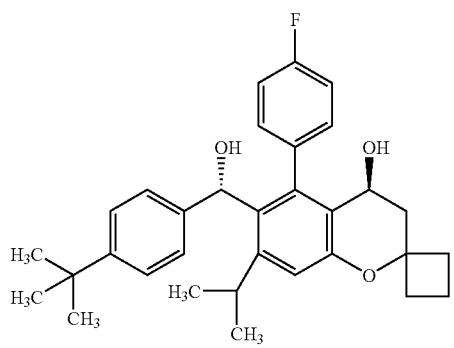

and (4S)-6-[(R)-(4-tert-butylphenyl)(hydroxy)methyl]-5-(4-fluorophenyl)-7-isopropyl-3,4-dihydro-spiro[chromen-2,1'-cyclobutan]-4-ol (Example 35)

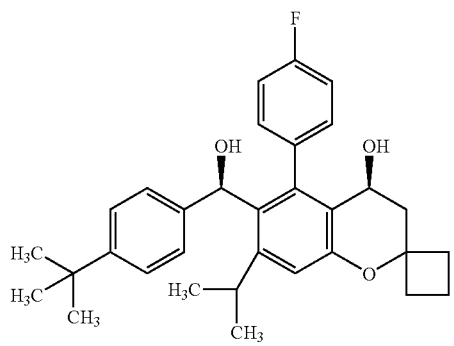

Under argon, 2.1 mg (0.014 mmol) of (1R,2S)-1-aminoindan-2-ol are dissolved in 3 ml of abs. tetrahydrofuran, 102 μl (0.575 mmol) of borane/N,N-diethylaniline complex are added and the mixture is stirred at room temperature for 30 min. After this time, 70 mg (0.144 mmol) of 6-[(4-tert-butylphenyl)(hydroxy)methyl]-5-(4-fluorophenyl)-7-isopropylspiro[chromen-2,1'-cyclobutan]-4(3H)-one (Example 55A), dissolved in 3.25 ml of abs. tetrahydrofuran, are added at room temperature over a period of 10 min, and the mixture is then stirred at room temperature for 18 h. 2 ml of methanol are added and the mixture is stirred for 15 min and then concentrated to dryness. The residue is taken up in ethyl acetate and washed twice with 1 N hydrochloric acid, twice with saturated sodium bicarbonate solution and twice with saturated sodium chloride solution. The organic phase is dried over sodium sulfate, filtered and concentrated. The crude product is purified by preparative thick-layer chromatography (mobile phase: cyclohexane/ethyl acetate 5:1). This gives 26 mg (37% of theory, 86% ee) of Example 34 and 29 mg (42% of theory, 89% ee) of Example 35. Subsequent chromatographic separation of 15 mg of Example 34 on a chiral phase [column: Chiralpak AD-H, 250×20 mm; mobile phase: isopropanol/isohexane 5:95; flow rate: 15 ml/min; 24° C.; detection: 260 nm] gives 10.6 mg of Example 34 having an ee of >99%.

Example 34

$R_t$=9.34 min [column: Chiralpak IA, 250×4.6 mm; mobile phase: isopropanol/isohexane 5:95; flow rate: 2 ml/min; detection: 260 nm].

$^1$H-NMR (300 MHz, CDCl$_3$): δ=7.36-7.27 (m, 3H), 7.20-7.00 (m, 5H), 6.91 (s, 1H), 5.62 (d, 1H), 4.53-4.47 (m, 1H), 3.11 (heptet, 1H), 2.73-2.60 (m, 1H), 2.49-2.09 (m, 4H), 2.02-1.87 (m, 3H), 1.82-1.68 (m, 1H), 1.45 (d, 1H), 1.30 (s, 9H), 1.18 (d, 3H), 0.71 (d, 3H).

MS (DCI): m/z=506 (M+NH$_4$)$^+$.

Example 35

$R_t$=10.98 min [column: Chiralpak IA, 250×4.6 mm; mobile phase: isopropanol/isohexane 5:95; flow rate: 2 ml/min; detection: 260 nm].

$^1$H-NMR (300 MHz, CDCl$_3$): δ=7.33-7.18 (m, 4H), 7.12-7.03 (m, 4H), 6.91 (s, 1H), 5.62 (d, 1H), 4.54-4.48 (m, 1H), 3.11 (heptet, 1H), 2.73-2.61 (m, 1H), 2.50-2.38 (m, 1H), 2.35-2.09 (m, 3H), 2.03-1.88 (m, 3H), 1.81-1.67 (m, 1H), 1.39 (d, 1H), 1.27 (s, 9H), 1.20 (d, 3H), 0.65 (d, 3H).

MS (DCI): m/z=506 (M+NH$_4$)$^+$.

Example 36

(4S)-6-(4-tert-Butylbenzyl)-5-(4-fluorophenyl)-7-isopropyl-3,4-dihydrospiro[chromen-2,1'-cyclo-butan]-4-ol

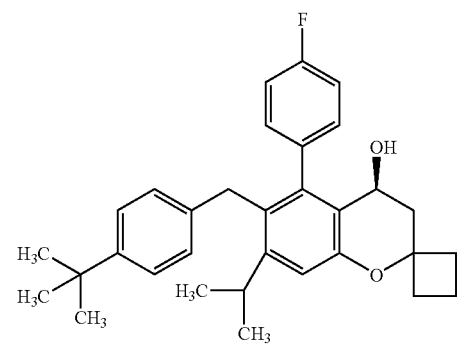

Under argon, 1.4 mg (0.009 mmol) of (1R,2S)-1-aminoindan-2-ol are dissolved in 2 ml of abs. tetrahydrofuran, 66 µl (0.37 mmol) of borane/,N-diethylaniline complex are added and the mixture is stirred at room temperature for 30 min. After this time, 45 mg (0.092 mmol) of 6-[(4-tert-butylphenyl)(fluoro)methyl]-5-(4-fluorophenyl)-7-isopropylspiro[chromen-2,1'-cyclobutan]-4(3H)-one (Example 55A), dissolved in 2 ml of abs. tetrahydrofuran, are added at room temperature over a period of 10 min, and the mixture is then stirred at room temperature for 15 h. 2 ml of methanol are added and the mixture is stirred for 15 min and then concentrated to dryness. The residue is taken up in ethyl acetate and washed twice with 1 N hydrochloric acid, twice with saturated sodium bicarbonate solution and twice with saturated sodium chloride solution. The organic phase is dried over sodium sulfate, filtered and concentrated. The crude product is purified by thick-layer chromatography (mobile phase: cyclohexane/ethyl acetate 10:1). This gives 33.5 mg (77% of theory, 80% ee) of the title compound. Chromatographic separation of 60 mg of Example 36 on a chiral phase [column: Chiralpak AD-H, 250×20 mm; mobile phase: isopropanol/isohexane 3:97; flow rate: 15 ml/min; 24° C.; detection: 260 nm] gives 45 mg of the title compound having an ee of >99%.

$R_t$=5.51 min [column: Chiralpak IA, 250×4.6 mm; mobile phase: isopropanol/isohexane 3:97; flow rate: 2 ml/min; detection: 230 nm].

$^1$H-NMR (300 MHz, CDCl$_3$): δ=7.17 (d, 2H), 7.11-7.03 (m, 1H), 7.00-6.89 (m, 4H), 6.71 (d, 2H), 4.53-4.48 (m, 1H), 3.68 (dd, 2H), 3.02 (heptet, 1H), 2.72-2.59 (m, 1H), 2.50-2.36 (m, 1H), 2.32-2.08 (m, 3H), 2.00-1.86 (m, 2H), 1.80-1.66 (m, 1H), 1.42 (d, 1H), 1.17 (d, 3H), 1.11 (d, 3H).

MS (ESIpos): m/z=455 (M+H–H$_2$O)$^+$.

Example 37

[(4S)-5-(4-Fluorophenyl)-4-hydroxy-7-isopropyl-3,4-dihydrospiro[chromen-2,1'-cyclobutan]-6-yl]-[4-(trifluoromethoxy)phenyl]methanone

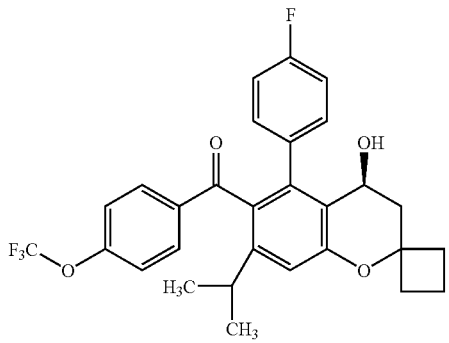

Under argon, 1.6 mg (0.01 mmol) of (1R,2S)-1-aminoindan-2-ol are dissolved in 1.5 ml of abs. tetrahydrofuran, 76 µl (0.43 mmol) of borane/N,N-diethylaniline complex are added and the mixture is stirred at room temperature for 30 min. After this time, 54.5 mg (0.11 µmol) of 5-(4-fluorophenyl)-7-isopropyl-6-[4-(trifluoromethoxy)benzoyl]spiro[chromen-2,1'-cyclobutan]-4(3H)-one (Example 60A), dissolved in 2.5 ml of abs. tetrahydrofuran, are added at room temperature over a period of 10 min, and the mixture is then stirred at room temperature for 5 h. 2 ml of methanol are added and the mixture is stirred for 15 min and then concentrated to dryness. The residue is taken up in ethyl acetate and washed twice with 1 N hydrochloric acid, twice with saturated sodium bicarbonate solution and twice with saturated sodium chloride solution. The organic phase is dried over sodium sulfate, filtered and concentrated. The crude product is purified by preparative HPLC. This gives 40 mg (73% of theory) of the title compound having an ee of 91%.

$R_t$=6.02 min [column: Chiralpak IA, 250×4.6 mm; mobile phase: isopropanol/isohexane 3:97; flow rate: 2 ml/min; detection: 260 nm].

$^1$H-NMR (400 MHz, CDCl$_3$): δ=7.58 (d, 2H), 7.22-6.60 (m, 7H), 4.62 (br. s, 1H), 2.78-2.61 (m, 2H), 2.47 (q, 1H), 2.33-2.12 (m, 3H), 2.08-1.91 (m, 2H), 1.81-1.69 (m, 1H), 1.28-1.09 (m, 6H).

MS (DCI): m/z=515 (M+H)$^+$, 532 (M+NH$_4$)$^+$.

Example 38 and Example 39

(4S)-5-(4-Fluorophenyl)-6-{(S)-hydroxy[4-(trifluoromethoxy)phenyl]methyl}-7-isopropyl-3,4-dihydrospiro[chromen-2,1'-cyclobutan]-4-ol
(Example 38)

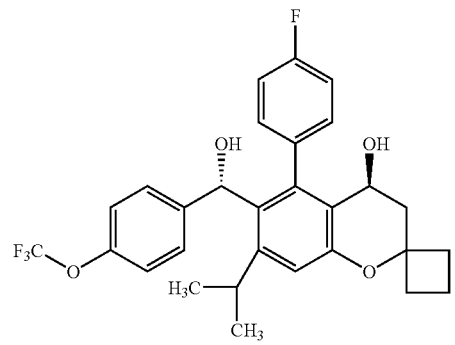

and (4S)-5-(4-fluorophenyl)-6-{(R)-hydroxy[4-(trifluoromethoxy)phenyl]methyl}-7-isopropyl-3,4-dihydrospiro[chromen-2,1'-cyclobutan]-4-ol
(Example 39)

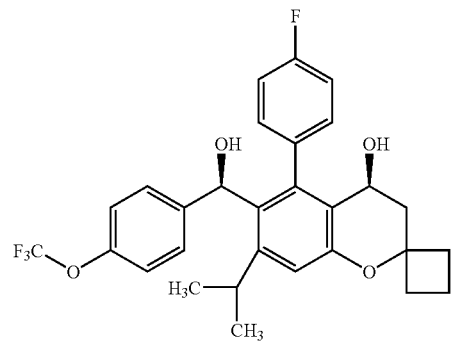

Under argon, 1.5 mg (0.01 mmol) of (1R,2S)-1-aminoindan-2-ol are dissolved in 1.5 ml of abs. tetrahydrofuran, 69 µl (0.39 mmol) of borane/N,N-diethylaniline complex are added and the mixture is stirred at room temperature for 30 min. After this time, 50 mg (0.10 mmol) of 5-(4-fluorophenyl)-6-{hydroxy[4-(trifluoromethoxy)phenyl]methyl}-7-isopropylspiro[chromen-2,1'-cyclobutan]-4(3H)-one (Example 58A), dissolved in 2 ml of abs. tetrahydrofuran, are added at room temperature over a period of 10 min, and the mixture is then stirred at room temperature overnight. 2 ml of methanol are added, and the mixture is stirred for 15 min and then concentrated to dryness. The residue is taken up in ethyl acetate and washed twice with 1 N hydrochloric acid, twice with saturated sodium bicarbonate solution and twice with saturated sodium chloride solution. The organic phase is dried over sodium sulfate, filtered and concentrated. The crude product is purified by preparative thick-layer chromatography (mobile phase: cyclohexane/ethyl acetate 5:1). This gives 13.5 mg (27% of theory, 78% ee) of Example 38 and 16.5 mg (33% of theory) of Example 39.

Example 38

$R_t$=7.70 min [column: Chiralpak IA, 250×4.6 mm; mobile phase: isopropanol/isohexane 3:97; flow rate: 2 ml/min; detection: 254 nm].
¹H-NMR (300 MHz, CDCl₃): δ=7.33-7.30 (m, 3H), 7.18-7.03 (m, 5H), 6.91 (s, 1H), 5.62 (d, 1H), 4.53-4.47 (m, 1H), 3.05 (heptet, 1H), 2.73-2.60 (m, 1H), 2.49-2.37 (m, 1H), 2.33-2.09 (m, 3H), 2.00-1.88 (m, 2H), 1.81-1.68 (m, 1H), 1.44 (d, 1H), 1.18 (d, 3H), 0.71 (d, 3H).
LC/MS (method 7): $R_t$=3.06 min
MS (ESIpos): m/z=499 (M+H−H₂O)⁺.

Example 39

¹H-NMR (300 MHz, CDCl₃): δ=7.32-7.25 (m, 1H), 7.21-7.04 (m, 7H), 6.91 (s, 1H), 5.62 (d, 1H), 4.53-4.48 (m, 1H), 3.04 (quin, 1H), 2.72-2.60 (m, 1H), 2.50-2.38 (m, 1H), 2.36-2.09 (m, 3H), 2.03-1.88 (m, 2H), 1.81-1.68 (m, 1H), 1.40 (d, 1H), 1.20 (d, 3H), 0.68 (d, 3H).
LC/MS (method 7): $R_t$=3.13 min
MS (ESIpos): m/z=499 (M+H−H₂O)⁺.

Example 40

(4S)-5-(4-Fluorophenyl)-6-{fluoro[4-(trifluoromethoxy)phenyl]methyl}-7-isopropyl-3,4-dihydrospiro[chromen-2,1'-cyclobutan]-4-ol

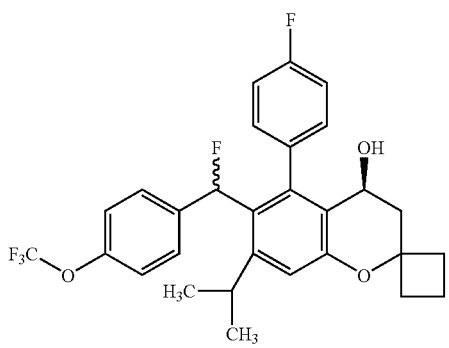

Under argon, 0.6 mg (0.004 mmol) of (1R,2S)-1-aminoindan-2-ol is dissolved in 0.5 ml of abs. tetrahydrofuran, 27.5 µl (0.15 mmol) of borane/N,N-diethylaniline complex are added and the mixture is stirred at room temperature for 30 min. After this time, 20 mg (0.04 mmol) of 5-(4-fluorophenyl)-6-{fluoro[4-(trifluoromethoxy)phenyl]methyl}-7-isopropylspiro[chromen-2,1'-cyclobutan]-4(3H)-one (Example 59A), dissolved in 1 ml of abs. tetrahydrofuran, are then added at room temperature over a period of 10 min, and the mixture is then stirred at room temperature overnight. 3 ml of methanol are added, and the mixture is stirred for 15 min and then concentrated to dryness. The residue is taken up in ethyl acetate and washed twice with 1 N hydrochloric acid, twice with saturated sodium bicarbonate solution and twice with saturated sodium chloride solution. The organic phase is dried over sodium sulfate, filtered and concentrated. The crude product is purified by thick-layer chromatography (mobile phase: cyclohexane→cyclohexane/ethyl acetate 5:1). This is followed by further purification by preparative HPLC. This gives 5.3 mg (26% of theory) of the title compound as a mixture of diastereomers.
¹H-NMR (300 MHz, CDCl₃): δ=7.38-6.90 (m, 9H), 6.23 (d, 1H), 4.57-4.47 (m, 1H), 2.98-2.87 (m, 1H), 2.73-2.60 (m, 1H), 2.51-2.10 (m, 4H), 2.03-1.87 (m, 2H), 1.80-1.68 (m, 1H), 1.45-1.39 (m, 1H), 1.20-1.12 (m, 3H), 0.88-0.73 (m, 3H).
MS (ESIpos): m/z=501 (M+H−H₂O)⁺.

Example 41

(4S)-5-(4-Fluorophenyl)-7-isopropyl-6-[4-(trifluoromethoxy)benzyl]-3,4-dihydrospiro[chromen-2,1'-cyclobutan]-4-ol

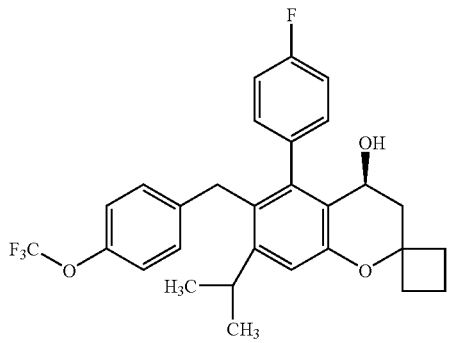

The title compound is obtained as a by-product in the preparation of Example 40.
Yield: 5.5 mg (28% of theory)
¹H-NMR (300 MHz, CDCl₃): δ=7.13-7.03 (m, 1H), 7.02-6.90 (m, 6H), 6.80 (d, 2H), 4.53-4.47 (m, 1H), 3.70 (dd, 2H), 2.93 (heptet, 1H), 2.70-2.60 (m, 1H), 2.49-2.38 (m, 1H), 2.32-2.10 (m, 3H), 1.99-1.89 (m, 2H), 1.78-1.68 (m, 1H), 1.41 (d, 1H), 1.17 (d, 3H), 1.12 (d, 3H).
MS (DCI): m/z=501 (M+H)⁺, 518 (M+NH₄)⁺.

Example 42 and Example 43

(4S)-5-Cyclopentyl-6-{(S)-fluoro[4-(trifluoromethyl)phenyl]methyl}-7-isopropyl-3,4-dihydrospiro-[chroman-2,1'-cyclobutan]-4-ol (Example 42)

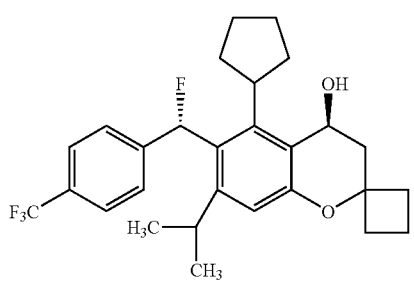

and (4S)-5-cyclopentyl-6-{(R)-fluoro[4-(trifluoromethyl)phenyl]methyl}-7-isopropyl-3,4-dihydrospiro-[chroman-2,1'-cyclobutan]-4-ol (Example 43)

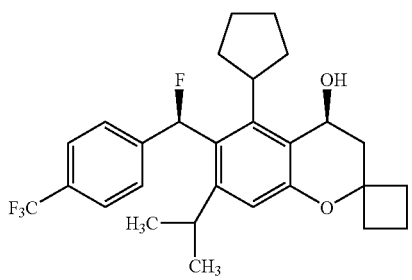

The title compounds are prepared analogously to the procedure of Example 7 and Example 8.

Example 42

Yield: 45 mg (26% of theory)
LC/MS (method 7): R$_t$=3.29 min
HPLC (method 4): R$_t$=5.18 min
MS (ESIpos): m/z=459 (M+H−H$_2$O)$^+$
$^1$H-NMR (CDCl$_3$, 300 MHz): δ=0.68 (d, 3H), 1.06 (d, 3H), 1.59-2.32 (m, 12H), 2.36-2.53 (m, 2H), 2.60-2.82 (m, 2H), 3.78 (quin, 1H), 5.01-5.10 (m, 1H), 6.78 (s, 1H), 6.94 (d, 1H), 7.37 (d, 2H), 7.59 (d, 2H).

Example 43

Yield: 26 mg (15% of theory)
LC/MS (method 7): R$_t$=3.32 min
HPLC (method 4): R$_t$=5.84 min
MS (ESIpos): m/z=459 (M+H−H$_2$O)$^+$
$^1$H-NMR (CDCl$_3$, 300 MHz): δ=0.67 (d, 3H), 1.08 (d, 3H), 1.58-2.28 (m, 12H), 2.38-2.59 (m, 2H), 2.61-2.82 (m, 2H), 3.79 (quin, 1H), 4.98-5.05 (m, 1H), 6.80 (s, 1H), 6.89 (d, 1H), 7.33 (d, 2H), 7.58 (d, 2H).

The examples listed in Table 1 below are prepared analogously to the processes described above from Example 48A:

TABLE 1

| Example No. | Structure | Analytical data |
| --- | --- | --- |
| 44 | 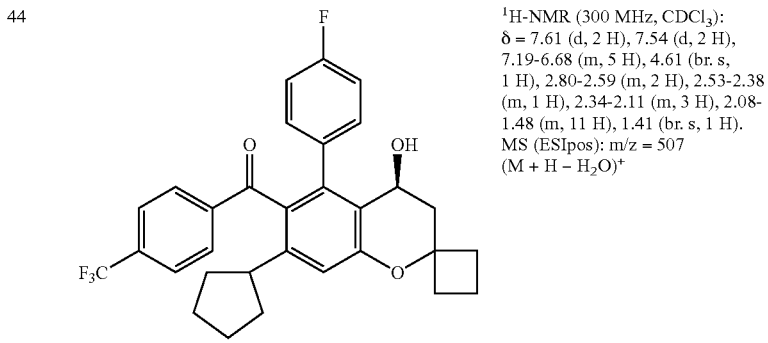 | $^1$H-NMR (300 MHz, CDCl$_3$): δ = 7.61 (d, 2 H), 7.54 (d, 2 H), 7.19-6.68 (m, 5 H), 4.61 (br. s, 1 H), 2.80-2.59 (m, 2 H), 2.53-2.38 (m, 1 H), 2.34-2.11 (m, 3 H), 2.08-1.48 (m, 11 H), 1.41 (br. s, 1 H). MS (ESIpos): m/z = 507 (M + H − H$_2$O)$^+$ |
| 45 | 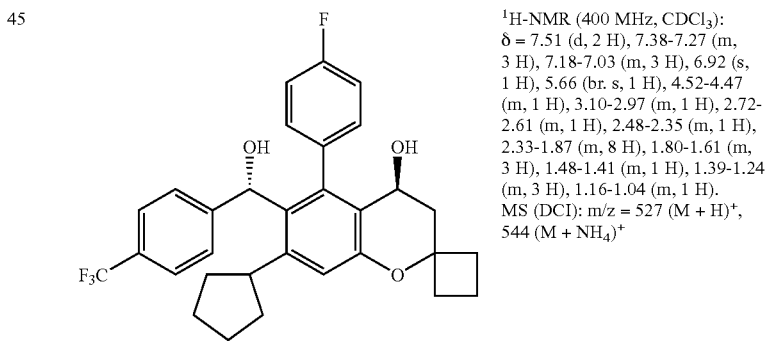 | $^1$H-NMR (400 MHz, CDCl$_3$): δ = 7.51 (d, 2 H), 7.38-7.27 (m, 3 H), 7.18-7.03 (m, 3 H), 6.92 (s, 1 H), 5.66 (br. s, 1 H), 4.52-4.47 (m, 1 H), 3.10-2.97 (m, 1 H), 2.72-2.61 (m, 1 H), 2.48-2.35 (m, 1 H), 2.33-1.87 (m, 8 H), 1.80-1.61 (m, 3 H), 1.48-1.41 (m, 1 H), 1.39-1.24 (m, 3 H), 1.16-1.04 (m, 1 H). MS (DCI): m/z = 527 (M + H)$^+$, 544 (M + NH$_4$)$^+$ |

TABLE 1-continued
| Example No. | Structure | Analytical data |
|---|---|---|
| 46 | 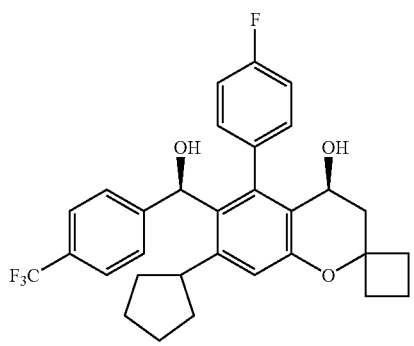 | ¹H-NMR (300 MHz, CDCl₃): δ = 7.49 (d, 2 H), 7.36-7.26 (m, 3 H), 7.21-7.05 (m, 3 H), 6.93 (s, 1 H), 5.62 (br. s, 1 H), 4.53-4.47 (m, 1 H), 3.11-2.97 (m, 1 H), 2.72-2.60 (m, 1 H), 2.50-2.38 (m, 1 H), 2.36-2.28 (m, 1 H), 2.26-1.87 (m, 6 H), 1.80-1.48 (m, 5 H), 1.39 (d, 1 H), 1.31-1.19 (d, 2 H), 1.02-0.91 (m, 1 H). |
| 47 | 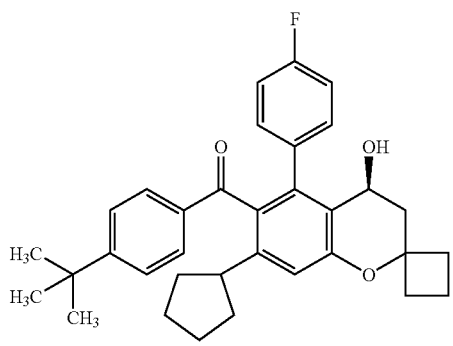 | ¹H-NMR (300 MHz, CDCl₃): δ = 7.50-7.38 (m, 2 H), 7.28 (d, 2 H), 7.16-6.58 (m, 5 H), 4.60 (br. s, 1 H), 2.83-2.58 (m, 2 H), 2.52-2.37 (m, 1 H), 2.34-2.11 (m, 3 H), 2.08-1.88 (m, 3 H), 1.81-1.45 (m, 8 H), 1.31-1.21 (m, 10 H). MS (DCI): m/z = 513 (M + H)⁺, 530 (M + NH₄)⁺ |
| 48 | 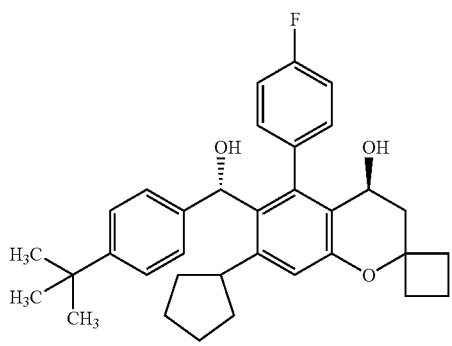 | ¹H-NMR (400 MHz, CDCl₃): δ = 7.35-7.27 (m, 3 H), 7.18-7.00 (m, 5 H), 6.91 (s, 1 H), 5.66 (br. s, 1 H), 4.52-4.47 (m, 1 H), 3.20-3.09 (m, 1 H), 2.70-2.61 (m, 1 H), 2.48-2.37 (m, 1 H), 2.33-2.19 (m, 2 H), 2.18-2.08 (m, 1 H), 2.05-1.88 (m, 4 H), 1.79-1.47 (m, 5 H), 1.43 (d, 1 H), 1.32-1.20 (m, 11 H), 1.16-1.04 (m, 1 H). MS (ESIpos): m/z =497 (M + H − H₂O)⁺ |
| 49 | 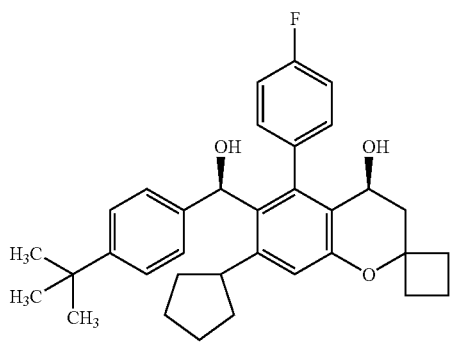 | ¹H-NMR (300 MHz, CDCl₃): δ = 7.32-7.16 (m, 4 H), 7.12-7.03 (m, 4 H), 6.92 (s, 1 H), 5.64 (br. s, 1 H), 4.55-4.49 (m, 1 H), 3.21-3.08 (m, 1 H), 2.72-2.59 (m, 1 H), 2.47-2.33 (m, 1 H), 2.33-2.27 (m, 1 H), 2.25-1.83 (m, 6 H), 1.80-1.45 (m, 5 H), 1.39 (d, 1 H), 1.35-1.18 (m, 11 H), 1.01-0.94 (m, 1 H). |

TABLE 1-continued

| Example No. | Structure | Analytical data |
|---|---|---|
| 50 | 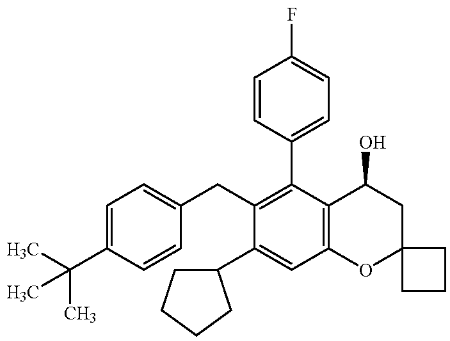 | ¹H-NMR (300 MHz, CDCl₃): δ = 7.16 (d, 2 H), 7.08-7.01 (m, 1 H), 7.00-6.89 (m, 4 H), 6.71 (d, 2 H), 4.53-4.46 (m, 1 H), 3.69 (dd, 2 H), 3.14-3.02 (m, 1 H), 2.70-2.59 (m, 1 H), 2.48-2.34 (m, 1 H), 2.30-2.07 (m, 3 H), 1.99-1.69 (m, 7 H), 1.64-1.49 (m, 3 H), 1.43-1.38 (m, 1 H), 1.28 (m, 9 H), 0.94-0.80 (m, 1 H). MS (ESIpos): m/z = 481 (M + H − H₂O)⁺ |
| 51 | 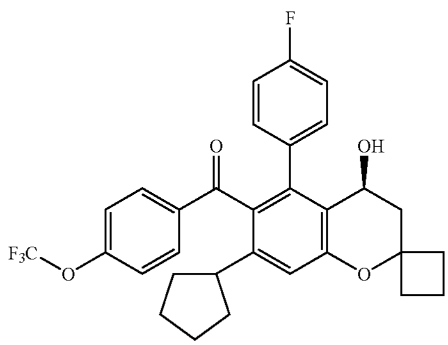 | ¹H-NMR (400 MHz, CDCl₃): δ = 7.57 (d, 2 H), 7.28-6.58 (m, 7 H), 4.63 (br. s, 1 H), 2.80-2.58 (m, 4 H), 2.49-2.39 (m, 1 H), 2.34-2.12 (m, 3 H), 2.08-1.89 (m, 2 H), 1.82-1.45 (m, 7 H). MS (DCD: m/z 541 (M + H)⁺, 558 (M + NH₄)⁺ |
| 52 | 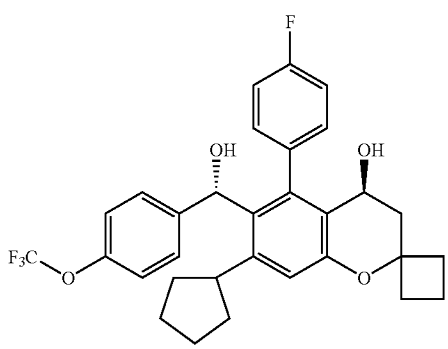 | ¹H-NMR (400 MHz, CDCl₃): δ = 7.31-7.17 (m, 4 H), 7.16-7.00 (m, 4 H), 6.91 (s, 1 H), 5.62 (br. s, 1 H), 4.49-4.44 (m, 1 H), 3.12-3.01 (m, 1 H), 2.70-2.59 (m, 1 H), 2.47-2.34 (m, 1 H), 2.32-2.19 (m, 2 H), 2.18-1.88 (m, 5 H), 1.79-1.47 (m, 4 H), 1.42 (d, 1 H), 1.24-1.03 (m, 2 H), 0.98-0.78 (m, 2 H). MS (DCI): m/z = 542 (M)⁺, 560 (M + NH₄)⁺ |
| 53 | 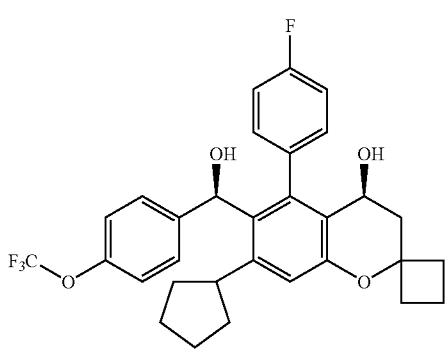 | 1 H-NMR (400 MHz, CDCl₃): δ = 7.31-7.27 (m, 1 H), 7.20-7.15 (m, 3 H), 7.14-7.05 (m, 4 H), 6.92 (s, 1 H), 5.62 (br. s, 1 H), 4.53-4.48 (m, 1 H), 3.13-3.02 (m, 1 H), 2.70-2.61 (m, 1 H), 2.47-2.38 (m, 1 H), 2.32-2.27 (m, 1 H), 2.23-1.88 (m, 5 H), 1.80-1.47 (m, 4 H), 1.39 (d, 1 H), 1.30-1.19 (m, 2 H), 1.08-0.98 (m, 1 H), 0.95-0.79 (m, 2 H). MS (DCI): m/z = 542 (M)⁺, 560 (M + NH₄)⁺ |

TABLE 1-continued

| Example No. | Structure | Analytical data |
|---|---|---|
| 54 | 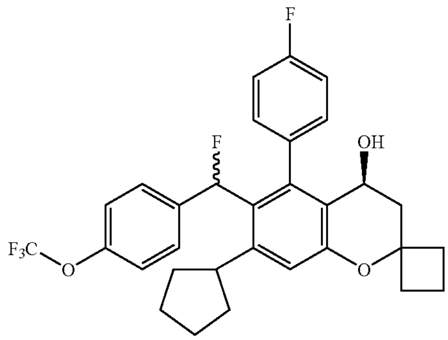 | $^1$H-NMR (300 MHz, CDCl$_3$): δ = 7.37-6.92 (m, 9 H), 6.25 (d, 1 H), 4.57-4.47 (m, 1 H), 3.04-2.89 (m, 1 H), 2.73-2.59 (m, 1 H), 2.50-1.87 (m, 7 H), 1.81-1.48 (m, 4 H), 1.41-1.10 (m, 5 H). MS (ESIpos): m/z = 527 (M + H − H$_2$O)$^+$ |

The examples listed in Table 2 below are prepared analogously to the processes described above from Example 47A:

TABLE 2

| Example No. | Structure | Analytical data |
|---|---|---|
| 55 | 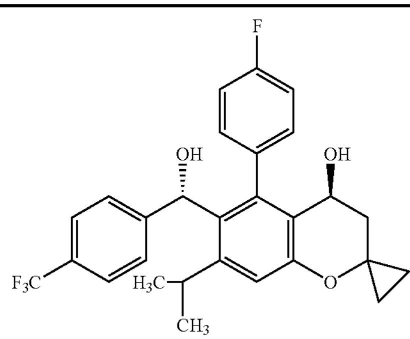 | $^1$H-NMR (400 MHz, CDCl$_3$): δ = 7.51 (d, 2 H), 7.41-7.29 (m, 3 H), 7.21-7.03 (m, 3 H), 6.83 (s, 1 H), 5.67 (br. s, 1 H), 4.49-4.42 (m, 1 H), 3.01 (heptet, 1 H), 2.55-2.47 (m, 1 H), 2.12-2.08 (m, 1 H), 1.78 (d, 1 H), 1.60 (d, 1 H), 1.15 (d, 3 H), 1.11-0.99 (m, 2 H), 0.92-0.80 (m, 2 H), 0.64 (d, 3 H). MS (DCI): m/z = 486 (M)$^+$, 504 (M + NH$_4$)$^+$ |
| 56 | 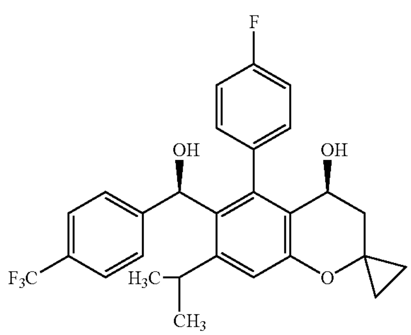 | $^1$H-NMR (400 MHz, CDCl$_3$): δ = 7.50 (d, 2 H), 7.38-7.29 (m, 3 H), 7.21-7.03 (m, 3 H), 6.84 (s, 1 H), 5.67 (br. s, 1 H), 4.50-4.43 (m, 1 H), 3.00 (heptet, 1 H), 2.55-2.50 (m, 1 H), 2.10 (d, 1 H), 1.70 (d, 1 H), 1.64-1.56 (m, 1 H), 1.17 (d, 3 H), 1.11-0.97 (m, 2 H), 0.91-0.80 (m, 2 H), 0.68 (d, 3 H). MS (DCI): m/z = 486 (M)$^+$, 504 (M + NH$_4$)$^+$ |
| 57 | 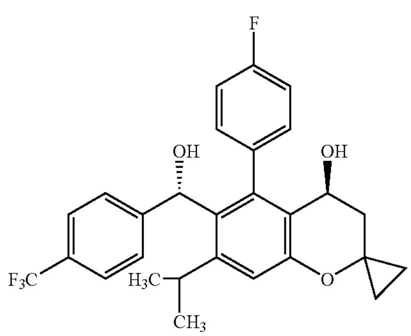 | $^1$H-NMR (400 MHz, CDCl$_3$): δ = 7.54 (d, 2 H), 7.36-7.19 (m, 4 H), 7.15-7.02 (m, 2 H), 6.87 (s, 1 H), 6.30 (d, 1 H), 4.52-4.47 (m, 1 H), 2.94-2.82 (m, 1 H), 2.57-2.49 (m, 1 H), 1.77 (d, 1 H), 1.65-1.59 (m, 1 H), 1.17 (d, 3 H), 1.11-1.00 (m, 2 H), 0.90-0.83 (m, 1 H), 0.72 (d, 3 H), 0.69-0.63 (m, 1 H). MS (DCI): m/z = 488 (M)$^+$, 506 (M + NH$_4$)$^+$ |

TABLE 2-continued

| Example No. | Structure | Analytical data |
|---|---|---|
| 58 | 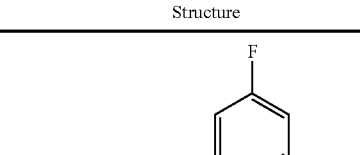 | $^1$H-NMR (400 MHz, CDCl$_3$): δ = 7.54 (d, 2 H), 7.42-7.37 (m, 1 H), 7.24 (d, 2 H), 7.13-6.99 (m, 3 H), 6.88 (s, 1 H), 6.30 (d, 1 H), 4.49-4.44 (m, 1 H), 2.93-2.82 (m, 1 H), 2.58-2.49 (m, 1 H), 1.73 (br. s, 1 H), 1.64-1.59 (m, 1 H), 1.17 (d, 3 H), 1.10-0.99 (m, 2 H), 0.90-0.83 (m, 1 H), 0.67 (d, 3 H), 0.69-0.62 (m, 1 H). MS (DCI): m/z 488 (M)$^+$, 506 (M + NH$_4$)$^+$ |

For the chromatographic separation of the two diastereomers Example 57 and Example 58 (227 mg), the following chiral phase is used: Kromasil TBB, 250 mm×20 mm; mobile phase: MTBE/isohexane 10:90; flow rate: 25 ml/min; 24° C.; detection: 250 nm. This gives 56 mg (23% of theory, 98% ee) of diastereomer Example 57 and 90 mg (37% of theory, 97% ee) of diastereomer Example 58.

B. ASSESSMENT OF THE PHARMACOLOGICAL ACTIVITY

The pharmacological action of the compounds according to the invention can be demonstrated in the following assays:
B-I. CETP Inhibition Testing
B-I.1. Obtainment of CETP CETP is obtained in partially purified form from human plasma by differential centrifugation and column chromatography and used for the test. To this end, human plasma is adjusted to a density of 1.21 g per ml using NaBr and centrifuged at 4° C. at 50 000 rpm for 18 h. The bottom fraction (d>1.21 g/ml) is applied to a Phenyl-Sepharose 26/10 HP fast flow-column (Pharmacia), washed with PBS buffer and then eluted with distilled water. 10 parts of PBS buffer and 1% (w/v) BSA are added to the eluate. The CETP-active fractions are pooled.
B-I.2. CETP Fluorescence Test Measurement of the CETP-catalyzed transfer of a fluorescent cholesterol ester between liposomes [modified according to the procedure of Bisgaier et al., J. Lipid Res. 34, 1625 (1993)]:

For the production of the donor liposomes, 1 mg of cholesteryl 4,4-difluoro-5,7-dimethyl-4-bora-3a,4a-diaza-s-indacene-3-dodecanoate (cholesteryl BODIPY® FL C$_{12}$, Molecular Probes) is dissolved in 2 ml of chloroform with 5.35 mg of triolein and 6.67 mg of phosphatidylcholine. The solvent is removed at medium temperature in a SpeedVac and the residue is dried under high vacuum for 1 h. The residue is then dissolved in 600 μl of dioxane with gentle warming in an ultrasonic bath and this solution is added very slowly with ultrasonication to 63 ml of 50 mM Tris/HCl, 150 mM NaCl, 2 mM EDTA buffer pH 7.3 at room temperature. The suspension is then ultrasonicated under an N2 atmosphere for 30 minutes in the Branson ultrasonic bath at about 50 watts, the temperature being kept at about 20° C.

The acceptor liposomes are obtained analogously from 86 mg of cholesteryl oleate, 20 mg of triolein and 100 mg of phosphatidylcholine dissolved in 1.2 ml of dioxane and 114 ml of the above buffer by ultrasonication at 50 watts (20° C.) for 30 minutes.

B-I.2.1. CETP Fluorescence Test with Enriched CETP

For testing, a test mix consisting of 1 part of above buffer, 1 part of donor liposomes and 2 parts of acceptor liposomes is used.

50 μl of test mix are treated with 48 μl of enriched CETP fraction (1-3 μg), obtained from human plasma by means of hydrophobic chromatography, and 2 μl of a solution of the substance to be investigated in DMSO and incubated at 37° C. for 4 h.

The change in the fluorescence at 485/535 nm is a measure of the CE transfer; the inhibition of the transfer in comparison to the control batch without substance is determined. Representative activity data (IC$_{50}$ values) for the compounds according to the invention are listed in Table 3:

TABLE 3

| Example No. | IC$_{50}$ [nM] fluorescence test |
|---|---|
| 1 | 340 |
| 4 | 90 |
| 5 | 35 |
| 7 | 32 |
| 8 | 373 |
| 9 | 90 |
| 10 | 93 |
| 11 | 63 |
| 14 | 176 |
| 15 | 38 |
| 17 | 70 |
| 18 | 792 |
| 19 | 200 |
| 20 | 49 |
| 22 | 51 |
| 24 | 30 |
| 26 | 48 |
| 27 | 35 |
| 28 | 77 |
| 30 | 18 |
| 31 | 53 |
| 32 | 19 |
| 33 | 59 |
| 34 | 14 |
| 35 | 800 |
| 36 | 28 |
| 37 | 36 |
| 40 | 50 |
| 41 | 19 |
| 42 | 26 |
| 43 | 61 |
| 44 | 45 |
| 45 | 26 |
| 47 | 50 |
| 48 | 33 |

TABLE 3-continued

| Example No. | IC$_{50}$ [nM] fluorescence test |
|---|---|
| 50 | 30 |
| 51 | 42 |
| 52 | 198 |
| 54 | 39 |
| 55 | 27 |
| 56 | 263 |
| 57 | 14 |
| 58 | 300 |

B-I.2.2. CETP Fluorescence Test with Human Plasma

6 µl (12% v/v) of donor liposomes and 1 µl (2% v/v) of a solution of the substance to be investigated in DMSO are added to 42 µl (86% v/v) of human plasma (Sigma P9523), and the mixture is incubated at 37° C. for 24 h.

The change in the fluorescence at 510/520 nm (gap width 2.5 nm) is a measure of the CE transfer; the inhibition of the transfer in comparison to the control batch without substance is determined.

B-I.2.3. Ex Vivo-CETP Fluorescence Test

10 µl of buffer and 2 µl of serum are added to 80 µl of test mix, and the mixture is incubated at 37° C. for 4 h.

The change in the fluorescence at 485/535 nm is a measure for the CE transfer; the inhibition of the transfer in comparison to the control batch without substance is determined.

B-I.3. CETP-SPA Test

For testing of the CETP activity, the transfer of $^3$H-cholesterol ester from human HD lipoproteins to biotinylated LD lipoproteins is measured. The reaction is ended by addition of streptavidin-SPA® beads (Amersham) and the transferred radioactivity is determined directly in a liquid scintillation counter.

In the test batch, 10 µl of HDL-3H-cholesterol ester (about 50 000 cpm) are incubated at 37° C. for 18 h with 10 µl of biotin-LDL (Amersham) in 50 mM Hepes/0.15 M NaCl/0.1% bovine serum albumin (RSA)/0.05% NaN$_3$ pH 7.4 containing 10 µl of CETP (1 mg/ml) and 3 µl of a solution of the substance to be tested (dissolved in 10% DMSO/1% RSA). 200 µl of the SPA-streptavidin bead solution (TRKQ 7005) are then added, incubated further with shaking for 1 h and then measured in a scintillation counter. Corresponding incubations with 10 µl of buffer, 10 µl of CETP at 4° C. and 10 µl of CETP at 37° C. serve as controls.

The activity transferred in the control batches with CETP at 37° C. is rated as 100% transfer. The substance concentration at which this transfer is reduced to half is specified as the IC$_{50}$ value. Representative activity data for the compounds according to the invention are listed in Table 4:

TABLE 4

| Example No. | IC$_{50}$ [nM] SPA test |
|---|---|
| 4 | 62 |
| 5 | 29 |
| 7 | 20 |
| 9 | 33 |
| 11 | 51 |
| 19 | 300 |
| 22 | 57 |
| 24 | 16 |
| 27 | 18 |
| 28 | 22 |
| 30 | 12 |
| 31 | 20 |
| 32 | 4 |
| 33 | 16 |
| 34 | 5 |
| 35 | 400 |
| 36 | 6 |
| 37 | 30 |
| 41 | 15 |
| 42 | 21 |
| 43 | 100 |
| 44 | 31 |
| 45 | 21 |
| 47 | 38 |
| 48 | 14 |
| 49 | 400 |
| 50 | 15 |
| 51 | 100 |
| 52 | 30 |
| 55 | 4 |
| 57 | 6 |
| 58 | 68 |

B-II. Determination of the Ex Vivo and In Vivo Activity

B-II.1. Measurement of the Ex Vivo Activity on Transgenic hCETP Mice

To test for CETP-inhibitory activity, the substances are administered orally using a stomach tube to transgenic hCETP mice bred in-house [Dinchuk et al. BBA 1295-1301 (1995)]. To this end, male animals are randomly assigned to groups having an equal number of animals, as a rule n=4, one day before the start of the experiment. Before administration of the substance, blood is taken from each mouse by puncture of the retro-orbital venous plexus for the determination of its basal CETP activity in the serum (T1). The test substance is then administered perorally to the animals using the stomach tube. For this purpose, the substances are dissolved in 10% Solutol HS 15/10% ethanol/80% of a 0.9% strength sodium chloride solution; the administration volume is generally 10 ml per kg of body weight. At specific times after administration of the test substance, blood is taken from the animals by puncture a second time (T2), in general 16 or 24 h after substance administration, but if appropriate this can also be carried out at another time.

In order to be able to assess the inhibitory activity of a substance, for each time, i.e. 16 or 24 hours, a corresponding control group is employed whose animals only receive the formulating agent without substance. In the control animals, the two blood samplings per animal are carried out as in the substance-treated animals in order to be able to determine the change in the CETP activity without inhibitor over the corresponding experimental time interval (16 or 24 h).

After termination of the clotting, the blood samples are centrifuged and the serum is removed by pipette. For the determination of the CETP activity, the cholesteryl ester transport over 4 h is determined. To this end, in general 2 µl of serum are employed in the test batch and the test is carried out as described under B-I.2.3.

The differences in the cholesteryl ester transport [pM CE/h (T2)–pM CE/h (T1)] are calculated for each animal and averaged in the groups. A substance which at one of the times reduces the cholesteryl ester transport by >20% is regarded as active.

B-II.2. Measurement of the In Vivo Activity in Syrian Golden Hamsters

Female Syrian golden hamsters bred in-house (strain BAY: DSN) and having a weight of 150-200 g are used to determine the oral action of CETP inhibitors on serum lipoproteins and triglycerides. The animals are grouped in six animals per cage and acclimatized to feed and water ad libitum for two weeks.

Immediately prior to the start of the experiment and after the substance has been administered, blood is withdrawn by retro-orbital puncture of the venous plexus and used to obtain serum after 30 min of incubation at room temperature and 20 min of centrifugation at 30 000 g. The substances are dissolved in 20% Solutol/80% water and administered perorally by means of a stomach tube. The control animals receive identical volumes of solvent without test substance.

Triglycerides, total cholesterol, HDL cholesterol and LDL cholesterol are determined using the analytical instrument COBAS INTEGRA 400 plus (from Roche Diagnostics) according to the instructions of the manufacturer. From the measured values, for each parameter, the change in percent caused by the treatment with the substance is calculated for each animal and stated as mean with standard deviation per group (n=6 or n=12). If, compared to the group treated with solvent, the effects of the substance are significant, the p-value determined by application of the t-test is added (* $p \leq 0.05$;  $p \leq 0.01$; * $p \leq 0.005$).

B-II.3. Measurement of the In Vivo Activity in Transgenic hCETP Mice

To determine the oral action on lipoproteins and triglycerides, test substance is administered perorally to transgenic mice [Dinchuk et al., BBA, 1295-1301 (1995)] using a stomach tube once a day on 3 days. For this purpose, the substances are dissolved in 10% Solutol HS 15/10% ethanol/80% of a 0.9% strength sodium chloride solution; the administration volume is generally 10 ml per kg of body weight. Before the start of the experiment, blood is withdrawn from the mice retro-orbitally in order to determine cholesterol and triglycerides in the serum. The serum is obtained as described above for hamsters by incubation at room temperature for 30 min and subsequent centrifugation at 6000 g. On the day after the last administration of substance, blood is again withdrawn from the mice in order to determine lipoproteins and triglycerides. The changes in the parameters measured are expressed as the percentage change compared with the starting value.

Representative activity data for the compounds according to the invention are listed in Table 5:

TABLE 5

| Example No. | % increase of HDL after 3 d (dose: 3 × 3 mg/kg) |
|---|---|
| 7 | 67 |
| 28 | 25 |
| 30 | 83 |
| 32 | 31 |
| 36 | 40 |
| 42 | 81 |

C. WORKING EXAMPLES OF PHARMACEUTICAL COMPOSITIONS

The compounds of the invention can be converted into pharmaceutical preparations in the following ways:

Tablet:
Composition:
100 mg of the compound of the invention, 50 mg of lactose (monohydrate), 50 mg of corn starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:
The mixture of compound of the invention, lactose and starch is granulated with a 5% strength solution (m/m) of the PVP in water. The granules are dried and mixed with the magnesium stearate for 5 minutes. This mixture is compressed in a conventional tablet press (see above for format of the tablet). A guideline compressive force for the compression is 15 kN.

Suspension which can be Administered Orally:
Composition:
1000 mg of the compound of the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound of the invention.

Production:
The Rhodigel is suspended in ethanol, and the compound of the invention is added to the suspension. The water is added while stirring. The mixture is stirred for about 6 h until the swelling of the Rhodigel is complete.

Solution which can be Administered Orally:
Composition:
500 mg of the compound of the invention, 2.5 g of polysorbate and 97 g of polyethylene glycol 400.20 g of oral solution correspond to a single dose of 100 mg of the compound of the invention.

Production:
The compound of the invention is suspended in the mixture of polyethylene glycol and polysorbate with stirring. The stirring process is continued until the compound of the invention has completely dissolved.

i.v. Solution:
The compound of the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:

1. A compound of formula (I)

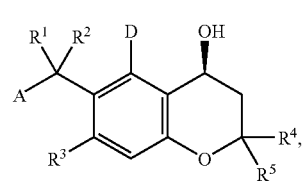

in which
A represents a group of the formula

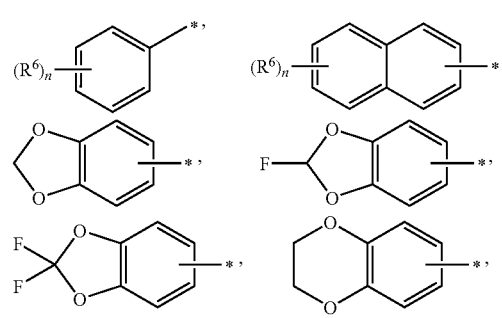

-continued

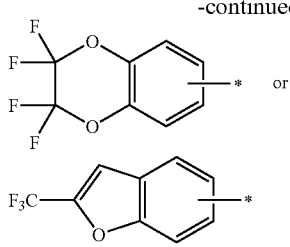

in which
* represents the point of attachment to the $CR^1R^2$ grouping,
$R^6$ represents a substituent selected from the group consisting of halogen, cyano, $(C_1-C_6)$-alkyl and $(C_1-C_6)$-alkoxy, where alkyl and alkoxy for their part may be substituted up to five times by fluorine,
and
n represents the number 0, 1, 2 or 3,
where, if the substituent $R^6$ is present more than once, its meanings may be identical or different,
D represents $(C_3-C_8)$-alkyl, $(C_4-C_8)$-cycloalkyl, $(C_4-C_8)$-cycloalkenyl, $(C_6-C_{10})$-aryl, 5- or 6-membered heteroaryl, tetrahydrofuranyl or tetrahydropyranyl, where aryl and heteroaryl for their part may be substituted by halogen, cyano, $(C_1-C_6)$-alkyl, $(C_1-C_6)$-alkoxy, trifluoromethyl or trifluoromethoxy
and
cycloalkyl and cycloalkenyl for their part may be substituted by fluorine or $(C_1-C_6)$-alkyl,
$R^1$ represents hydrogen, fluorine, hydroxyl, methoxy, mercapto or methyl,
$R^2$ represents hydrogen
or
$R^1$ and $R^2$ together with the carbon atom to which they are attached form a carbonyl group,
$R^3$ represents $(C_1-C_6)$-alkyl or $(C_3-C_7)$-cycloalkyl
and
$R^4$ and $R^5$ independently of one another represent hydrogen or $(C_1-C_4)$-alkyl or together with the carbon atom to which they are attached form a spiro-linked 3- to 5-membered cycloalkyl ring,
or a salt.

2. The compound of claim 1 in which
A represents a group of the formula

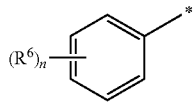

in which
* represents the point of attachment to the $CR^1R^2$ grouping,
$R^6$ represents a substituent selected from the group consisting of fluorine, chlorine, cyano, $(C_1-C_4)$-alkyl and $(C_1-C_4)$-alkoxy, where alkyl and alkoxy for their part may be substituted up to five times by fluorine,
and
n represents the number 0, 1, 2 or 3,
where, if the substituent $R^6$ is present more than once, its meanings may be identical or different,
D represents phenyl, thienyl, furyl, cyclopentyl, cyclohexyl, cyclopentenyl or cyclohexenyl, where phenyl, thienyl and furyl for their part may be substituted by fluorine, chlorine, cyano, $(C_1-C_4)$-alkyl, $(C_1-C_4)$-alkoxy, trifluoromethyl or trifluoromethoxy
and
cyclopentyl, cyclohexyl, cyclopentenyl and cyclohexenyl for their part may be substituted by fluorine or $(C_1-C_4)$-alkyl,
$R^1$ represents hydrogen, fluorine, hydroxyl or methyl,
$R^2$ represents hydrogen
or
$R^1$ and $R^2$ together with the carbon atom to which they are attached form a carbonyl group,
$R^3$ represents $(C_3-C_6)$-alkyl or $(C_3-C_6)$-cycloalkyl
and
$R^4$ and $R^5$ independently of one another represent hydrogen or methyl or together with the carbon atom to which they are attached form a spiro-linked 3- to 5-membered cycloalkyl ring,
or a salt.

3. The compound of claim 1 in which
A represents a group of the formula

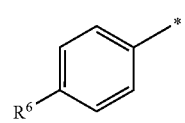

in which
* represents the point of attachment to the $CR^1R^2$ grouping
and
$R^6$ represents trifluoromethyl, trifluoromethoxy or tert-butyl,
D represents phenyl, 4-fluorophenyl, cyclopentyl, cyclohexyl, cyclopent-1-en-1-yl or cyclohex-1-en-1-yl,
$R^1$ represents hydrogen, fluorine or hydroxyl,
$R^2$ represents hydrogen
or
$R^1$ and $R^2$ together with the carbon atom to which they are attached form a carbonyl group,
$R^3$ represents isopropyl or cyclopentyl
and
$R^4$ and $R^5$ represent methyl or together with the carbon atom to which they are attached form a spiro-linked cyclopropyl or cyclobutyl ring,
or a salt.

4. A method of making a compound of claim 1, comprising
[A] coupling a compound of the formula (II)

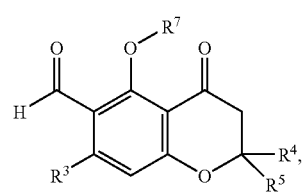

(II)

in which $R^3$, $R^4$ and $R^5$ are each as defined in claim 1
and
$R^7$ represents hydrogen, methyl or a hydroxyl protective group
in an inert solvent, if appropriate in the presence of a catalyst, with an organometallic compound of the formula (III)

A-Q (III), in which A is as defined in claim 1
and
Q represents Li, —MgBr, —ZnBr or —B(OH)$_2$,
to give a compound of the formula (IV)

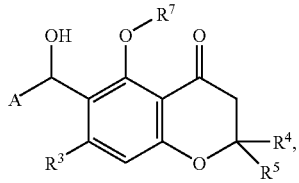
(IV)

in which A, R$^3$, R$^4$, R$^5$ and R$^7$ are each as defined above,
this compound is then oxidized to a compound of the formula (V)

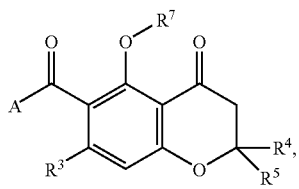
(V)

in which A, R$^3$, R$^4$, R$^5$ and R$^7$ are each as defined above,
then if R$^7$ represents methyl or a hydroxyl protective group, removing the radical, to produce a compound of the formula (Va)

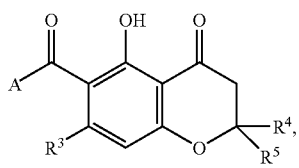
(Va)

in which A, R$^3$, R$^4$ and R$^5$ are each as defined above,
converting the resulting compound into a compound of the formula (VI)

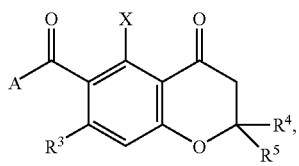
(VI)

in which A, R$^3$, R$^4$ and R$^5$ are each as defined above
and
X represents a leaving group, such as, for example, chlorine, bromine, iodine, tosylate, mesylate or triflate,
coupling the compound of formula (VI) in an inert solvent in the presence of a base and a palladium catalyst, with a boronic acid derivative of the formula (VII)

(VII)

in which D is as defined in claim 1
and
R$^8$ represents hydrogen or (C$_1$-C$_4$)-alkyl or both radicals together form a —C(CH$_3$)$_2$—C(CH$_3$)$_2$— bridge
to give a compound of the formula (VIII)

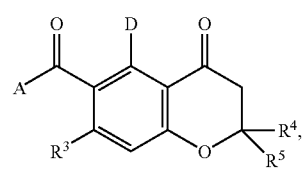
(VIII)

in which A, D, R$^3$, R$^4$ and R$^5$ are each as defined above,
and converting the compound of formula (VIII) by asymmetric reduction into a compound of the formula (I-A)

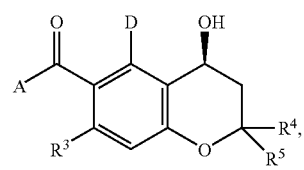
(I-A)

in which A, D, R$^3$, R$^4$ and R$^5$ are each as defined above
or
[B] converting a compound of the formula (IIa)

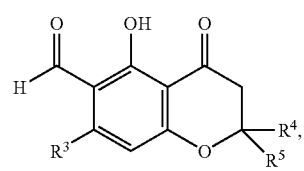
(IIa)

in which R$^3$, R$^4$ and R$^5$ are each as defined above
is into a compound of the formula (IX)

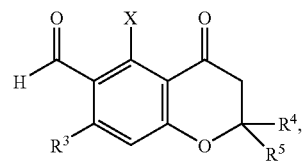
(IX)

in which X, R$^3$, R$^4$ and R$^5$ are each as defined above,
coupling the compound of formula (IX) in an inert solvent in the presence of a base and a palladium catalyst, with a boronic acid derivative of the formula (VII) to give a compound of the formula (X)

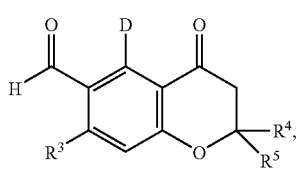

(X)

in which D, R$^3$, R$^4$ and R$^5$ are each as defined above, reacting the compound of formula (X) in an inert solvent, if appropriate in the presence of a catalyst, with an organometallic compound of the formula (III) to give a compound of the formula (XI)

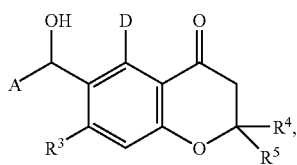

(XI)

in which A, D, R$^3$, R$^4$ and R$^5$ are each as defined above, and converting the compound of formula (XI) by asymmetric reduction into a compound of the formula (I-B)

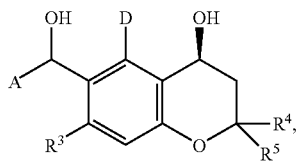

(I-B)

in which A, D, R$^3$, R$^4$ and R$^5$ are each as defined above, or converting the compound of the formula (XI) with the aid of a fluorinating agent into a compound of the formula (XII)

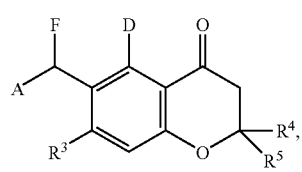

(XII)

in which A, D, R$^3$, R$^4$ and R$^5$ are each as defined above and converting the compound of formula (XII) by asymmetric reduction, into a compound of the formula (I-C)

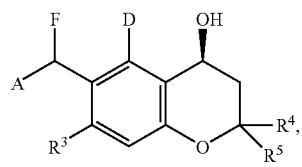

(I-C)

in which A, D, R$^3$, R$^4$ and R$^5$ are each as defined above, and optionally converting the compound of formula (I-A), (I-B) or (I-C) to the salt thereof.

5. A pharmaceutical composition comprising a compound of claim 1 in combination with an inert nontoxic pharmaceutically suitable auxiliary.

6. A pharmaceutical composition comprising a compound of claim 1 in combination with a further active compound selected from the group consisting of antidiabetics, substances having antithrombotic action, hypotensive substances, lipid metabolism-modifying substances, anti-inflammatory substances and substances which stabilize arteriosclerotic plaque, in combination with an inert nontoxic pharmaceutically suitable auxiliary.

7. The pharmaceutical composition of claim 6 wherein the further active compound is a HMG-CoA reductase inhibitor.

* * * * *